US010689423B2

(12) United States Patent
Williams et al.

(10) Patent No.: US 10,689,423 B2
(45) Date of Patent: Jun. 23, 2020

(54) CTLA4-BINDING PROTEIN PEPTIDE-LINKER MASKS

(71) Applicants: City of Hope, Duarte, CA (US); Thomas Jefferson University and Health System, Innovation Pillar, Philadelphia, PA (US)

(72) Inventors: John Williams, Monrovia, CA (US); Ulrich Rodeck, Philadelphia, PA (US)

(73) Assignees: City of Hope, Duarte, CA (US); Thomas Jefferson University and Health System Innovation Pillar, Philadelphia, PA (US)

( * ) Notice: Subject to any disclaimer, the term of this patent is extended or adjusted under 35 U.S.C. 154(b) by 0 days.

(21) Appl. No.: 15/543,209

(22) PCT Filed: Jan. 13, 2016

(86) PCT No.: PCT/US2016/013292
§ 371 (c)(1),
(2) Date: Jul. 12, 2017

(87) PCT Pub. No.: WO2016/115275
PCT Pub. Date: Jul. 21, 2016

(65) Prior Publication Data
US 2019/0169245 A1    Jun. 6, 2019

Related U.S. Application Data

(60) Provisional application No. 62/102,966, filed on Jan. 13, 2015.

(51) Int. Cl.
| | | |
|---|---|---|
| *C07K 14/705* | (2006.01) | |
| *C07K 7/06* | (2006.01) | |
| *C07K 5/12* | (2006.01) | |
| *C07K 19/00* | (2006.01) | |
| *C07K 14/47* | (2006.01) | |
| *A61K 47/64* | (2017.01) | |
| *A61K 47/65* | (2017.01) | |
| *C12N 15/62* | (2006.01) | |
| *A61K 38/00* | (2006.01) | |

(52) U.S. Cl.
CPC ......... *C07K 14/4703* (2013.01); *A61K 47/64* (2017.08); *A61K 47/65* (2017.08); *C07K 14/70521* (2013.01); *A61K 38/00* (2013.01); *C07K 2319/055* (2013.01); *C07K 2319/30* (2013.01); *C07K 2319/50* (2013.01); *C07K 2319/70* (2013.01); *C07K 2319/74* (2013.01)

(58) Field of Classification Search
CPC ......... C07K 14/4703; C07K 14/70521; C07K 2319/70; C07K 2319/00; C07K 2319/32; C07K 2319/055; C07K 2319/02; C07K 16/46; C07K 2319/74; C07K 2319/30; C07K 2319/50; C07K 7/06; A61K 47/65; A61K 47/64; A61K 38/00; C12N 15/62
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly |
| 4,861,760 A | 8/1989 | Mazuel et al. |
| 4,911,920 A | 3/1990 | Jani et al. |
| 4,946,778 A | 8/1990 | Ladner et al. |
| 5,212,162 A | 5/1993 | Missel et al. |
| 5,403,841 A | 4/1995 | Lang et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,777,085 A | 7/1998 | Co et al. |

(Continued)

FOREIGN PATENT DOCUMENTS

| | | |
|---|---|---|
| EP | 0173494 A3 | 11/1987 |
| WO | WO8702671 A1 | 5/1987 |

(Continued)

OTHER PUBLICATIONS

Stancovski et al., Proceedings of the National Academy of Science USA 88: 8691-8695 (Year: 1991).*
Rowshanravan et al., Blood 131(1): 58-67 (Year: 2018).*
Al-Muhammed, J. et al. (1996), "In-vivo studies on dexamethasone sodium phosphate liposomes", J. Microencapsul; 13:293-306.
Altschul, S.F. et al. (1990). "Basic Local Alignment Search Tool," J. Mol Biol. 215: 403-410.
Altschul, S.F. et al. (1997). "Gapped Blast and Psi-Blast: a New Generation of Protein Database Search Programs," Nucleic Acids Res. 25(17):3389-3402.

(Continued)

*Primary Examiner* — Phuong Huynh
(74) *Attorney, Agent, or Firm* — Mintz, Levin, Cohn, Ferris, Glovsky and Popeo, P.C.

(57) ABSTRACT

Provided herein are recombinant CTLA-4 binding proteins, which are, inter alia, useful for the treatment of cancer. The recombinant proteins provided herein are, inter alia, capable of binding CTLA-4 proteins on a tumor cell. In a first aspect, there is provided a recombinant CTLA-4 binding protein including (i) a CTLA-4 binding domain; (ii) a CTLA-4 binding domain masking peptide; and (iii) a cleavable peptide linker connecting the CTLA-4 binding domain masking peptide to the CTLA-4 binding domain. In another aspect, there is provided a dimerizing domain covalently attached to the CTLA-4 binding domain, wherein the binding protein domains are bound together.

15 Claims, 20 Drawing Sheets
Specification includes a Sequence Listing.

(56) References Cited

U.S. PATENT DOCUMENTS

| | | | |
|---|---|---|---|
| 5,847,082 A * | 12/1998 | Rother | C07K 14/005 530/350 |
| 5,859,205 A | 1/1999 | Adair et al. | |
| 6,033,903 A * | 3/2000 | Sisk | C07K 14/723 435/320.1 |
| 6,180,370 B1 | 1/2001 | Queen et al. | |
| 6,210,671 B1 | 4/2001 | Co | |
| 6,277,375 B1 | 8/2001 | Ward | |
| 6,329,511 B1 | 12/2001 | Vasquez et al. | |
| 8,563,269 B2 * | 10/2013 | Stagliano | A61K 47/6849 435/69.1 |
| 8,664,475 B2 | 3/2014 | Puzio | |
| 2005/0137130 A1 | 6/2005 | Bodmer | |
| 2009/0042785 A1 | 2/2009 | Matschiner et al. | |
| 2009/0070897 A1 | 3/2009 | Goldman | |
| 2009/0221483 A1 | 9/2009 | Melgarejo | |
| 2010/0189651 A1 | 7/2010 | Stagliano | |
| 2010/0221212 A1 | 9/2010 | Stagliano | |
| 2011/0178279 A1 | 7/2011 | Williams | |
| 2013/0060010 A1 | 3/2013 | Williams | |
| 2014/0024810 A1 | 1/2014 | Stagliano | |
| 2014/0051645 A1 | 2/2014 | Matschiner | |
| 2014/0080177 A1 | 3/2014 | Skerra | |
| 2014/0255313 A1 | 9/2014 | Vasiljeva | |
| 2018/0215806 A1 | 8/2018 | Williams | |

FOREIGN PATENT DOCUMENTS

| | | |
|---|---|---|
| WO | W09100360 A1 | 1/1991 |
| WO | WO9200373 A1 | 1/1992 |
| WO | WO9308829 A1 | 5/1993 |
| WO | WO9605309 A3 | 3/1996 |
| WO | WO2013169338 A1 | 11/2013 |
| WO | WO2014197612 A1 | 12/2014 |

OTHER PUBLICATIONS

Arnon, R. et al. (1985). "Monoclonal Antibodies for Imrnunotargeting of Drugs in Cancer Therapy", Monoclonal Antibodies and Cancer Therapy, Reisfeld, R.A. et al. eds., Alan R. Liss, Inc., New York, New York, pp. 243-256. 17.

Au et al., "Secretory production of bioactive recombinant human granulocyte-macrophage colony-stimulating factor by a bacuiovirus expression system," J Biotechnol (1996) 51(2):107-113.

Beck et al., "Enterocolitis in Patients With Cancer After AntibodyBlockade of Cytotoxic T-Lymphocyte—Associated Antigen 4," J Olin Oncol (2006) 24(15):2283-2289.

Biniossek, M.L., et al. (2011). "Proteomic identification of protease cleavage sites characterizes prime and non-prime specificity of cysteine cathepsins B, L, and S". J Proteome Res, 10:5363-5373.

Brennen, W.N., et al. (2012), "Targeting carcinoma-associated fibroblasts within the tumor stroma with a fibroblast activation protein-activated prodrug", J Natl Cancer Inst 104:1320-1334.

Brennen, W.N., et al., (2012), "Rationale behind targeting fibroblast activation protein-expressing carcinoma-associated fibroblasts as a novel chemotherapeutic strategy". Mol Cancer Ther 11:257-266.

Charles et al., "Cloning and expression of a rat neuronal nitric oxide synthase coding sequence in a baculovirus/insect cell system," Biochem Biophys Res Commun (1993) 196(3):1481-1489.

Chonn et al., "Recent advances in liposomal drug-delivery systems," Curr Opin Biotechnol (1995) 6(6).698-708.

Cole, S.P.C. et al. (1985). "The EBC-Hybridoma Technique and its Application to Human Lung Cancer," Monoclonal Antibodies and Cancer Therapy pp. 77-96.

Curran et al., "PD-1 and CTLA-4 combination blockade expandsinfiltrating T cells and reduces regulatory T andmyeloid cells within B16 melanoma tumors," PNAS (2010) 107(9):4275-4280.

Czajkowsky et al., "Fc-fusion proteins: new developments andfuture perspectives," EMBO Mol Med (2012) 4:1015-1028 1-7.

Database UniProt [Online] Sep. 11, 2007, Database accession No. A7A322.

Denmeade, S.R., et al. (2012). "Engineering a prostate-specific membrane antigen-activated tumor endothelial cell prodrug for cancer therapy"; Sci Transl Med. Jun. 27, 2012;4(140):140ra86.

Donaldson et al., "Design and development of masked therapeutic antibodies to limit off-target effects: Application to anti-EGFR antibodies," Cancer Biol Ther (2009) 8(22):2147-2152.

Drake et al., "Androgen ablation mitigates tolerance to a prostate/prostate cancer-restricted antigen," Cancer Cell (2005) 7:239.

Eyles et al., "Oral delivery and fate of poly(lactic acid) microsphere-encapsulated interferon in rats," J Pharm Pharmacol (1997) 49(7):669-674.

Fishwild, D.M. et al. (Jul. 1996), "High-avidity Human IgGk Monoclonal Antibodies From a Novel Strain of Minilocus Transgenic Mice," Nature Biotechnol. 14:845-851.

Gao et al., "Controlled release of a contraceptive steroid from biodegradable and injectable gel formulations: in vitro evaluation," Pharm Res (1995) 12(6):857-863.

Gao, W., et al., (2006), "Exosite interactions contribute to tension-induced cleavage of von Willebrand factor by the antithrombotic ADAMTS13 metalloprotease". Proc Natl Acad Sci U S A 103:19099-19104.

Getnet et al., "Tumor Recognition and Self-Recognition induce Distinct Transcriptional Profiles in Antigen-Specific CD4 T Cells," J Immunol (2009) 182:4675-4685.

Gregor et al., "CTLA-4 blockade in combination with xenogeneic DNA vaccines enhances T-cell responses, tumor immunity and autoimmunity to self antigens in animal and cellular model systems," Vaccine (2004) 22:1700-1708.

Grosso et al., "Lag-3 regulates CD8+ T cell accumulation and effector function in murine self-and tumor-tolerance systems," J. Clin. Invest (2007) 117:3383-3392 1-7.

Hadier-Olsen, E., et al (2013), "Matrix metalloproteinases in cancer: their value as diagnostic and prognostic markers and therapeutic targets", Tumour Biol 34:2041-2051.

Hellstrom, K.E. et al. (1987). "Antibodies for Drug Delivery", Controlled Drug Delivery, Robinson, J.R. et al. eds., Marcel Dekker, Inc., New York, New York, pp. 623-653.

Henikoff and Henikoff (1989), :Amino acid substitution matrices from protein blocks, Proc. Natl. Acad, Sci. USA 89:10915-10919.

Hodge et al., "Vaccine Therapy of Established Tumors in the Absenceof Autoimmunity," Clin Can Res (2003) 9:1387-1849.

Hodi et al., "Improved Survival with ipilimumab in Patients with Metastatic Melanoma," N Engl J Med (2010) 363:711-723.

Igoucheva et al., "Immunotargeting and eradication of orthotopic melanoma using a chemokine-enhanced DNA vaccine," Gene Theapy (2013) 20:938-948.

Iwama, S., et al. (2014), "Pituitary expression of CTLA-4 mediates hypophysitis secondary to administration of CTLA-4 blocking antibody", Sci Transl Med 6:230ra245.

Jamaspishvili, T., et al., "Urine markers in monitoring for prostate cancer", Prostate Cancer Prostatic Dis. Mar. 2010;13 (1):12-19.

Jones, P.T. et al. (May 29, 1986). "Replacing the Complementarity-determining Regions in a Human Antibody With Those From a Mouse," Nature 321:522-525.

Karlin and Altschul (1993), "Applications and statistics for multiple high-scoring segments in molecular sequences"; Proc. Nati. Acad. Sci. USA 90:5873-5787.

Ke, S.H., et al., (1997), "Optimal subsite occupancy and design of a selective inhibitor of urokinase", J Biol Chem 272:20456-20462.

Kohler et al., "Continuous cultures of fused cells secreting antibody of predefined specificity," Nature (1975) 256:495-497.

Korman, A., et al., (2005). "Tumor immunotherapy: preclinical and clinical activity of anti-CTLA-4 antibodies". Current Opinion in Investigational Drugs 6:582-591.

Kozbor, D. et al. (1983). "The Production of Monoclonal Antibodies From Human Lymphocytes," lrnmunol. Today 4 (3):72-79.

Kwon et al., "Elimination of residual metastatic prostate cancerafter surgery and adjunctive cytotoxic T lymphocyte-associated antigen 4 (CTLA-4) blockade immunotherapy," PNAS (1999) 96(26):15074-15079.

Liu, Z., et al. (2014)."Legumain protease-activated TAT-liposome cargo for targeting tumours and their microenvironment". Nat Commun 5:4280.

(56) References Cited

OTHER PUBLICATIONS

Lonberg, N. et al. (1995). "Human Antibodies From Transgenic Mice," Intern. Rev. Immunol. 13:65-93.
Lonberg, N. et al. (Apr. 28, 1994). "Antigen-Specific Human Antibodies from Mice Comprising Four Distinct Genetic Modifications," Nature 368:856-859.
Marks et al., "By-passing immunization: building high affinity human antibodies by chain shuffling," Biotechnology N. Y. (1992) 10(7):779-783.
Maxwell et al., "Abatacept for rheumatoid arthritis: a Cochrane systematic review," J Rheumatol (2010) 37(2):234-245.
McCafferty et al., "Phage antibodies: filamentous phage displaying antibody variable domains," Nature (1990) 348:552-554.
Morrison et al., "Chimeric human antibody molecules: mouse antigen-binding domains with human constant region domains," PNAS (1984) 81(21):6851-6855.
Morrison et al., "Genetically engineered antibody molecules," Adv Immunol (1989) 44:65-92.
Morrison, "Immunology. Success in specification," Nature (1994) 368(6474):812-813.
Morton et al., "Differential effects of CTLA-4 substitutions on the binding of human CD80 (B7-1) and CD86 (B7-2)," J lmmunol (1996) 156(3):1047-1054.
Needleman, S. B. et al. (1970). "A General Method Applicable to the Search for Similarities in the Amino Acid sequence of Two Proteins," J. Mol. Biol. 48:444-453I.
Neuberger, M. (Jul. 1996). "Generating High-Avidity Human Mabs in Mice," Nature Biotechnol. 14:826.
Nimmerjahn, F. et al. (May 1, 2012). "Translating Basic Mechanisms of IgG Effector Activity Into Next Generation Cancer Therapies," Cancer immunity 12(1):1-7.
Ostro et al. "Use of liposomes as injectable-drug delivery systems," Am J Hosp Pharm (1989) 46(8):1579-1587.
Padlan, "A possible procedure for reducing the immunogenicity of antibody variable domains while preserving their ligand-binding properties," Mol immunol (1991) 28(4-5):489-498.
Padlan, "Anatomy of the antibody molecule," Mol Immunol (1994) 31(3):169-217.
Pearson and Lipman (1988) Proc. Nat'l. Acad. Sci. USA 85:244458.
Phan et al., "CTLA-4 Blockade with Monoclonal Antibodies in Patientswith Metastatic Cancer: Surgical Issues," Annals of Surgical Oncology (2008) 15(11):3014-3021.
Presta, "Antibody engineering," Curr Opi Struct Biol (1992) 2(4):593-59.
Quezada et al., "CTLA4 blockade and Gm-Csf combination immunotherapy alters the intratumor balance of effector and regulatory T cells," J Clin Invest (2006) 116:1935-1945.
Rao, "Recent developments of collagen-based materials for medical applications and drug delivery systems," J Biomater Sci Polym Ed (1995) 7(7):623-645.
Rieci-Mann, L. et al. (Mar. 24, 1988). "Reshaping Human Antibodies for Therapy," Nature 332:323-327.
Schonfeld et al., "An engineered lipocalin specific for CTLA-4 reveals a combining site with structural and conformationalfeatures similar to antibodies," PNAS (2009) 106(20):8198-8203.
Simmons et al., "Local secretion of anti-CTLA-4 enhances the therapeutic eYcacy of a cancer immunotherapy with reduced evidence of systemic autoimmunity," Cancer irnrnunol Immunother (2008) 57:1263-1270.

Singh, P., et al., (2009). "Molecular insights into substrate specificity of prostate specific antigen through structural modeling". Proteins 77:984-993.
Suresh et al., "Bispecific monoclonal antibodies from hybrid hybridomas," Methods in Enzymology (1986) 121:210-228.
Thorpe et al., "The Preparation and Cytotoxic Properties of Antibody-Toxin Conjugates," Immunol Rev (1982) 62:119-158.
Traunecker et al., "Bispecific single chain molecules (Janusins) target cytotoxic lymphocytes on Hiv infected cells," EMBO j. (1991) 10(12):3655-3659.
Turk et al., "Determination of protease cleavage site motifs using mixture-based oriented peptide libraries," Nat Biotechnol (2001) 19(7):661-667.
Verhoeyen et al., "Reshaping human antibodies: grafting an antilysozyme activity," Science (1988) 239 (4847):1534-1536.
Vidarsson G et al. (2014). "IgG subclasses and allotypes: from structure to effector functions". Front Immunol. ;5:520.
Waitz et al., "Potent induction of tumor immunity by combining tumor cryoablation with anti-CTLA-4 therapy," Cancer Res (2012) 72(2):430-439.
Waldman, "Annual Progress Report: 2009 Nonformula Grant on Cancer," Vaccines (2011) 1-9.
Weber et al., "Phase 1/11 Study of Ipilimumab for Patients WithMetastatic Melanoma," J Clin Oncol (2008) 26 (36):5950-5956.
Winter et al., "Man-made antibodies," Nature (1991) 349:293-299.
Wolchok, J.D., et al. (2013). "Nivolumab plus Ipilimumab in Advanced Melanoma". N Engl J Med. Jul. 11, 2013;369 (2):122-33.
Xu et al., "Affinity and cross-reactivity engineering of CTLA4-Ig to modulate T cell costirnulation," J Immunol (2012) 189 (9).4470-4477.
Zhang et al., "Loss of Keap1 Function in Prostate Cancer Cells Causes Chemoand Radio-resistance and Promotes Tumor Growth," Mol Cancer Ther (2010) 9(2):336.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology (1990) 111:2129-2138.
Jones et al., "Critically assessing the state-of-the-art in protein structure prediction," Pharmacogenomincs Journal (2001) 1:126-134.
Lazar et al., "Transforming growth factor alpha: mutation of aspartic acid 47 and leucine 48 results in different biological activities," Molecular and Cellular Biology (1988) 8:1247-1252.
Rudikoff et al., "Single amino acid substitution altering antigen-binding specificity," Proc Natl Acad Sci USA (1982) 79:1979.
Skolnick et al., "From genes to protein structure and function: novel applications of computational approaches in the genomic era," Trends in Biotechnology (2000) 18:34-39.
Tosatto et al., "Large-scale prediction of protein structure and function from sequence," Current Pharmaceutical Design (2006) 12:2067-2086.
Wu et al., "Humanization of a Murine Monoclonal Antibody by simultaneous optimization of framework and CDR residues," J Mol Biol (1999) 294:151-162.

* cited by examiner

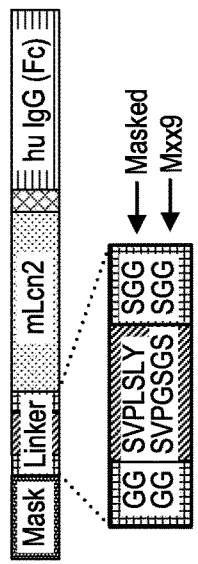
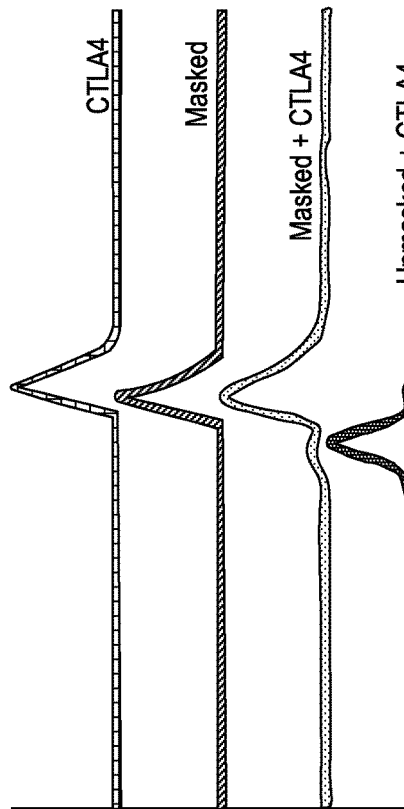
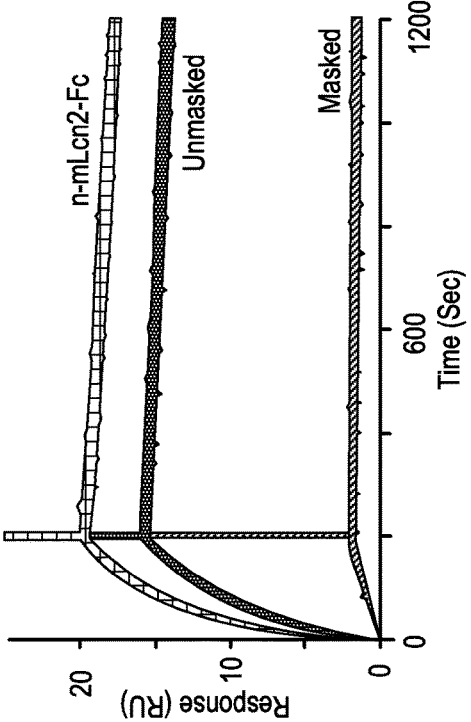
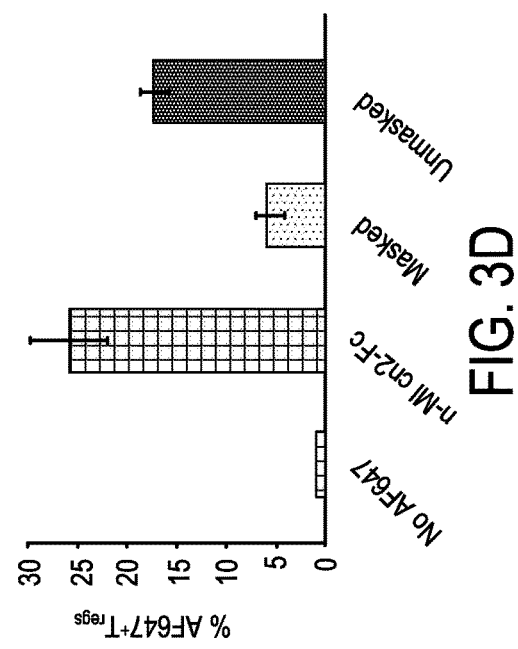
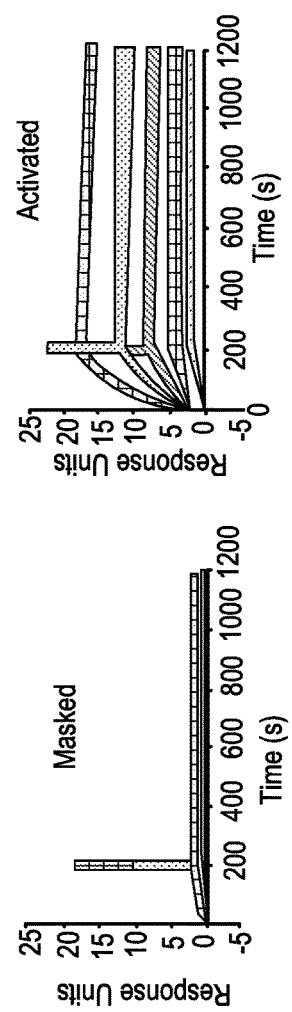
FIG. 3A
FIG. 3B
FIG. 3C
FIG. 3D

| | |
|---|---|
| Original | GGSVPLSLYSGG |
| V1 | GGSGGSVPLSLY |
| V2 | GGSGGSVPLSLYSGG |
| V3 | SGGGSGGGSVPLSLYSGG |
| V4 | SGGGSGGGSVPLSLYSGGSGG |

SEQUENCE LISTING

```
<160> NUMBER OF SEQ ID NOS: 63

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Cys Tyr Gly Leu Gly Phe Asn Phe Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 2

Cys Arg Ile Asp Glu Arg Leu Gln Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 3

Cys Phe Thr Pro Trp Pro Glu Ala Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence
```

```
<400> SEQUENCE: 4

Cys Trp Pro Glu Trp Asp Leu Trp Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 5

Cys Glu Lys Trp Phe Arg Phe Met Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 6

Cys Tyr Leu Glu Leu Met His Ser Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Cys Val Thr Gly Phe Glu Phe Leu Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Cys Pro Arg Pro Leu Tyr Trp Leu Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 9

Cys Ser Val Leu Pro Pro Phe Met Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Sequence
```

<400> SEQUENCE: 10

Cys Asn Asn Tyr Lys Gly Gly Arg Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 11

Cys Leu Pro Glu Ile Ser Phe Leu Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 12

Cys Trp Ser Pro Leu Pro Phe Met Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 13

Cys Ser Val Leu Leu Pro Phe Met Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 14

Cys Phe His Ala Pro Trp Ala Pro Cys
1               5

<210> SEQ ID NO 15
<211> LENGTH: 1503
<212> TYPE: DNA
<213> ORGANISM: Homo sapiens

<400> SEQUENCE: 15

```
atgctactag taaatcagtc acaccaaggc ttcaataagg aacacacaag caagatggta      60
agcgctattg ttttatatgt gcttttggcg gcggcggcgc attctgcctt tgcggcggga     120
tcctgttacg gattaggttt caacttctgt ggcggtagtg tcccgctgtc gctgtatagt     180
ggatcccagg actctaccag cgacctgatc cccgcaccac cgctgtctaa ggtgccactg     240 cagcaaaaact tccaggacaa tcaatttcac ggtaaatggt acgtggtcgg cctggctgga     300
aaccgtatcc tgcgcgacga tcagcatcct atgaatatgt acgcgactat ttatgaactg     360
aaggaagaca aaagctacaa cgttacctcc gtgatctctt cacacaagaa atgcgaatat     420
```

```
acgattgcca ccttcgtgcc gggaagccag cctggcgagt ttaccctggg caatatcaag      480
tcttacggag acaaaacctc atatctggtg cgcgttgtgt ccactgatta caaccaatat      540
gcagtcgttt tctttaagct ggcggaagat aatgcagagt tctttgccat caccatttat      600
ggccgtacta aggagctggc cagcgaactg aaagagaact tcattcgctt tagtaaatcg      660
ctgggcctgc cagagaatca cattgttttc cctgtcccca ttgaccagtg tattgacggc      720
tctagatcag gtggcacctc aggtggcggt agtgtcccgg ggtcggggtc tagtggttcg      780
accagcggct ccggtaaaag ctccgagggc agcggccaag cttcgaccca tacctgccca      840
ccatgtccag ctcctgaact gctgggtggt ccaagcgtgt tcctgtttcc gcctaagcct      900
aaagacaccc tgatgatcag ccgtacccca gaggtcacct gcgtggtcgt tgacgtttcc      960
cacgaagatc cagaggtcaa gttcaactgg tacgtggatg gcgttgaagt gcataatgct     1020
aagaccaaac cccgtgaaga gcagtacaac tctacctatc gcgtggtctc agtcctgacc     1080
gttctgcacc aggactggct gaacggcaaa gagtataagt gcaaagtctc taataaggcg     1140
ctgcccgcac aatcgaaaaa aaccatttca aggcgaaggg tcagccccg tgagccacag     1200 gtttacaccc tgcccccaag tcgcgacgaa ctgaccaaga accaggtgtc gctgacctgt     1260
ctggtcaaag cttctatcc gtctgatatt gcagtggaat gggagtcaaa tggtcagcct     1320
gagaacaatt acaagaccac cccgcctgtt ctggactccg atggctcttt ctttctgtat     1380
agcaagctga ccgtggataa atcccgctgg cagcagggta acgtgttcag ctgctcagtg     1440
atgcatgaag ccctgcacaa tcattacacc cagaagagtc tgtcgctgag cccgggtaaa     1500
taa                                                                  1503
```

<210> SEQ ID NO 16
<211> LENGTH: 500
<212> TYPE: PRT
<213> ORGANISM: Homo sapiens

<400> SEQUENCE: 16

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Gly Ser Cys Tyr Gly Leu Gly Phe Asn
        35                  40                  45

Phe Cys Gly Gly Ser Val Pro Leu Ser Leu Tyr Ser Gly Ser Gln Asp
    50                  55                  60

Ser Thr Ser Asp Leu Ile Pro Ala Pro Pro Leu Ser Lys Val Pro Leu
65                  70                  75                  80

Gln Gln Asn Phe Gln Asp Asn Gln Phe His Gly Lys Trp Tyr Val Val
                85                  90                  95

Gly Leu Ala Gly Asn Arg Ile Leu Arg Asp Asp Gln His Pro Met Asn
            100                 105                 110

Met Tyr Ala Thr Ile Tyr Glu Leu Lys Glu Asp Lys Ser Tyr Asn Val
        115                 120                 125

Thr Ser Val Ile Ser Ser His Lys Lys Cys Glu Tyr Thr Ile Ala Thr
    130                 135                 140

Phe Val Pro Gly Ser Gln Pro Gly Glu Phe Thr Leu Gly Asn Ile Lys
145                 150                 155                 160

Ser Tyr Gly Asp Lys Thr Ser Tyr Leu Val Arg Val Val Ser Thr Asp
                165                 170                 175
```

```
Tyr Asn Gln Tyr Ala Val Val Phe Phe Lys Leu Ala Glu Asp Asn Ala
                180                 185                 190

Glu Phe Phe Ala Ile Thr Ile Tyr Gly Arg Thr Lys Glu Leu Ala Ser
            195                 200                 205

Glu Leu Lys Glu Asn Phe Ile Arg Phe Ser Lys Ser Leu Gly Leu Pro
        210                 215                 220

Glu Asn His Ile Val Phe Pro Val Pro Ile Asp Gln Cys Ile Asp Gly
225                 230                 235                 240

Ser Arg Ser Gly Gly Thr Ser Gly Gly Ser Val Pro Gly Ser Gly
                245                 250                 255

Ser Ser Gly Ser Thr Ser Gly Ser Gly Lys Ser Ser Glu Gly Ser Gly
                260                 265                 270

Gln Ala Ser Thr His Thr Cys Pro Pro Cys Pro Ala Pro Glu Leu Leu
                275                 280                 285

Gly Gly Pro Ser Val Phe Leu Phe Pro Pro Lys Pro Lys Asp Thr Leu
            290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500

<210> SEQ ID NO 17
<211> LENGTH: 462
<212> TYPE: PRT
<213> ORGANISM: Homo sapiens

<400> SEQUENCE: 17

Ala Gly Ser Cys Tyr Gly Leu Gly Phe Asn Phe Cys Gly Gly Ser Val
1               5                   10                  15

Pro Leu Ser Leu Tyr Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
        35                  40                  45
```

-continued

Asn Gln Phe His Gly Lys Trp Tyr Val Val Gly Leu Ala Gly Asn Arg
 50                  55                  60
Ile Leu Arg Asp Asp Gln His Pro Met Asn Met Tyr Ala Thr Ile Tyr
65                  70                  75                  80
Glu Leu Lys Glu Asp Lys Ser Tyr Asn Val Thr Ser Val Ile Ser Ser
                85                  90                  95
His Lys Lys Cys Glu Tyr Thr Ile Ala Thr Phe Val Pro Gly Ser Gln
            100                 105                 110
Pro Gly Glu Phe Thr Leu Gly Asn Ile Lys Ser Tyr Gly Asp Lys Thr
        115                 120                 125
Ser Tyr Leu Val Arg Val Ser Thr Asp Tyr Asn Gln Tyr Ala Val
    130                 135                 140
Val Phe Phe Lys Leu Ala Glu Asp Asn Ala Glu Phe Phe Ala Ile Thr
145                 150                 155                 160
Ile Tyr Gly Arg Thr Lys Glu Leu Ala Ser Glu Leu Lys Glu Asn Phe
                165                 170                 175
Ile Arg Phe Ser Lys Ser Leu Gly Leu Pro Glu Asn His Ile Val Phe
            180                 185                 190
Pro Val Pro Ile Asp Gln Cys Ile Asp Gly Ser Arg Ser Gly Gly Thr
        195                 200                 205
Ser Gly Gly Gly Ser Val Pro Gly Ser Gly Ser Ser Gly Ser Thr Ser
    210                 215                 220
Gly Ser Gly Lys Ser Ser Glu Gly Ser Gly Gln Ala Ser Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 18
<211> LENGTH: 462
<212> TYPE: PRT
<213> ORGANISM: Homo sapiens

<400> SEQUENCE: 18

```
Ala Gly Ser Cys Arg Ile Asp Glu Thr Leu Gln Cys Gly Gly Ser Val
 1               5                  10                  15

Pro Leu Ser Leu Tyr Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
        35                  40                  45

Asn Gln Phe His Gly Lys Trp Tyr Val Val Gly Leu Ala Gly Asn Arg
    50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr
        115                 120                 125

Ser Tyr Leu Val Arg Val Val Ser Thr Asp Tyr Asn Gln Tyr Ala Val
    130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
        195                 200                 205

Ser Gly Gly Gly Ser Val Pro Gly Ser Gly Ser Gly Ser Thr Ser
    210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380
```

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
450                 455                 460

<210> SEQ ID NO 19
<211> LENGTH: 462
<212> TYPE: PRT
<213> ORGANISM: Homo sapiens

<400> SEQUENCE: 19

Ala Gly Ser Cys Trp Pro Glu Trp Asp Leu Trp Cys Gly Gly Ser Val
1               5                   10                  15

Pro Leu Ser Leu Tyr Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
            35                  40                  45

Asn Gln Phe His Gly Lys Trp Tyr Val Val Gly Leu Ala Gly Asn Arg
    50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr
            115                 120                 125

Ser Tyr Leu Val Arg Val Val Ser Thr Asp Tyr Asn Gln Tyr Ala Val
130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
            195                 200                 205

Ser Gly Gly Gly Ser Val Pro Gly Ser Gly Ser Gly Ser Thr Ser
210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr

```
            290             295             300
Lys Pro Arg Glu Glu Gln Tyr Asn Ser Thr Tyr Arg Val Val Ser Val
305             310             315             320

Leu Thr Val Leu His Gln Asp Trp Leu Asn Gly Lys Glu Tyr Lys Cys
            325             330             335

Lys Val Ser Asn Lys Ala Leu Pro Ala Pro Ile Glu Lys Thr Ile Ser
            340             345             350

Lys Ala Lys Gly Gln Pro Arg Glu Pro Gln Val Tyr Thr Leu Pro Pro
            355             360             365

Ser Arg Asp Glu Leu Thr Lys Asn Gln Val Ser Leu Thr Cys Leu Val
            370             375             380

Lys Gly Phe Tyr Pro Ser Asp Ile Ala Val Glu Trp Glu Ser Asn Gly
385             390             395             400

Gln Pro Glu Asn Asn Tyr Lys Thr Thr Pro Pro Val Leu Asp Ser Asp
            405             410             415

Gly Ser Phe Phe Leu Tyr Ser Lys Leu Thr Val Asp Lys Ser Arg Trp
            420             425             430

Gln Gln Gly Asn Val Phe Ser Cys Ser Val Met His Glu Ala Leu His
            435             440             445

Asn His Tyr Thr Gln Lys Ser Leu Ser Leu Ser Pro Gly Lys
450             455             460
```

```
<210> SEQ ID NO 20
<211> LENGTH: 462
<212> TYPE: PRT
<213> ORGANISM: Homo sapiens

<400> SEQUENCE: 20

Ala Gly Ser Cys Ser Val Leu Pro Pro Phe Met Cys Gly Gly Ser Val
1               5                   10                  15

Pro Leu Ser Leu Tyr Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
        35                  40                  45

Asn Gln Phe His Gly Lys Trp Tyr Val Val Gly Leu Ala Gly Asn Arg
    50                  55                  60

Ile Leu Arg Asp Asp Gln His Pro Met Asn Met Tyr Ala Thr Ile Tyr
65              70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr
        115                 120                 125

Ser Tyr Leu Val Arg Val Val Ser Thr Asp Tyr Asn Gln Tyr Ala Val
    130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
        195                 200                 205
```

```
Ser Gly Gly Gly Ser Val Pro Gly Ser Gly Ser Gly Ser Thr Ser
    210             215             220
Gly Ser Gly Lys Ser Ser Glu Gly Ser Gly Gln Ala Ser Thr His Thr
225             230             235             240
Cys Pro Pro Cys Pro Ala Pro Glu Leu Leu Gly Gly Pro Ser Val Phe
                245             250             255
Leu Phe Pro Pro Lys Pro Lys Asp Thr Leu Met Ile Ser Arg Thr Pro
            260             265             270
Glu Val Thr Cys Val Val Val Asp Val Ser His Glu Asp Pro Glu Val
        275             280             285
Lys Phe Asn Trp Tyr Val Asp Gly Val Glu Val His Asn Ala Lys Thr
    290             295             300
Lys Pro Arg Glu Glu Gln Tyr Asn Ser Thr Tyr Arg Val Val Ser Val
305             310             315             320
Leu Thr Val Leu His Gln Asp Trp Leu Asn Gly Lys Glu Tyr Lys Cys
                325             330             335
Lys Val Ser Asn Lys Ala Leu Pro Ala Pro Ile Glu Lys Thr Ile Ser
            340             345             350
Lys Ala Lys Gly Gln Pro Arg Glu Pro Gln Val Tyr Thr Leu Pro Pro
        355             360             365
Ser Arg Asp Glu Leu Thr Lys Asn Gln Val Ser Leu Thr Cys Leu Val
    370             375             380
Lys Gly Phe Tyr Pro Ser Asp Ile Ala Val Glu Trp Glu Ser Asn Gly
385             390             395             400
Gln Pro Glu Asn Asn Tyr Lys Thr Thr Pro Pro Val Leu Asp Ser Asp
                405             410             415
Gly Ser Phe Phe Leu Tyr Ser Lys Leu Thr Val Asp Lys Ser Arg Trp
            420             425             430
Gln Gln Gly Asn Val Phe Ser Cys Ser Val Met His Glu Ala Leu His
        435             440             445
Asn His Tyr Thr Gln Lys Ser Leu Ser Leu Ser Pro Gly Lys
    450             455             460

<210> SEQ ID NO 21
<211> LENGTH: 462
<212> TYPE: PRT
<213> ORGANISM: Homo sapiens

<400> SEQUENCE: 21

Ala Gly Ser Cys Trp Ser Pro Leu Pro Phe Met Cys Gly Gly Ser Val
1               5                   10                  15
Pro Leu Ser Leu Tyr Ser Gly Ser Gln Asp Ser Thr Ser Asp Leu Ile
            20                  25                  30
Pro Ala Pro Pro Leu Ser Lys Val Pro Leu Gln Gln Asn Phe Gln Asp
        35                  40                  45
Asn Gln Phe His Gly Lys Trp Tyr Val Val Gly Leu Ala Gly Asn Arg
    50                  55                  60
Ile Leu Arg Asp Asp Gln His Pro Met Asn Met Tyr Ala Thr Ile Tyr
65                  70                  75                  80
Glu Leu Lys Glu Asp Lys Ser Tyr Asn Val Thr Ser Val Ile Ser Ser
                85                  90                  95
His Lys Lys Cys Glu Tyr Thr Ile Ala Thr Phe Val Pro Gly Ser Gln
            100                 105                 110
Pro Gly Glu Phe Thr Leu Gly Asn Ile Lys Ser Tyr Gly Asp Lys Thr
        115                 120                 125
```

```
Ser Tyr Leu Val Arg Val Val Ser Thr Asp Tyr Asn Gln Tyr Ala Val
        130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
        195                 200                 205

Ser Gly Gly Gly Ser Val Pro Gly Ser Gly Ser Ser Gly Ser Thr Ser
210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 22
<211> LENGTH: 462
<212> TYPE: PRT
<213> ORGANISM: Homo sapiens

<400> SEQUENCE: 22

Ala Gly Ser Cys Trp Ser Pro Leu Pro Phe Met Cys Gly Gly Ser Val
1               5                   10                  15

Pro Gly Ser Gly Ser Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
```

```
                35                  40                  45
Asn Gln Phe His Gly Lys Trp Tyr Val Val Gly Leu Ala Gly Asn Arg
 50                  55                  60

Ile Leu Arg Asp Asp Gln His Pro Met Asn Met Tyr Ala Thr Ile Tyr
65                   70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr
        115                 120                 125

Ser Tyr Leu Val Arg Val Ser Thr Asp Tyr Asn Gln Tyr Ala Val
    130                 135                 140

Val Phe Phe Lys Leu Ala Glu Asp Asn Ala Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
        195                 200                 205

Ser Gly Gly Gly Ser Val Pro Gly Ser Gly Ser Ser Gly Ser Thr Ser
    210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 23
<211> LENGTH: 462
<212> TYPE: PRT
<213> ORGANISM: Homo sapiens

<400> SEQUENCE: 23

```
Ala Gly Ser Cys Trp Ser Pro Leu Pro Phe Met Cys Gly Ser Leu Ser
1               5                   10                  15

Gly Arg Ser Asp Asn His Gly Ser Gln Asp Ser Thr Ser Asp Leu Ile
                20                  25                  30

Pro Ala Pro Leu Ser Lys Val Pro Leu Gln Gln Asn Phe Gln Asp
        35                  40                  45

Asn Gln Phe His Gly Lys Trp Tyr Val Val Gly Leu Ala Gly Asn Arg
    50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
                100                 105                 110

Pro Gly Glu Phe Thr Leu Gly Asn Ile Lys Ser Tyr Gly Asp Lys Thr
            115                 120                 125

Ser Tyr Leu Val Arg Val Val Ser Thr Asp Tyr Asn Gln Tyr Ala Val
    130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
                180                 185                 190

Pro Val Pro Ile Asp Gln Cys Ile Asp Gly Ser Arg Ser Gly Gly Thr
            195                 200                 205

Ser Gly Gly Gly Ser Val Pro Gly Ser Gly Ser Ser Gly Ser Thr Ser
    210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
```

```
                    370               375               380
Lys Gly Phe Tyr Pro Ser Asp Ile Ala Val Glu Trp Glu Ser Asn Gly
385                 390               395                 400

Gln Pro Glu Asn Asn Tyr Lys Thr Thr Pro Val Leu Asp Ser Asp
                    405               410                 415

Gly Ser Phe Phe Leu Tyr Ser Lys Leu Thr Val Asp Lys Ser Arg Trp
                420               425               430

Gln Gln Gly Asn Val Phe Ser Cys Ser Val Met His Glu Ala Leu His
                435               440               445

Asn His Tyr Thr Gln Lys Ser Leu Ser Leu Ser Pro Gly Lys
                450               455               460

<210> SEQ ID NO 24
<211> LENGTH: 462
<212> TYPE: PRT
<213> ORGANISM: Homo sapiens

<400> SEQUENCE: 24

Ala Gly Ser Cys Trp Ser Pro Leu Pro Phe Met Cys Gly Gly Ser His
1               5                   10                  15

Ser Ser Lys Leu Gln Leu Gly Ser Gln Asp Ser Thr Ser Asp Leu Ile
                20                  25                  30

Pro Ala Pro Leu Ser Lys Val Pro Leu Gln Gln Asn Phe Gln Asp
                35                  40                  45

Asn Gln Phe His Gly Lys Trp Tyr Val Gly Leu Ala Gly Asn Arg
    50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
                100                 105                 110

Pro Gly Glu Phe Thr Leu Gly Asn Ile Lys Ser Tyr Gly Asp Lys Thr
                115                 120                 125

Ser Tyr Leu Val Arg Val Val Ser Thr Asp Tyr Asn Gln Tyr Ala Val
                130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
                180                 185                 190

Pro Val Pro Ile Asp Gln Cys Ile Asp Gly Ser Arg Ser Gly Gly Thr
                195                 200                 205

Ser Gly Gly Gly Ser Val Pro Gly Ser Gly Ser Gly Ser Thr Ser
                210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285
```

```
Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 25
<211> LENGTH: 462
<212> TYPE: PRT
<213> ORGANISM: Homo sapiens

<400> SEQUENCE: 25

Ala Gly Ser Cys Trp Ser Pro Leu Pro Phe Met Cys Gly Ser Pro Leu
1               5                   10                  15

Ala Gln Ala Val Arg Ser Gly Ser Gln Asp Ser Thr Ser Asp Leu Ile
            20                  25                  30

Pro Ala Pro Pro Leu Ser Lys Val Pro Leu Gln Gln Asn Phe Gln Asp
        35                  40                  45

Asn Gln Phe His Gly Lys Trp Tyr Val Val Gly Leu Ala Gly Asn Arg
50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr
        115                 120                 125

Ser Tyr Leu Val Arg Val Val Ser Thr Asp Tyr Asn Gln Tyr Ala Val
    130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
            180                 185                 190

Pro Val Pro Ile Asp Gln Cys Ile Asp Gly Ser Arg Ser Gly Gly Thr
        195                 200                 205
```

Ser Gly Gly Gly Ser Val Pro Gly Ser Gly Ser Gly Ser Thr Ser
210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 26
<211> LENGTH: 462
<212> TYPE: PRT
<213> ORGANISM: Homo sapiens

<400> SEQUENCE: 26

Ala Gly Ser Cys Trp Ser Pro Leu Pro Phe Met Cys Gly Gly Ser Gly
1               5                   10                  15

Pro Leu Gly Met Arg Gly Gly Ser Gln Asp Ser Thr Ser Asp Leu Ile
            20                  25                  30

Pro Ala Pro Pro Leu Ser Lys Val Pro Leu Gln Gln Asn Phe Gln Asp
        35                  40                  45

Asn Gln Phe His Gly Lys Trp Tyr Val Val Gly Leu Ala Gly Asn Arg
    50                  55                  60

Ile Leu Arg Asp Asp Gln His Pro Met Asn Met Tyr Ala Thr Ile Tyr
65                  70                  75                  80

Glu Leu Lys Glu Asp Lys Ser Tyr Asn Val Thr Ser Val Ile Ser Ser
                85                  90                  95

His Lys Lys Cys Glu Tyr Thr Ile Ala Thr Phe Val Pro Gly Ser Gln
            100                 105                 110

Pro Gly Glu Phe Thr Leu Gly Asn Ile Lys Ser Tyr Gly Asp Lys Thr

```
            115                 120                 125
Ser Tyr Leu Val Arg Val Ser Thr Asp Tyr Asn Gln Tyr Ala Val
130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                165                 170                 175

Ile Arg Phe Ser Lys Ser Leu Gly Leu Pro Glu Asn His Ile Val Phe
                180                 185                 190

Pro Val Pro Ile Asp Gln Cys Ile Asp Gly Ser Arg Ser Gly Gly Thr
            195                 200                 205

Ser Gly Gly Gly Ser Val Pro Gly Ser Gly Ser Gly Ser Thr Ser
210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 27
<211> LENGTH: 462
<212> TYPE: PRT
<213> ORGANISM: Homo sapiens

<400> SEQUENCE: 27

Ala Gly Ser Cys Trp Ser Pro Leu Pro Phe Met Cys Gly Gly Ser Asn
1               5                   10                  15

Leu Ala Tyr Thr Ala Gly Ser Gln Asp Ser Thr Ser Asp Leu Ile
            20                  25                  30
```

```
Pro Ala Pro Pro Leu Ser Lys Val Pro Leu Gln Gln Asn Phe Gln Asp
         35                  40                  45

Asn Gln Phe His Gly Lys Trp Tyr Val Val Gly Leu Ala Gly Asn Arg
 50                  55                  60

Ile Leu Arg Asp Asp Gln His Pro Met Asn Met Tyr Ala Thr Ile Tyr
 65                  70                  75                  80

Glu Leu Lys Glu Asp Lys Ser Tyr Asn Val Thr Ser Val Ile Ser Ser
                 85                  90                  95

His Lys Lys Cys Glu Tyr Thr Ile Ala Thr Phe Val Pro Gly Ser Gln
             100                 105                 110

Pro Gly Glu Phe Thr Leu Gly Asn Ile Lys Ser Tyr Gly Asp Lys Thr
         115                 120                 125

Ser Tyr Leu Val Arg Val Val Ser Thr Asp Tyr Asn Gln Tyr Ala Val
     130                 135                 140

Val Phe Phe Lys Leu Ala Glu Asp Asn Ala Glu Phe Phe Ala Ile Thr
145                 150                 155                 160

Ile Tyr Gly Arg Thr Lys Glu Leu Ala Ser Glu Leu Lys Glu Asn Phe
                 165                 170                 175

Ile Arg Phe Ser Lys Ser Leu Gly Leu Pro Glu Asn His Ile Val Phe
             180                 185                 190

Pro Val Pro Ile Asp Gln Cys Ile Asp Gly Ser Arg Ser Gly Gly Thr
         195                 200                 205

Ser Gly Gly Ser Val Pro Gly Ser Gly Ser Ser Gly Ser Thr Ser
     210                 215                 220

Gly Ser Gly Lys Ser Ser Glu Gly Ser Gly Gln Ala Ser Thr His Thr
225                 230                 235                 240

Cys Pro Pro Cys Pro Ala Pro Glu Leu Leu Gly Gly Pro Ser Val Phe
                 245                 250                 255

Leu Phe Pro Pro Lys Pro Lys Asp Thr Leu Met Ile Ser Arg Thr Pro
             260                 265                 270

Glu Val Thr Cys Val Val Val Asp Val Ser His Glu Asp Pro Glu Val
         275                 280                 285

Lys Phe Asn Trp Tyr Val Asp Gly Val Glu Val His Asn Ala Lys Thr
     290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                 325                 330                 335

Lys Val Ser Asn Lys Ala Leu Pro Ala Pro Ile Glu Lys Thr Ile Ser
             340                 345                 350

Lys Ala Lys Gly Gln Pro Arg Glu Pro Gln Val Tyr Thr Leu Pro Pro
         355                 360                 365

Ser Arg Asp Glu Leu Thr Lys Asn Gln Val Ser Leu Thr Cys Leu Val
     370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                 405                 410                 415

Gly Ser Phe Phe Leu Tyr Ser Lys Leu Thr Val Asp Lys Ser Arg Trp
             420                 425                 430

Gln Gln Gly Asn Val Phe Ser Cys Ser Val Met His Glu Ala Leu His
         435                 440                 445

Asn His Tyr Thr Gln Lys Ser Leu Ser Leu Ser Pro Gly Lys
```

```
                450                 455                 460

<210> SEQ ID NO 28
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 28

His Ser Ser Lys Leu Gln
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 29

Asp Glu Glu Glu Glu
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Ala Ala Asn Xaa
1

<210> SEQ ID NO 31
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 31

Ser Gly Arg Ser Ala
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 32

Gly Phe Leu Gly
1

<210> SEQ ID NO 33
<211> LENGTH: 8
<212> TYPE: PRT
<213> ORGANISM: Artificial Sequence
<220> FEATURE:
<223> OTHER INFORMATION: Synthetic Sequence
```

<400> SEQUENCE: 33

Ala Ser Gly Pro Ala Gly Pro Ala
1               5

<210> SEQ ID NO 34
<211> LENGTH: 178
<212> TYPE: PRT
<213> ORGANISM: Homo sapiens

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
        115                 120                 125

Asn Ala Glu Phe Phe Ala Ile Thr Ile Tyr Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 35
<211> LENGTH: 37
<212> TYPE: PRT
<213> ORGANISM: Homo sapiens

<400> SEQUENCE: 35

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe
        35

<210> SEQ ID NO 36
<211> LENGTH: 1503
<212> TYPE: DNA
<213> ORGANISM: Homo sapiens

<400> SEQUENCE: 36
atgctactag taaatcagtc acaccaaggc ttcaataagg aacacacaag caagatggta      60
agcgctattg tttatatgt gcttttggcg gcggcggcgc attctgcctt tgcgcgggga     120
tcctgttgga gtccattacc cttcatgtgt ggcggtagtg tcccgctgtc gctgtatagt     180

-continued

```
ggatcccagg actctaccag cgacctgatc cccgcaccac cgctgtctaa ggtgccactg    240
cagcaaaact tccaggacaa tcaatttcac ggtaaatggt acgtggtcgg cctggctgga    300
aaccgtatcc tgcgcgacga tcagcatcct atgaatatgt acgcgactat ttatgaactg    360
aaggaagaca aaagctacaa cgttacctcc gtgatctctt cacacaagaa atgcgaatat    420
acgattgcca ccttcgtgcc gggaagccag cctggcgagt ttaccctggg caatatcaag    480
tcttacggag acaaaacctc atatctggtg cgcgttgtgt ccactgatta caaccaatat    540
gcagtcgttt tctttaagct ggcggaagat aatgcagagt tctttgccat caccatttat    600
ggccgtacta aggagctggc cagcgaactg aaagagaact tcattcgctt tagtaaatcg    660
ctgggcctgc agagaatca cattgttttc cctgtcccca ttgaccagtg tattgacggc     720
tctagatcag gtggcacctc aggtggcggt agtgtcccgg ggtcgggtc tagtggttcg     780 accagcggct ccggtaaaag ctccgagggc agcggccaag cttcgaccca tacctgccca    840
ccatgtccag ctcctgaact gctgggtggt ccaagcgtgt tcctgtttcc gcctaagcct    900
aaagacaccc tgatgatcag ccgtaccccca gaggtcacct cgctggtcgt tgacgtttcc    960
cacgaagatc cagaggtcaa gttcaactgg tacgtggatg gcgttgaagt gcataatgct   1020
aagaccaaac cccgtgaaga gcagtacaac tctacctatc gcgtggtctc agtcctgacc   1080
gttctgcacc aggactggct gaacggcaaa gagtataagt gcaaagtctc taataaggcg   1140
ctgcccgcac caatcgaaaa aaccatttca aggcgaagg gtcagccccg tgagccacag   1200
gtttacaccc tgccccaag tcgcgacgaa ctgaccaaga accaggtgtc gctgacctgt   1260
ctggtcaaag cttctatcc gtctgatatt gcagtggaat gggagtcaaa tggtcagcct   1320
gagaacaatt acaagaccac cccgcctgtt ctggactccg atggctcttt ctttctgtat   1380
agcaagctga ccgtggataa atcccgctgg cagcagggta acgtgttcag ctgctcagtg   1440
atgcatgaag ccctgcacaa tcattacacc cagaagagtc tgtcgctgag cccgggtaaa   1500
taa                                                                  1503
```

<210> SEQ ID NO 37
<211> LENGTH: 500
<212> TYPE: PRT
<213> ORGANISM: Homo sapiens

<400> SEQUENCE: 37

```
Met Leu Leu Val Asn Gln Ser His Gln Gly Phe Asn Lys Glu His Thr
  1               5                  10                  15

Ser Lys Met Val Ser Ala Ile Val Leu Tyr Val Leu Leu Ala Ala Ala
             20                  25                  30

Ala His Ser Ala Phe Ala Arg Gly Ser Cys Trp Ser Pro Leu Pro Phe
         35                  40                  45

Met Cys Gly Gly Ser Val Pro Leu Ser Leu Tyr Ser Gly Ser Gln Asp
     50                  55                  60

Ser Thr Ser Asp Leu Ile Pro Ala Pro Pro Leu Ser Lys Val Pro Leu
 65                  70                  75                  80

Gln Gln Asn Phe Gln Asp Asn Gln Phe His Gly Lys Trp Tyr Val Val
                 85                  90                  95

Gly Leu Ala Gly Asn Arg Ile Leu Arg Asp Asp Gln His Pro Met Asn
            100                 105                 110

Met Tyr Ala Thr Ile Tyr Glu Leu Lys Glu Asp Lys Ser Tyr Asn Val
        115                 120                 125

Thr Ser Val Ile Ser Ser His Lys Lys Cys Glu Tyr Thr Ile Ala Thr
```

```
                    130                 135                 140
        Phe Val Pro Gly Ser Gln Pro Gly Glu Phe Thr Leu Gly Asn Ile Lys
        145                 150                 155                 160

Ser Tyr Gly Asp Lys Thr Ser Tyr Leu Val Arg Val Ser Thr Asp
                        165                 170                 175

Tyr Asn Gln Tyr Ala Val Phe Phe Lys Leu Ala Glu Asp Asn Ala
                        180                 185                 190

Glu Phe Phe Ala Ile Thr Ile Tyr Gly Arg Thr Lys Glu Leu Ala Ser
                        195                 200                 205

Glu Leu Lys Glu Asn Phe Ile Arg Phe Ser Lys Ser Leu Gly Leu Pro
        210                 215                 220

Glu Asn His Ile Val Phe Pro Val Pro Ile Asp Gln Cys Ile Asp Gly
        225                 230                 235                 240

Ser Arg Ser Gly Gly Thr Ser Gly Gly Ser Val Pro Gly Ser Gly
                        245                 250                 255

Ser Ser Gly Ser Thr Ser Gly Ser Gly Lys Ser Ser Glu Gly Ser Gly
                        260                 265                 270

Gln Ala Ser Thr His Thr Cys Pro Pro Cys Pro Ala Pro Glu Leu Leu
                        275                 280                 285

Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Val Asp Val Ser
        305                 310                 315                 320

His Glu Asp Pro Glu Val Lys Phe Asn Trp Tyr Val Asp Gly Val Glu
                        325                 330                 335

Val His Asn Ala Lys Thr Lys Pro Arg Glu Glu Gln Tyr Asn Ser Thr
                        340                 345                 350

Tyr Arg Val Val Ser Val Leu Thr Val Leu His Gln Asp Trp Leu Asn
                        355                 360                 365

Gly Lys Glu Tyr Lys Cys Lys Val Ser Asn Lys Ala Leu Pro Ala Pro
        370                 375                 380

Ile Glu Lys Thr Ile Ser Lys Ala Lys Gly Gln Pro Arg Glu Pro Gln
        385                 390                 395                 400

Val Tyr Thr Leu Pro Pro Ser Arg Asp Glu Leu Thr Lys Asn Gln Val
                        405                 410                 415

Ser Leu Thr Cys Leu Val Lys Gly Phe Tyr Pro Ser Asp Ile Ala Val
                        420                 425                 430

Glu Trp Glu Ser Asn Gly Gln Pro Glu Asn Asn Tyr Lys Thr Thr Pro
                        435                 440                 445

Pro Val Leu Asp Ser Asp Gly Ser Phe Phe Leu Tyr Ser Lys Leu Thr
        450                 455                 460

Val Asp Lys Ser Arg Trp Gln Gln Gly Asn Val Phe Ser Cys Ser Val
        465                 470                 475                 480

Met His Glu Ala Leu His Asn His Tyr Thr Gln Lys Ser Leu Ser Leu
                        485                 490                 495

Ser Pro Gly Lys
                    500

<210> SEQ ID NO 38
<211> LENGTH: 1503
<212> TYPE: DNA
<213> ORGANISM: Homo sapiens

<400> SEQUENCE: 38
```

```
atgctactag taaatcagtc acaccaaggc ttcaataagg aacacacaag caagatggta      60
agcgctattg ttttatatgt gcttttggcg gcggcggcgc attctgcctt tgcggcggga     120
tcctgttgga gtccattacc cttcatgtgt ggcggtagtc tctctggtag gtctgataat     180
cactcccagg actctaccag cgacctgatc cccgcaccac cgctgtctaa ggtgccactg     240
cagcaaaact tccaggacaa tcaatttcac ggtaaatggt acgtggtcgg cctggctgga     300
aaccgtatcc tgcgcgacga tcagcatcct atgaatatgt acgcgactat ttatgaactg     360
aaggaagaca aaagctacaa cgttacctcc gtgatctctt cacacaagaa atgcgaatat     420
acgattgcca ccttcgtgcc gggaagccag cctggcgagt ttaccctggg caatatcaag     480
tcttacggag acaaaacctc atatctggtg cgcgttgtgt ccactgatta caaccaatat     540
gcagtcgttt tctttaagct ggcggaagat aatgcagagt tctttgccat caccatttat     600
ggccgtacta aggagctggc cagcgaactg aaagagaact tcattcgctt tagtaaatcg     660
ctgggcctgc cagagaatca cattgttttc cctgtcccca ttgaccagtg tattgacggc     720
tctagatcag gtggcacctc aggtggcggt agtgtcccgg ggtcggggtc tagtggttcg     780
accagcggct ccggtaaaag ctccgagggc agcggccaag cttcgaccca tacctgccca     840
ccatgtccag ctcctgaact gctgggtggt ccaagcgtgt tcctgtttcc gcctaagcct     900
aaagacaccc tgatgatcag ccgtacccca gaggtcacct gcgtggtcgt tgacgtttcc     960
cacgaagatc cagaggtcaa gttcaactgg tacgtggatg gcgttgaagt gcataatgct    1020
aagaccaaac ccgtgaagga gcagtacaac tctacctatc gcgtggtctc agtcctgacc    1080
gttctgcacc aggactggct gaacggcaaa gagtataagt gcaaagtctc taataaggcg    1140
ctgcccgcac caatcgaaaa aaccatttca aggcgaagg gtcagccccg tgagccacag    1200
gtttacaccc tgcccccaag tcgcgacgaa ctgaccaaga accaggtgtc gctgacctgt    1260
ctggtcaaag gcttctatcc gtctgatatt gcagtggaat gggagtcaaa tggtcagcct    1320
gagaacaatt acaagaccac cccgcctgtt ctggactccg atggctcttt ctttctgtat    1380
agcaagctga ccgtggataa atcccgctgg cagcagggta acgtgttcag ctgctcagtg    1440
atgcatgaag ccctgcacaa tcattacacc cagaagagtc tgtcgctgag cccgggtaaa    1500
taa                                                                  1503
```

<210> SEQ ID NO 39
<211> LENGTH: 500
<212> TYPE: PRT
<213> ORGANISM: Homo sapiens

<400> SEQUENCE: 39

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Gly Ser Cys Trp Ser Pro Leu Pro Phe
        35                  40                  45

Met Cys Gly Gly Ser Leu Ser Gly Arg Ser Asp Asn His Ser Gln Asp
    50                  55                  60

Ser Thr Ser Asp Leu Ile Pro Ala Pro Pro Leu Ser Lys Val Pro Leu
65                  70                  75                  80

Gln Gln Asn Phe Gln Asp Asn Gln Phe His Gly Lys Trp Tyr Val Val
                85                  90                  95

Gly Leu Ala Gly Asn Arg Ile Leu Arg Asp Asp Gln His Pro Met Asn
```

```
                100             105             110
Met Tyr Ala Thr Ile Tyr Glu Leu Lys Glu Asp Lys Ser Tyr Asn Val
            115                 120             125

Thr Ser Val Ile Ser Ser His Lys Lys Cys Glu Tyr Thr Ile Ala Thr
            130             135             140

Phe Val Pro Gly Ser Gln Pro Gly Glu Phe Thr Leu Gly Asn Ile Lys
145             150                 155                     160

Ser Tyr Gly Asp Lys Thr Ser Tyr Leu Val Arg Val Val Ser Thr Asp
                165             170             175

Tyr Asn Gln Tyr Ala Val Val Phe Phe Lys Leu Ala Glu Asp Asn Ala
            180             185             190

Glu Phe Phe Ala Ile Thr Ile Tyr Gly Arg Thr Lys Glu Leu Ala Ser
            195             200             205

Glu Leu Lys Glu Asn Phe Ile Arg Phe Ser Lys Ser Leu Gly Leu Pro
            210             215             220

Glu Asn His Ile Val Phe Pro Val Pro Ile Asp Gln Cys Ile Asp Gly
225             230             235             240

Ser Arg Ser Gly Gly Thr Ser Gly Gly Gly Ser Val Pro Gly Ser Gly
                245             250             255

Ser Ser Gly Ser Thr Ser Gly Ser Gly Lys Ser Ser Glu Gly Ser Gly
            260             265             270

Gln Ala Ser Thr His Thr Cys Pro Pro Cys Pro Ala Pro Glu Leu Leu
            275             280             285

Gly Gly Pro Ser Val Phe Leu Phe Pro Pro Lys Pro Lys Asp Thr Leu
            290             295             300

Met Ile Ser Arg Thr Pro Glu Val Thr Cys Val Val Val Asp Val Ser
305             310             315             320

His Glu Asp Pro Glu Val Lys Phe Asn Trp Tyr Val Asp Gly Val Glu
                325             330             335

Val His Asn Ala Lys Thr Lys Pro Arg Glu Glu Gln Tyr Asn Ser Thr
            340             345             350

Tyr Arg Val Val Ser Val Leu Thr Val Leu His Gln Asp Trp Leu Asn
            355             360             365

Gly Lys Glu Tyr Lys Cys Lys Val Ser Asn Lys Ala Leu Pro Ala Pro
            370             375             380

Ile Glu Lys Thr Ile Ser Lys Ala Lys Gly Gln Pro Arg Glu Pro Gln
385             390             395             400

Val Tyr Thr Leu Pro Pro Ser Arg Asp Glu Leu Thr Lys Asn Gln Val
                405             410             415

Ser Leu Thr Cys Leu Val Lys Gly Phe Tyr Pro Ser Asp Ile Ala Val
            420             425             430

Glu Trp Glu Ser Asn Gly Gln Pro Glu Asn Asn Tyr Lys Thr Thr Pro
            435             440             445

Pro Val Leu Asp Ser Asp Gly Ser Phe Phe Leu Tyr Ser Lys Leu Thr
450             455             460

Val Asp Lys Ser Arg Trp Gln Gln Gly Asn Val Phe Ser Cys Ser Val
465             470             475             480

Met His Glu Ala Leu His Asn His Tyr Thr Gln Lys Ser Leu Ser Leu
            485             490             495

Ser Pro Gly Lys
            500

<210> SEQ ID NO 40
```

<211> LENGTH: 1503
<212> TYPE: DNA
<213> ORGANISM: Homo sapiens

<400> SEQUENCE: 40

```
atgctactag taaatcagtc acaccaaggc ttcaataagg aacacacaag caagatggta      60
agcgctattg ttttatatgt gcttttggcg gcggcggcgc attctgcctt tgcggcggga     120
tcctgttgga gtccattacc cttcatgtgt ggcggtagtt ccaagtacca gctgtatagt     180
ggatcccagg actctaccag cgacctgatc cccgcaccac cgctgtctaa ggtgccactg     240
cagcaaaact tccaggacaa tcaatttcac ggtaaatggt acgtggtcgg cctggctgga     300
aaccgtatcc tgcgcgacga tcagcatcct atgaatatgt acgcgactat ttatgaactg     360
aaggaagaca aaagctacaa cgttacctcc gtgatctctt cacacaagaa atgcgaatat     420
acgattgcca ccttcgtgcc gggaagccag cctggcgagt ttaccctggg caatatcaag     480
tcttacggag acaaaacctc atatctggtg cgcgttgtgt ccactgatta caaccaatat     540
gcagtcgttt tctttaagct ggcggaagat aatgcagagt tctttgccat caccatttat     600
ggccgtacta aggagctggc cagcgaactg aaagagaact tcattcgctt tagtaaatcg     660
ctgggcctgc cagagaatca cattgttttc cctgtcccca ttgaccagtg tattgacggc     720
tctagatcag gtggcacctc aggtggcggt agtgtcccgg ggtcggggtc tagtggttcg     780
accagcggct ccggtaaaag ctccgagggc agcggccaag cttcgaccca tacctgccca     840
ccatgtccag ctcctgaact gctgggtggt ccaagcgtgt tcctgtttcc gcctaagcct     900
aaagacaccc tgatgatcag ccgtaccccg aggtcaccct gcgtggtcgt tgacgttcc      960
cacgaagatc cagaggtcaa gttcaactgg tacgtggatg gcgttgaagt gcataatgct    1020
aagaccaaac cccgtgaaga gcagtacaac tctacctatc gcgtggtctc agtcctgacc    1080
gttctgcacc aggactggct gaacggcaaa gagtataagt gcaaagtctc taataaggcg    1140
ctgcccgcac caatcgaaaa aaccatttca aaggcgaagg gtcagccccg tgagccacag    1200
gtttacaccc tgcccccaag tcgcgacgaa ctgaccaaga accaggtgtc gctgacctgt    1260
ctggtcaaag cttctatcc gtctgatatt gcagtggaat gggagtcaaa tggtcagcct    1320
gagaacaatt acaagaccac cccgcctgtt ctggactccg atggctcttt ctttctgtat    1380
agcaagctga ccgtggataa atcccgctgg cagcagggta acgtgttcag ctgctcagtg    1440
atgcatgaag ccctgcacaa tcattacacc cagaagagtc tgtcgctgag cccgggtaaa    1500
taa                                                                  1503
```

<210> SEQ ID NO 41
<211> LENGTH: 500
<212> TYPE: PRT
<213> ORGANISM: Homo sapiens

<400> SEQUENCE: 41

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Ala Ala Ala
            20                  25                  30

Ala His Ser Ala Phe Ala Ala Gly Ser Cys Trp Ser Pro Leu Pro Phe
        35                  40                  45

Met Cys Gly Gly Ser Ser Lys Tyr Gln Leu Tyr Ser Gly Ser Gln Asp
    50                  55                  60

Ser Thr Ser Asp Leu Ile Pro Ala Pro Pro Leu Ser Lys Val Pro Leu
```

-continued

```
                65                  70                  75                  80
Gln Gln Asn Phe Gln Asp Asn Gln Phe His Gly Lys Trp Tyr Val Val
                            85                  90                  95

Gly Leu Ala Gly Asn Arg Ile Leu Arg Asp Asp Gln His Pro Met Asn
                100                 105                 110

Met Tyr Ala Thr Ile Tyr Glu Leu Lys Glu Asp Lys Ser Tyr Asn Val
                115                 120                 125

Thr Ser Val Ile Ser Ser His Lys Lys Cys Glu Tyr Thr Ile Ala Thr
            130                 135                 140

Phe Val Pro Gly Ser Gln Pro Gly Glu Phe Thr Leu Gly Asn Ile Lys
145                 150                 155                 160

Ser Tyr Gly Asp Lys Thr Ser Tyr Leu Val Arg Val Ser Thr Asp
                    165                 170                 175

Tyr Asn Gln Tyr Ala Val Val Phe Phe Lys Leu Ala Glu Asp Asn Ala
                180                 185                 190

Glu Phe Phe Ala Ile Thr Ile Tyr Gly Arg Thr Lys Glu Leu Ala Ser
            195                 200                 205

Glu Leu Lys Glu Asn Phe Ile Arg Phe Ser Lys Ser Leu Gly Leu Pro
    210                 215                 220

Glu Asn His Ile Val Phe Pro Val Pro Ile Asp Gln Cys Ile Asp Gly
225                 230                 235                 240

Ser Arg Ser Gly Gly Thr Ser Gly Gly Gly Ser Val Pro Gly Ser Gly
                    245                 250                 255

Ser Ser Gly Ser Thr Ser Gly Gly Lys Ser Ser Glu Gly Ser Gly
                260                 265                 270

Gln Ala Ser Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                    325                 330                 335

Val His Asn Ala Lys Thr Lys Pro Arg Glu Glu Gln Tyr Asn Ser Thr
                340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                    405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                    485                 490                 495
```

Ser Pro Gly Lys
        500

<210> SEQ ID NO 42
<211> LENGTH: 1503
<212> TYPE: DNA
<213> ORGANISM: Homo sapiens

<400> SEQUENCE: 42

| | | | | | |
|---|---|---|---|---|---|
| atgctactag | taaatcagtc | acaccaaggc | ttcaataagg | aacacacaag | caagatggta | 60 |
| agcgctattg | ttttatatgt | gcttttggcg | gcggcggcgc | attctgcctt | tgcggcggga | 120 |
| tcctgttgga | gtccattacc | cttcatgtgt | ggcggtagtg | tcccgctgtc | gctgtatagt | 180 |
| ggatcccagg | actctaccag | cgacctgatc | cccgcaccac | cgctgtctaa | ggtgccactg | 240 |
| cagcaaaact | tccaggacaa | tcaatttcac | ggtaaatggt | acgtggtcgg | cctggctgga | 300 |
| aaccgtatcc | tgcgcgacga | tcaggatcct | cagaatatgt | acgcgactat | ttatgaactg | 360 |
| aaggaagaca | aaagctacaa | cgttacctcc | gtgatctctt | cacacaagaa | atgcgaatat | 420 |
| acgattgcca | ccttcgtgcc | gggaagccag | cctggcgagt | ttaccctggg | caatatcaag | 480 |
| tcttacgag | acaaaacctc | atatctggtg | cgcgttgtgt | ccactgatta | caaccaatat | 540 |
| gcagtcgttt | tctttaagaa | ggcgtcacag | aatgcagagt | tctttgccat | caccatttat | 600 |
| ggccgtacta | aggagctggc | cagcgaactg | aaagagaact | tcattcgctt | tagtaaatcg | 660 |
| ctgggcctgc | cagagaatca | cattgttttc | cctgtcccca | ttgaccagtg | tattgacggc | 720 |
| tctagatcag | gtggcacctc | aggtggcggt | agtgtcccgg | ggtcggggtc | tagtggttcg | 780 |
| accagcggct | ccggtaaaag | ctccgagggc | agcggccaag | cttcgaccca | tacctgccca | 840 |
| ccatgtccag | ctcctgaact | gctgggtggt | ccaagcgtgt | tcctgtttcc | gcctaagcct | 900 |
| aaagacaccc | tgatgatcag | ccgtacccca | gaggtcacct | gcgtggtcgt | tgacgtttcc | 960 |
| cacgaagatc | cagaggtcaa | gttcaactgg | tacgtggatg | gcgttgaagt | gcataatgct | 1020 |
| aagaccaaac | cccgtgaaga | gcagtacaac | tctacctatc | gcgtggtctc | agtcctgacc | 1080 |
| gttctgcacc | aggactggct | gaacggcaaa | gagtataagt | gcaaagtctc | taataaggcg | 1140 |
| ctgcccgcac | caatcgaaaa | aaccatttca | aaggcgaagg | gtcagccccg | tgagccacag | 1200 |
| gtttacaccc | tgcccccaag | tcgcgacgaa | ctgaccaaga | accaggtgtc | gctgacctgt | 1260 |
| ctggtcaaag | gcttctatcc | gtctgatatt | gcagtggaat | gggagtcaaa | tggtcagcct | 1320 |
| gagaacaatt | acaagaccac | cccgcctgtt | ctggactccg | atggctcttt | ctttctgtat | 1380 |
| agcaagctga | ccgtggataa | atcccgctgg | cagcagggta | acgtgttcag | ctgctcagtg | 1440 |
| atgcatgaag | ccctgcacaa | tcattacacc | cagaagagtc | tgtcgctgag | cccgggtaaa | 1500 |
| taa | | | | | | 1503 |

<210> SEQ ID NO 43
<211> LENGTH: 500
<212> TYPE: PRT
<213> ORGANISM: Homo sapiens

<400> SEQUENCE: 43

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Gly Ser Cys Trp Ser Pro Leu Pro Phe

```
                35                  40                  45
Met Cys Gly Gly Ser Val Pro Leu Ser Leu Tyr Ser Gly Ser Gln Asp
 50                  55                  60

Ser Thr Ser Asp Leu Ile Pro Ala Pro Leu Ser Lys Val Pro Leu
 65                  70                  75                  80

Gln Gln Asn Phe Gln Asp Asn Gln Phe His Gly Lys Trp Tyr Val Val
                     85                  90                  95

Gly Leu Ala Gly Asn Arg Ile Leu Arg Asp Asp Gln Asp Pro Gln Asn
                100                 105                 110

Met Tyr Ala Thr Ile Tyr Glu Leu Lys Glu Asp Lys Ser Tyr Asn Val
                115                 120                 125

Thr Ser Val Ile Ser Ser His Lys Lys Cys Glu Tyr Thr Ile Ala Thr
130                 135                 140

Phe Val Pro Gly Ser Gln Pro Gly Glu Phe Thr Leu Gly Asn Ile Lys
145                 150                 155                 160

Ser Tyr Gly Asp Lys Thr Ser Tyr Leu Val Arg Val Val Ser Thr Asp
                165                 170                 175

Tyr Asn Gln Tyr Ala Val Val Phe Phe Lys Lys Ala Ser Gln Asn Ala
                180                 185                 190

Glu Phe Phe Ala Ile Thr Ile Tyr Gly Arg Thr Lys Glu Leu Ala Ser
                195                 200                 205

Glu Leu Lys Glu Asn Phe Ile Arg Phe Ser Lys Ser Leu Gly Leu Pro
210                 215                 220

Glu Asn His Ile Val Phe Pro Val Pro Ile Asp Gln Cys Ile Asp Gly
225                 230                 235                 240

Ser Arg Ser Gly Gly Thr Ser Gly Gly Gly Ser Val Pro Gly Ser Gly
                245                 250                 255

Ser Ser Gly Ser Thr Ser Gly Ser Gly Lys Ser Ser Glu Gly Ser Gly
                260                 265                 270

Gln Ala Ser Thr His Thr Cys Pro Pro Cys Pro Ala Pro Glu Leu Leu
                275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
                340                 345                 350

Tyr Arg Val Val Ser Val Leu Thr Val Leu His Gln Asp Trp Leu Asn
                355                 360                 365

Gly Lys Glu Tyr Lys Cys Lys Val Ser Asn Lys Ala Leu Pro Ala Pro
                370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
450                 455                 460
```

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Pro Gly Lys
        500

<210> SEQ ID NO 44
<211> LENGTH: 22
<212> TYPE: PRT
<213> ORGANISM: Homo sapiens

<400> SEQUENCE: 44

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 45
<211> LENGTH: 21
<212> TYPE: PRT
<213> ORGANISM: Homo sapiens

<400> SEQUENCE: 45

Met Leu Leu Leu Val Thr Ser Leu Leu Cys Glu Leu Pro His Pro
1               5                   10                  15

Ala Phe Leu Leu Ile
            20

<210> SEQ ID NO 46
<211> LENGTH: 12
<212> TYPE: PRT
<213> ORGANISM: Homo sapiens

<400> SEQUENCE: 46

Gly Gly Ser Val Pro Leu Ser Leu Tyr Ser Gly Gly
1               5                   10

<210> SEQ ID NO 47
<211> LENGTH: 12
<212> TYPE: PRT
<213> ORGANISM: Homo sapiens

<400> SEQUENCE: 47

Gly Gly Ser Val Pro Gly Ser Gly Ser Ser Gly Gly
1               5                   10

<210> SEQ ID NO 48
<211> LENGTH: 12
<212> TYPE: PRT
<213> ORGANISM: Homo sapiens

<400> SEQUENCE: 48

Gly Gly Ser Gly Gly Ser Val Pro Leu Ser Leu Tyr
1               5                   10

<210> SEQ ID NO 49
<211> LENGTH: 15
<212> TYPE: PRT
<213> ORGANISM: Homo sapiens

<400> SEQUENCE: 49

-continued

Gly Gly Ser Gly Gly Ser Val Pro Leu Ser Leu Tyr Ser Gly Gly
1               5                   10                  15

<210> SEQ ID NO 50
<211> LENGTH: 18
<212> TYPE: PRT
<213> ORGANISM: Homo sapiens

<400> SEQUENCE: 50

Ser Gly Gly Gly Ser Gly Gly Gly Ser Val Pro Leu Ser Leu Tyr Ser
1               5                   10                  15

Gly Gly

<210> SEQ ID NO 51
<211> LENGTH: 21
<212> TYPE: PRT
<213> ORGANISM: Homo sapiens

<400> SEQUENCE: 51

Ser Gly Gly Gly Ser Gly Gly Gly Ser Val Pro Leu Ser Leu Tyr Ser
1               5                   10                  15

Gly Gly Ser Gly Gly
            20

<210> SEQ ID NO 52
<211> LENGTH: 7
<212> TYPE: PRT
<213> ORGANISM: Homo sapiens

<400> SEQUENCE: 52

Tyr Gly Leu Gly Phe Asn Phe
1               5

<210> SEQ ID NO 53
<211> LENGTH: 7
<212> TYPE: PRT
<213> ORGANISM: Homo sapiens

<400> SEQUENCE: 53

Arg Ile Asp Glu Thr Leu Gln
1               5

<210> SEQ ID NO 54
<211> LENGTH: 7
<212> TYPE: PRT
<213> ORGANISM: Homo sapiens

<400> SEQUENCE: 54

Phe Thr Pro Trp Pro Glu Ala
1               5

<210> SEQ ID NO 55
<211> LENGTH: 7
<212> TYPE: PRT
<213> ORGANISM: Homo sapiens

<400> SEQUENCE: 55

Trp Pro Glu Trp Asp Leu Trp
1               5

<210> SEQ ID NO 56
<211> LENGTH: 7
<212> TYPE: PRT
<213> ORGANISM: Homo sapiens

```
<400> SEQUENCE: 56

Glu Lys Trp Phe Arg Phe Met
1               5

<210> SEQ ID NO 57
<211> LENGTH: 7
<212> TYPE: PRT
<213> ORGANISM: Homo sapiens

<400> SEQUENCE: 57

Tyr Leu Glu Leu Met His Ser
1               5

<210> SEQ ID NO 58
<211> LENGTH: 7
<212> TYPE: PRT
<213> ORGANISM: Homo sapiens

<400> SEQUENCE: 58

Ser Val Leu Pro Pro Phe Met
1               5

<210> SEQ ID NO 59
<211> LENGTH: 7
<212> TYPE: PRT
<213> ORGANISM: Homo sapiens

<400> SEQUENCE: 59

Trp Ser Pro Leu Pro Phe Met
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Leu Ser Gly Arg Ser Asp Asn His
1               5

<210> SEQ ID NO 61
<211> LENGTH: 10
<212> TYPE: PRT
<213> ORGANISM: Homo sapiens

<400> SEQUENCE: 61

Met Pro Pro Pro Arg Leu Leu Phe Phe Leu
1               5                   10

<210> SEQ ID NO 62
<211> LENGTH: 9
<212> TYPE: PRT
<213> ORGANISM: Homo sapiens

<400> SEQUENCE: 62

Ala Ala Asn Ala Ala Asn Ala Ala Asn
1               5

<210> SEQ ID NO 63
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 63

His Ser Ser Lys Leu Gln Asp Glu Glu Glu Glu
1               5                   10
```

CTLA4-BINDING PROTEIN PEPTIDE-LINKER MASKS

CROSS REFERENCE TO RELATED APPLICATION APPLICATIONS

This application is a U.S. National Phase Application of International Application No. PCT/US2016/013292, filed Jan. 13, 2016, which claims priority to and the benefit of U.S. Provisional Patent Application No. 62/102,966, filed on Jan. 13, 2015, the content contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737762000200SubSeqList.txt, date recorded: Sep. 5, 2019, size: 55,06685,736 bytes).

BACKGROUND OF THE INVENTION

Cancer is the second leading cause of death in the United States, accounting for more deaths than the next five leading causes (chronic respiratory disease, stroke, accidents, Alzheimer's disease and diabetes). While great strides have been made especially with targeted therapies, the prognosis of late stage cancer including melanoma and prostate cancer remains poor. Immunotherapy has recently reemerged as a viable and exciting therapeutic option for advanced stage malignancies. Specifically, it is now recognized that one hallmark of cancer is immune evasion and significant efforts have identified targets and developed therapies to these targets to reactivate the immune system to recognize and treat cancer. In fact, the anti-CTLA-4 mAb, ipilimumab, has for the first time, led to long-term survival of patients suffering from stage III/IV malignant melanoma. Ipilimumab is an immune checkpoint antagonist and interrupts the inhibition of T cells by blocking CTLA-4 (Korman, A., et al., 2005. Tumor immunotherapy: preclinical and clinical activity of anti-CTLA-4 antibodies. *Current Opinion in Investigational Drugs* 6:582-591). Unfortunately, ipilimumab also leads to generalized (not tumor-specific) activation of T-cell dependent immune responses leading to immune-related adverse effects which can be life-threatening and are often dose-limiting (Weber, J. S., et al., 2008. Phase I/II study of ipilimumab for patients with metastatic melanoma. *Journal of Clinical Oncology* 26:5950-5956). These include enterocolitis, dermatitis, hypophysitis, uveitis, hepatitis, nephritis and death. Enterocolitis is the most common major toxicity (affecting approximately 20% of patients). The severe safety risks related to immune-mediated adverse reactions prompted the FDA to approve ipilimumab with a Risk Evaluation and Mitigation Strategy (REMS). Recently, coadministration of ipilimumab and a second immune checkpoint modulator targeting PD1 (e.g., nivolumab) has been shown to significantly increase efficacy of immunotherapy of melanoma when compared to ipilimumab alone. This gain, however, was associated with increased frequencies of grade 3/4 adverse effects, which affected more than 50% of patients receiving combination treatment (Wolchok, J. D., et al. 2013. Nivolumab plus Ipilimumab in Advanced Melanoma. *N Engl J Med*). These findings illustrate the urgent need in the art for strategies to alleviate side effects associated with systemic immune activation while preserving activity of immune checkpoint modulators against malignant disease. Provided herein are compositions and methods addressing these and other problems in the art.

BRIEF SUMMARY OF THE INVENTION

In a first aspect, there is provided a recombinant CTLA-4 binding protein including (i) a CTLA-4 binding domain; (ii) a CTLA-4 binding domain masking peptide; and (iii) a cleavable peptide linker connecting the CTLA-4 binding domain masking peptide to the CTLA-4 binding domain.

In another aspect, a recombinant nucleic acid encoding a recombinant CTLA-4 binding protein as disclosed herein including embodiments thereof is provided.

In another aspect, there is provided a peptide including a sequence having about 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

In another aspect, there is provided a recombinant CTLA-4 binding protein dimer including two identical binding protein domains, each of the binding protein domains including (i) a CTLA-4 binding domain; (ii) a CTLA-4 binding domain masking peptide; (iii) a cleavable peptide linker connecting the CTLA-4 binding domain masking peptide to the CTLA-4 binding domain; and (iv) a dimerizing domain covalently attached to the CTLA-4 binding domain, wherein the binding protein domains are bound together.

In another aspect, there is provided a method of treating a CTLA-4-mediated disease in a subject in need thereof. The method includes administering to a subject a therapeutically effective amount of a recombinant CTLA-4 binding protein as disclosed herein including embodiments thereof, or a therapeutically effective amount of a recombinant CTLA-4 binding protein dimer as disclosed herein including embodiments thereof.

In another aspect, there is provided a pharmaceutical composition including a pharmaceutically acceptable excipient and a recombinant CTLA-4 binding protein as disclosed herein including embodiments thereof or a recombinant CTLA-4 binding protein dimer as disclosed herein including embodiments thereof.

BRIEF DESCRIPTION OF THE DRAWINGS

FIG. 2A is a graph indicating phage expressing surface-bound Peptide 16 shows increased binding to immobilized mLcn2-Fc (left column) compared to mLcn2-Fc pre-complexed with CTLA-4-Fc (middle column) and PBS control (right column) as determined by ELISA (triplicates). FIG.

2B is a graph showing surface plasmon resonance traces of analyte mLcn2-Fc flowed over ligand Peptide 16 immobilized to a CM5 chip.

FIG. 3A-3D: Design and activation of covalently masked mLcn2-Fc in vitro. FIG. 3A is cartoon of MMP9 substrate-containing linker (Masked) and uncleavable linker Mxx9; protease substrate sequences in red box. Sequence legend: GGSVPLSLYSGG (SEQ ID NO:46); GGSVPGSGSSGG (SEQ ID NO:47). FIG. 3B is a graph of SEC analysis that shows binding of CTLA-4 only to unmasked mLcn2-Fc constructs. FIG. 3C is a graph of SPR of masked, MMP9-treated unmasked, and unmodified mLcn2-Fc binding to CTLA-4: Top: Sensorgram of unmodified (blue), MMP9-treated unmasked (green), and masked mLCN2-Fc (red) analytes at concentration of 3000 nM. Bottom: Sensorgrams of masked (left) and unmasked mLcn2-Fc (right) analytes at concentrations of 3000; 1000; 300; 100; and 30 nM. FIG. 3D is a graph of flow cytometric analysis of mLcn2-Fc constructs binding to mouse T lymphocytes. AlexaFluor(AF) 647-labeled unmodified, masked, and unmasked mLcn2-Fc were incubated with splenocytes from Foxp3gfp/KI DBA/2 mice. Regulatory T cells were gated and analyzed. P values based on quadruplicate analyses were calculated against neg. control (AF647). Masking mLcn2-Fc resulted in significantly reduced binding to cells compared to unmodified mLcn2-Fc (p=0.004) and unmasked mLcn2-Fc (p=0.003).

Figure 4:
Figure 4:
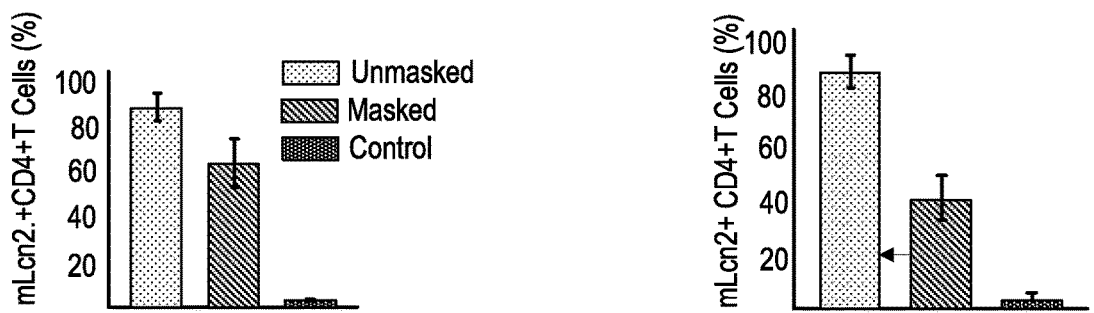

FIG. 4: In vivo detection of mLcn2 variants (CTLA-4 binding protein variants) in B16 tumor tissues. Note membrane staining of tumor-infiltrating lymphocytes (TILs) expressing either CD4 or CD8 by both masked and unmasked (MMP9-pretreated) mLcn2 constructs indicating MMP9 activity in tumors. Control refers to masked mLcn2 with non-cleavable linker (Mxx9) and, as expected, shows no reactivity.

Figure 5:
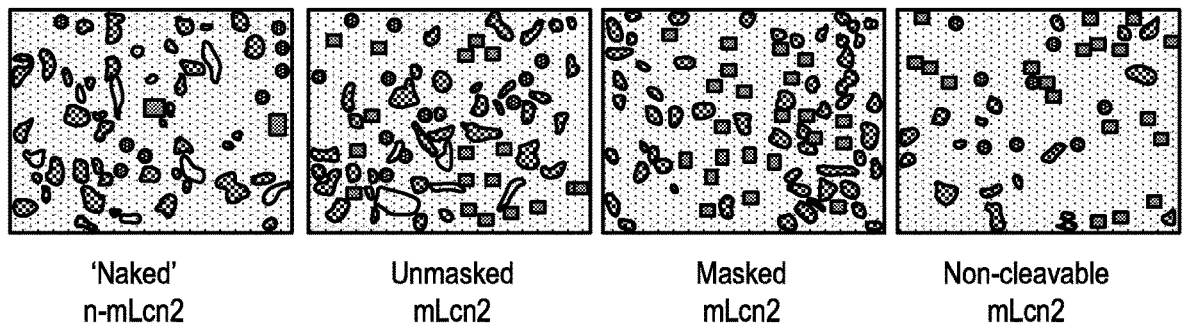

FIG. 5: Binding of CTLA-4 antagonist mLcn2 variants to cells within the pituitary gland. Note that, in contrast to the tumor environment, the masked mLcn2 did not bind to normal tissue constituents. By contrast, unmasked, MMP9 pretreated and mLcn2 without N-terminal masks bound equally well to pituicytes.

FIG. 6: Linker (cleavable peptide linker) variants designed to optimize mask release upon proteolytic linker cleavage. Sequence legend: GGSVPLSLYSGG (SEQ ID NO:46); GGSGGSVPLSLY (SEQ ID NO:48); GGSGGSV-PLSLYSGG (SEQ ID NO:49); SGGGSGGGSV-PLSLYSGG (SEQ ID NO:50); SGGGSGGGSV-PLSLYSGGSGG (SEQ ID NO:51).

Figure 7:
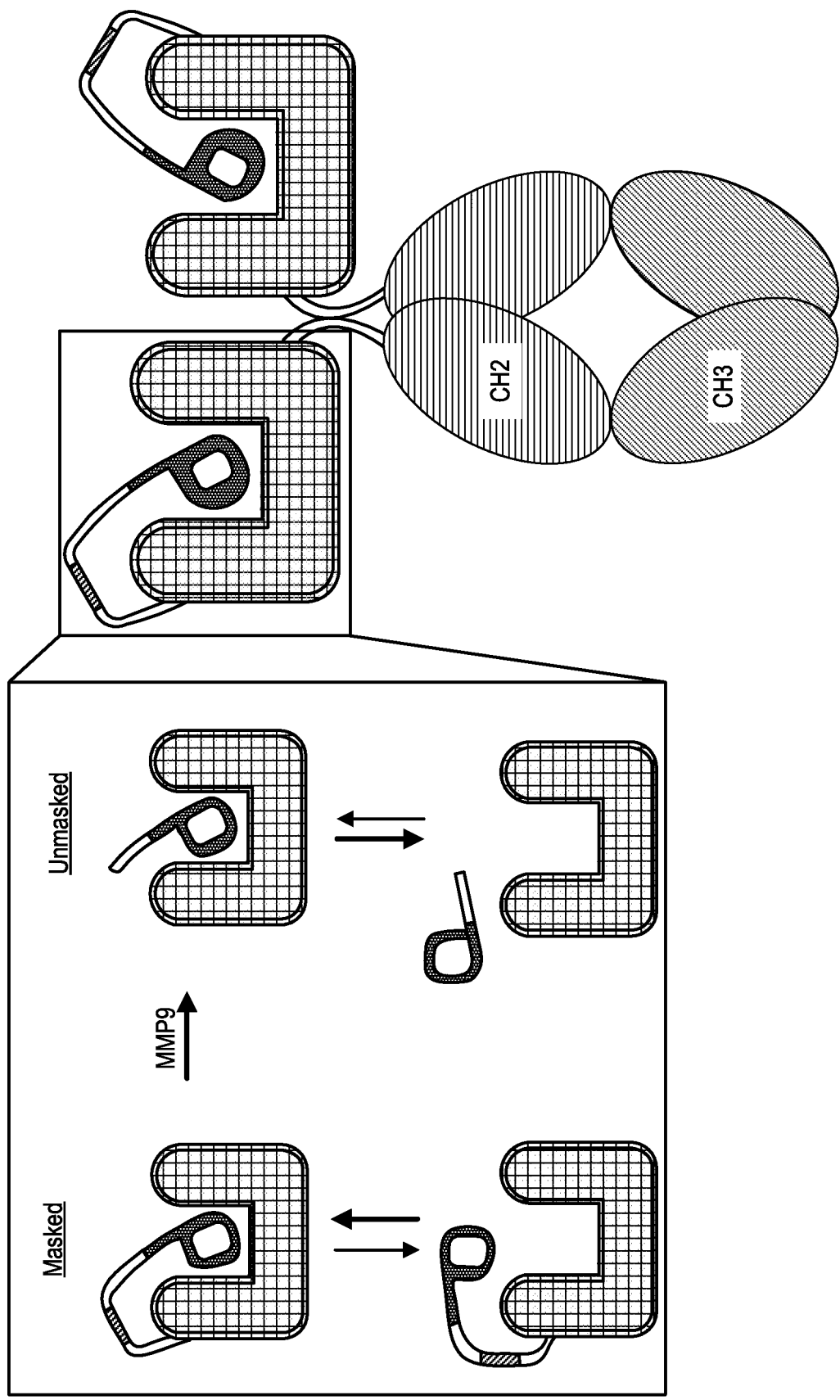

FIG. 7: Cartoon model of protease-activated CTLA-4 pro-antagonist. A pro-antagonist was constructed by covalently tethering a masking peptide (loop outline) to the N-terminus of mLcn2 (u-shape) through a flexible linker (grey lines) containing MMP-9 substrate (highlighted). The masked mLcn2 was cloned onto human IgG1 scaffold (grey ovals). Inset: Peptide mask (cleavable peptide linker) preferentially resides in the binding cavity of mLcn2; the mask is released upon MMP9 cleavage of substrate linker.

Figure 8A:
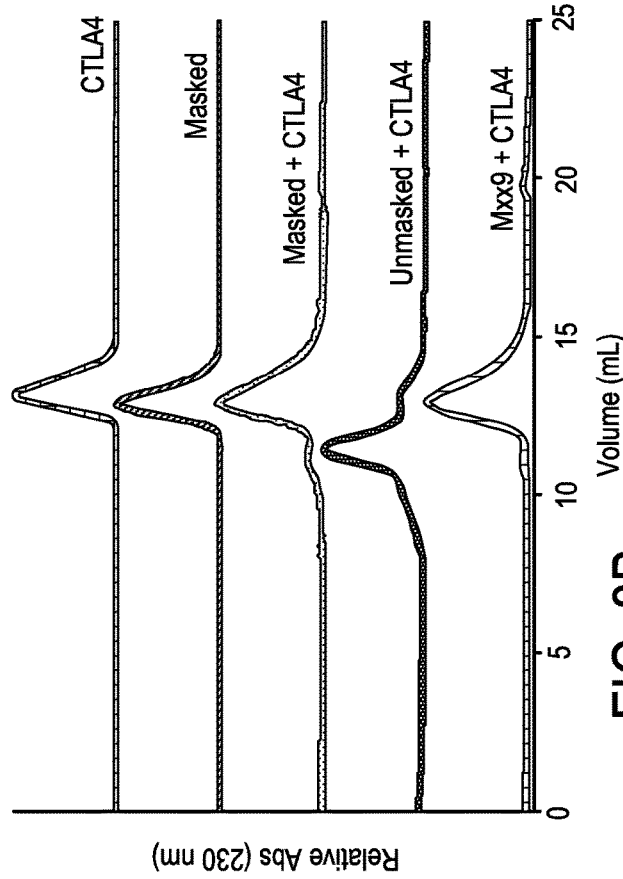
Figure 8B:
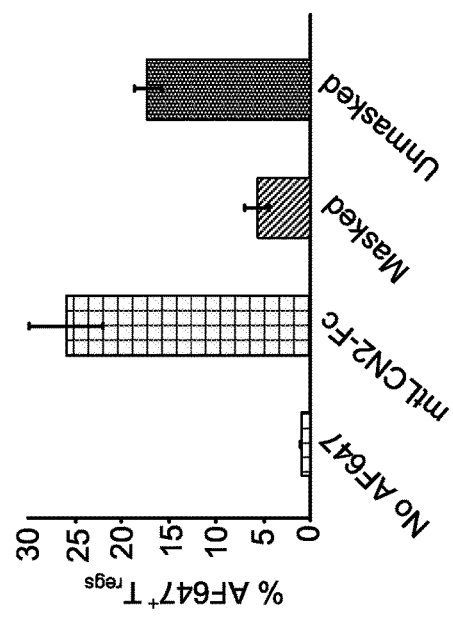
Figure 8C:
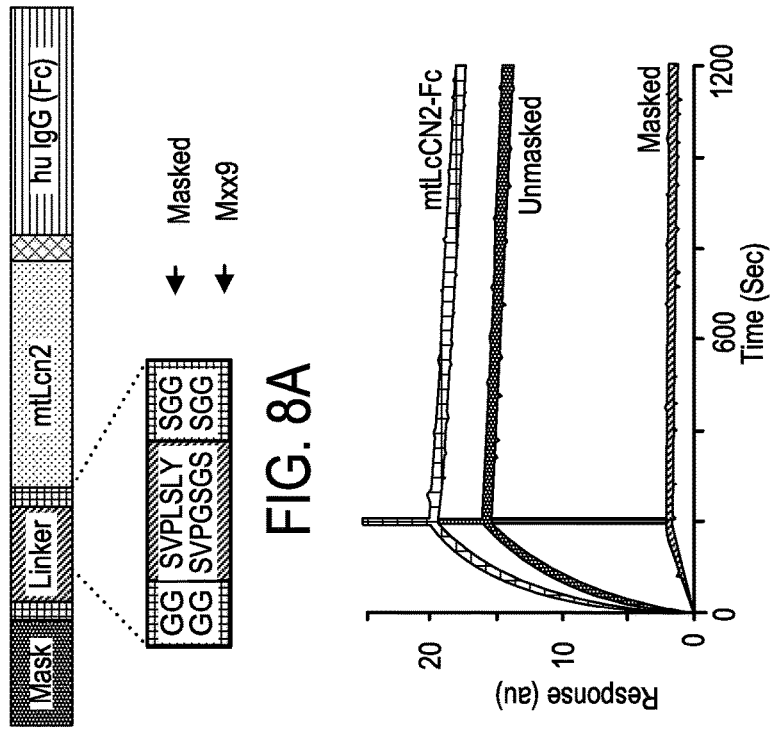
Figure 8D:
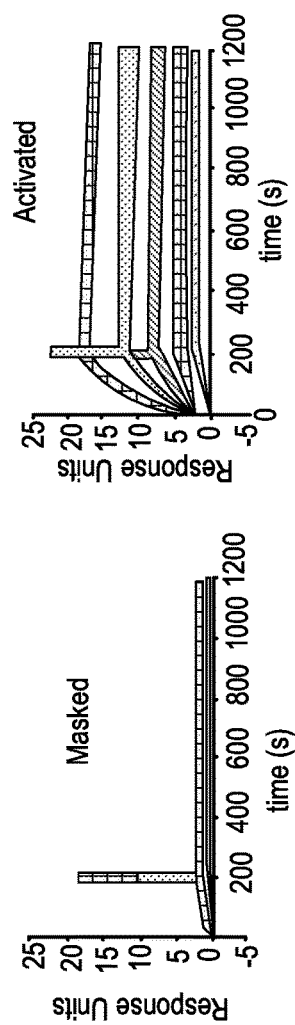

FIG. 8A-8D: Design and activation of masked mLcn2-Fc in vitro. FIG. 8A is a cartoon of sequences of MMP9 substrate-containing linker Masked and uncleavable linker Mxx9 (red box). Sequence legend: GGSVPLSLYSGG (SEQ ID NO:46); GGSVPGSGSSGG (SEQ ID NO:47). FIG. 8B is a graph of size-exclusion chromatography analysis of antigen CTLA-4 binding to mLcn2-Fc constructs. Apo CTLA-4 (blue trace) elutes from the Superdex 200 column at 13.0 mL. Apo masked mLcn2-Fc (red), unmasked and Mxx9 mLcn2-Fc (not shown) elute at ~12.7 mL. CTLA-4 incubated with masked (purple) or Mxx9 mLcn2-Fc (black) elutes at 12.85 mL. Unmasked mLcn2-Fc incubated with CTLA-4 elutes primarily at 11.3 mL (green), consistent with a heterodimeric complex. FIG. 8C is a graph showing surface plasmon resonance of masked, unmasked, and unmodified mLcn2-Fc binding to CTLA-4. Monomeric extracellular CTLA-4 was immobilized at low density on a CM5 chip. Top: Baseline subtracted sensorgram of unmodified (blue), unmasked (green), and masked mLcn2-Fc (red) analytes at concentration of 3000 nM. Bottom: Baseline subtracted sensorgrams of masked (left) and unmasked mLcn2-Fc (right) analytes at concentrations 3000; 1000; 300; 100; and 30 nM. FIG. 8D is a graph showing flow cytometric analysis of mLcn2-Fc constructs binding to murine regulatory T-cells. Alexa Fluor 647-labeled unmodified, masked, and unmasked mLcn2-Fc were incubated with splenocytes from Foxp3gfp/KI DBA/2 mice and analyzed via flow cytometry. Regulatory T-cells were isolated by forward and side scatters, DAPI– staining, and GFP+ fluorescence. Four experiments on two murine spleens were performed and the averages were calculated±s.d. P values were calculated for the difference in AF647 staining. Masked mLcn2-Fc had significantly reduced binding to cells compared to unmodified mLcn2-Fc (P=0.004) and unmasked mLcn2-Fc (P=0.003).

Figure 9:
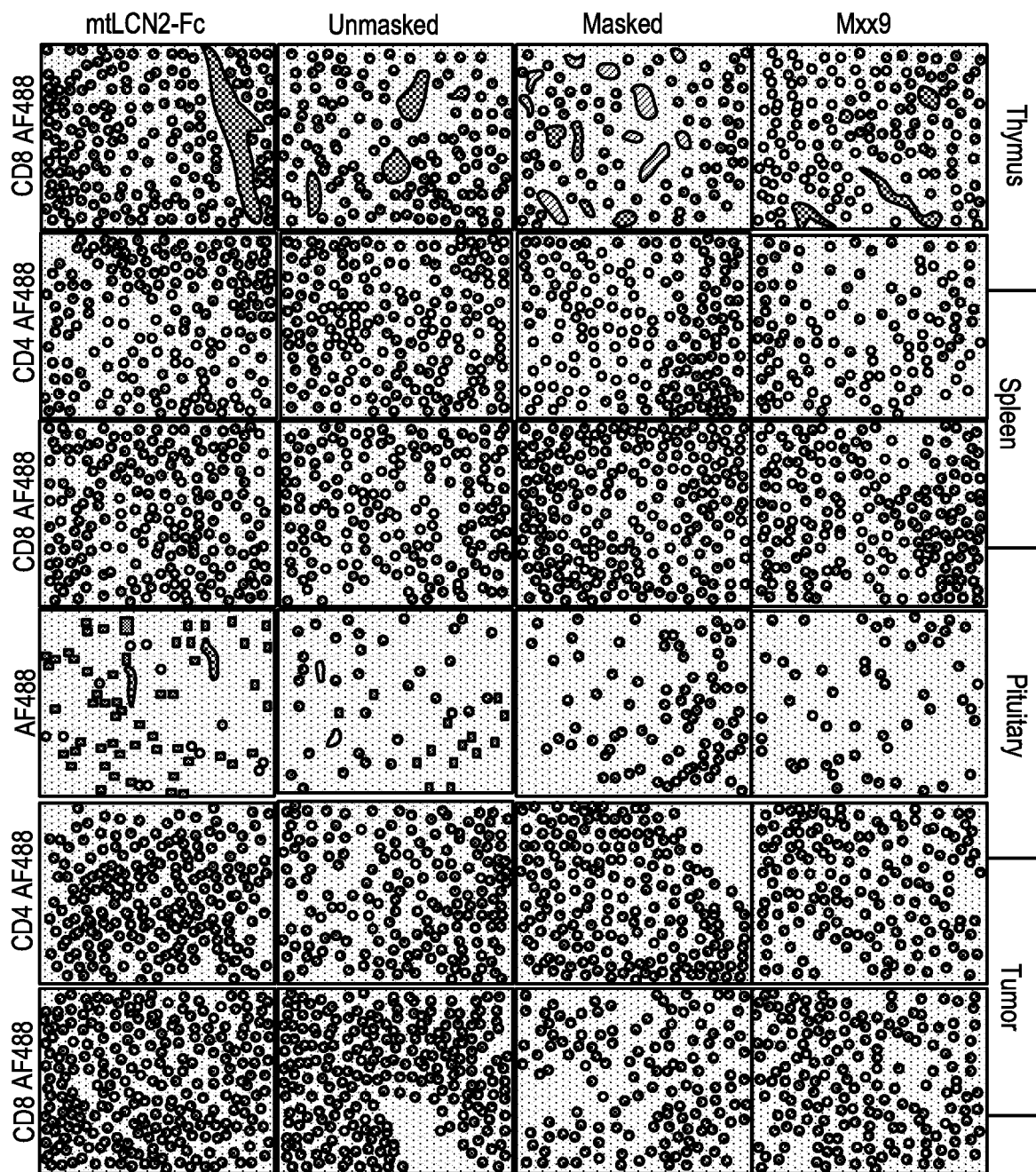

FIG. 9: Biodistribution of mLcn2-Fc constructs in vivo. (A-C) Naïve mice were injected i.v. with 100 μg of indicated mLcn2-Fc construct and tissue samples were collected 48 hr. post-dose. Cryosections were stained for CD4 or CD8 (medium gray) and human IgG (light gray) from the thymus (A), spleen (B), and pituitary gland (C, IgG only). (D) Melanoma-bearing mice were injected as above and tumor samples were collected 72 hr. post-dose. 4',6-diamidino-2-phenylindole (DAPI) nuclear staining shown in dark gray.

Figure 10A:
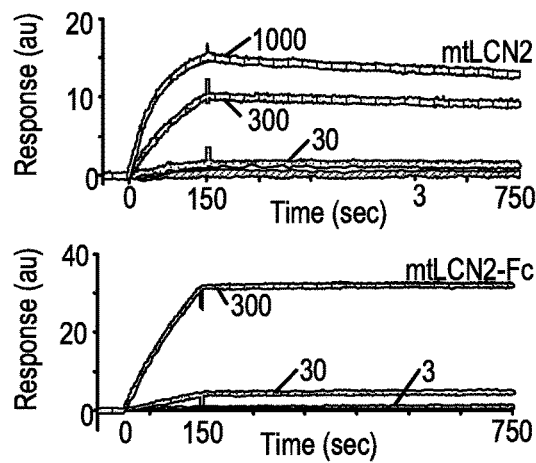

FIG. 10A: SPR analysis. Dimeric CTLA-4-Fc was immobilized at medium density to a CM5 chip. A range of 3-1000 nM monomeric mLCN2 (top) and 3-300 nM dimeric mLCN2-Fc (bottom) analytes were used for kinetics analyses. Monomeric mLCN2 had a ka=3.6 E4 $M^{-1}$ $s^{-1}$ and kd=2.0 E-4 $s^{-1}$ for CTLA-4. Dimeric mLCN2-Fc had a ka=1.0 E4 $M^{-1}$ $s^{-1}$; kd could not be determined as it was beyond the limitations of the instrument. Concentration of analytes is 1000; 300; 30; and 3 nM.

Figure 10B:
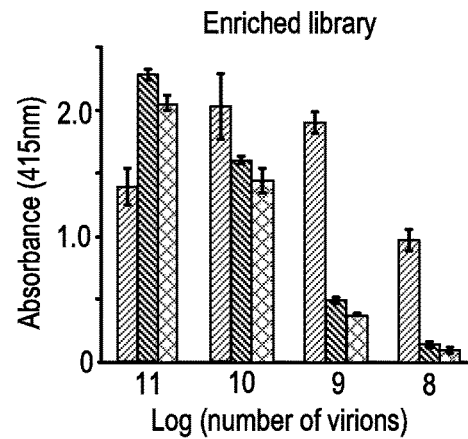

FIG. 10B: ELISA results of bacteriophage library after three rounds of enrichment. Wells in a 96-well plate were immobilized with mLcn2-Fc (left column), mLcn2-Fc pre-complexed with CTLA-4-Fc (middle column), or PBS (right column). Each condition was performed in triplicate.

Figure 10C:
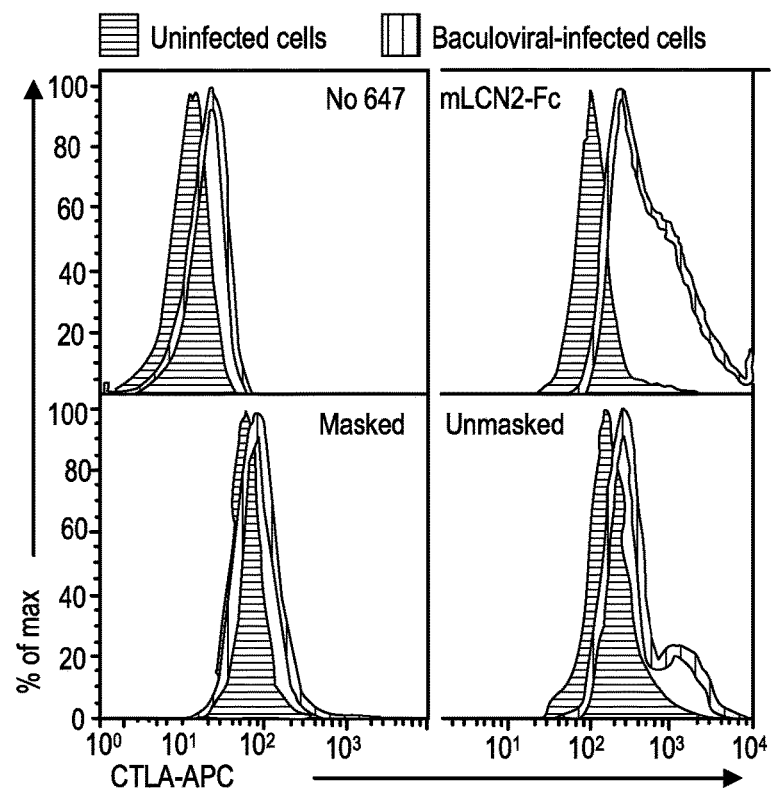

FIG. 10C: Flow cytometry analysis of Tni insect cells induced to transiently express human CTLA4-Fc. Cells were stained with Alexa Fluor-647 conjugated mLcn2-Fc variants and gated for Forward scatter/Side scatter, DAPI⁻, singlet size (pulse width), and APC. Uninfected cells stained with mLcn2-Fc are shown in grey as a negative control. Both variants mLcn2-Fc and Unmasked mLcn2-Fc showed binding to cells, whereas Masked mLcn2-Fc showed limited binding.

Figure 11:
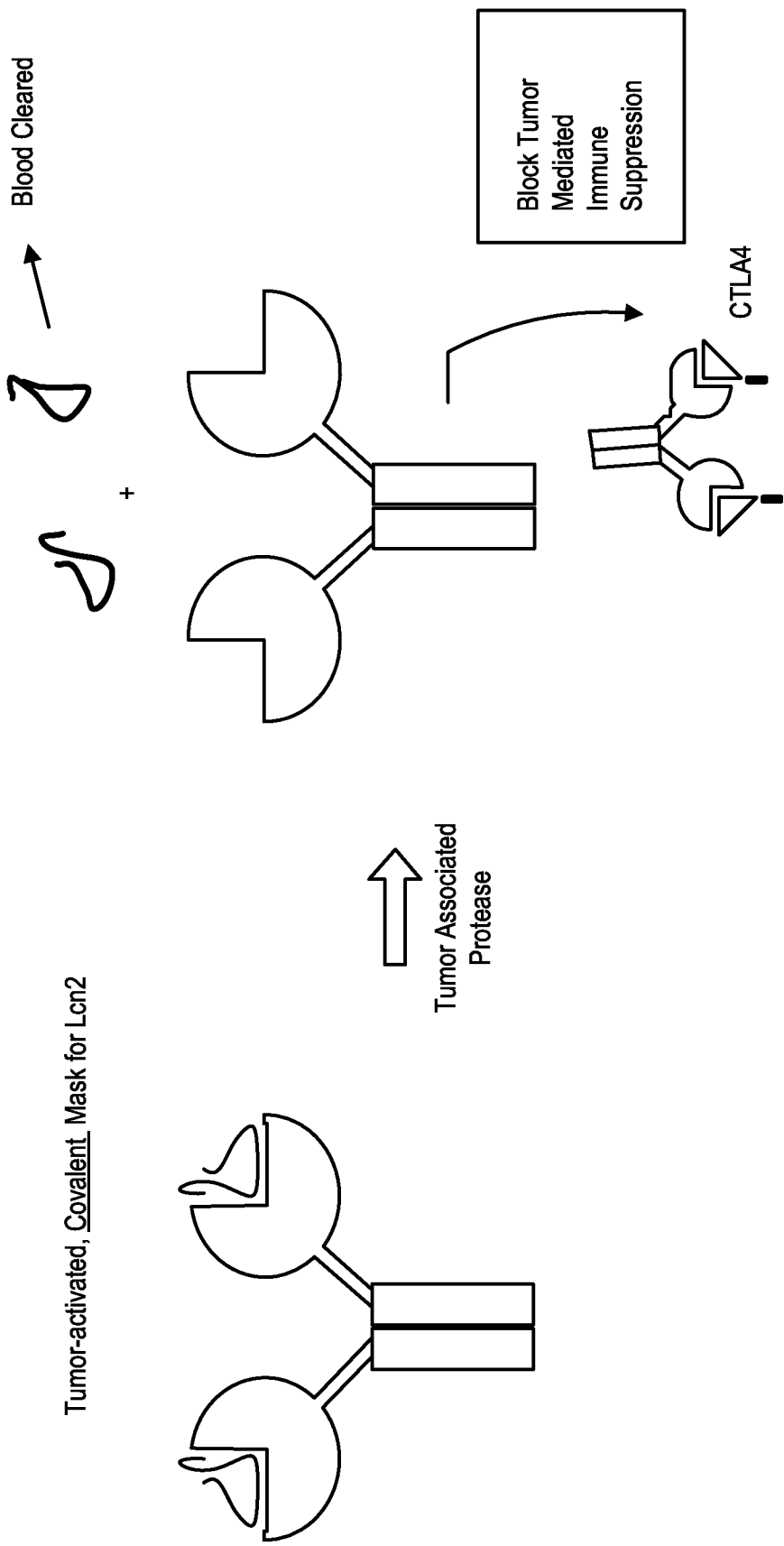

FIG. 11: Tumor-activated, Covalent Mask for Lcn2.

Figure 12A:
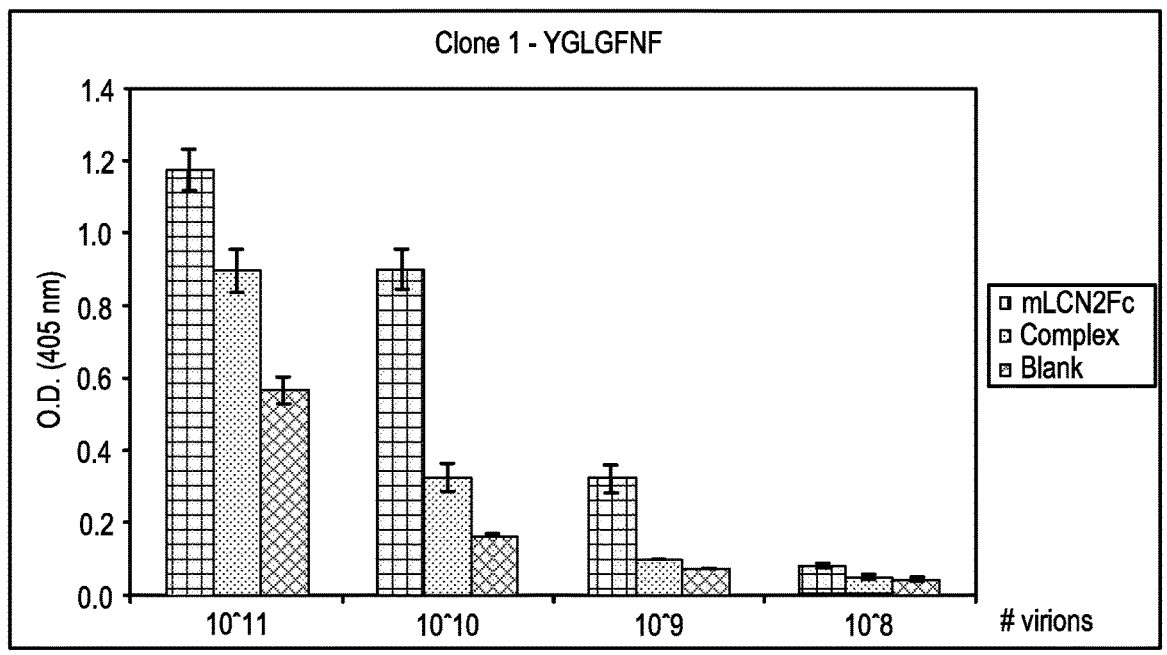
Figure 12B:
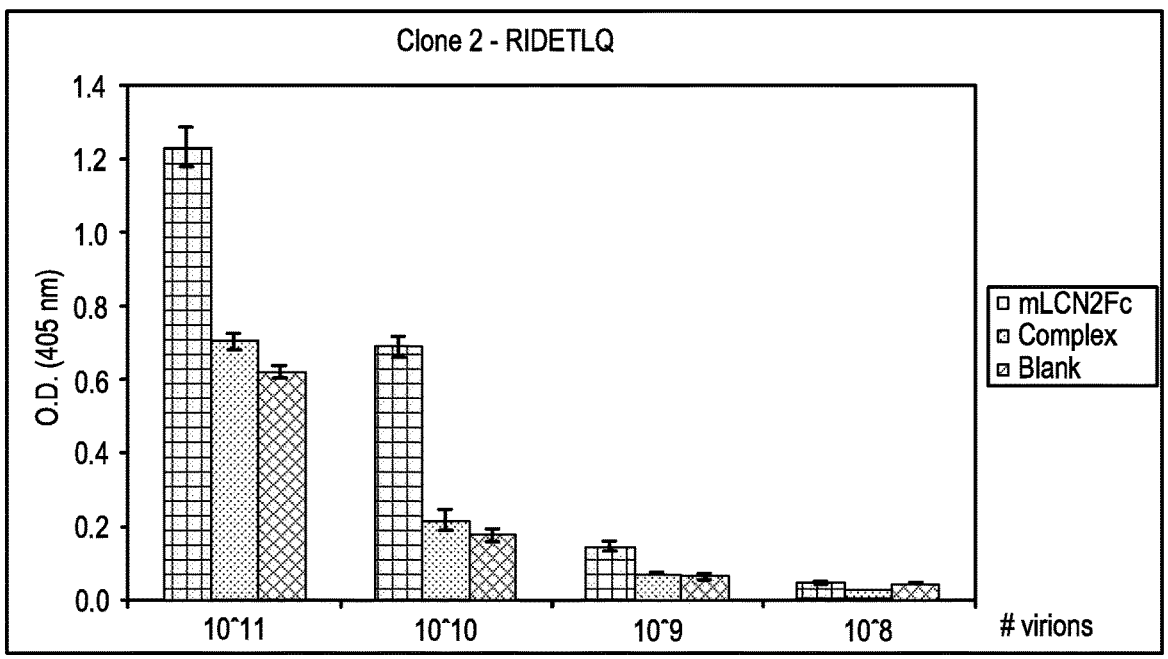
Figure 12C:
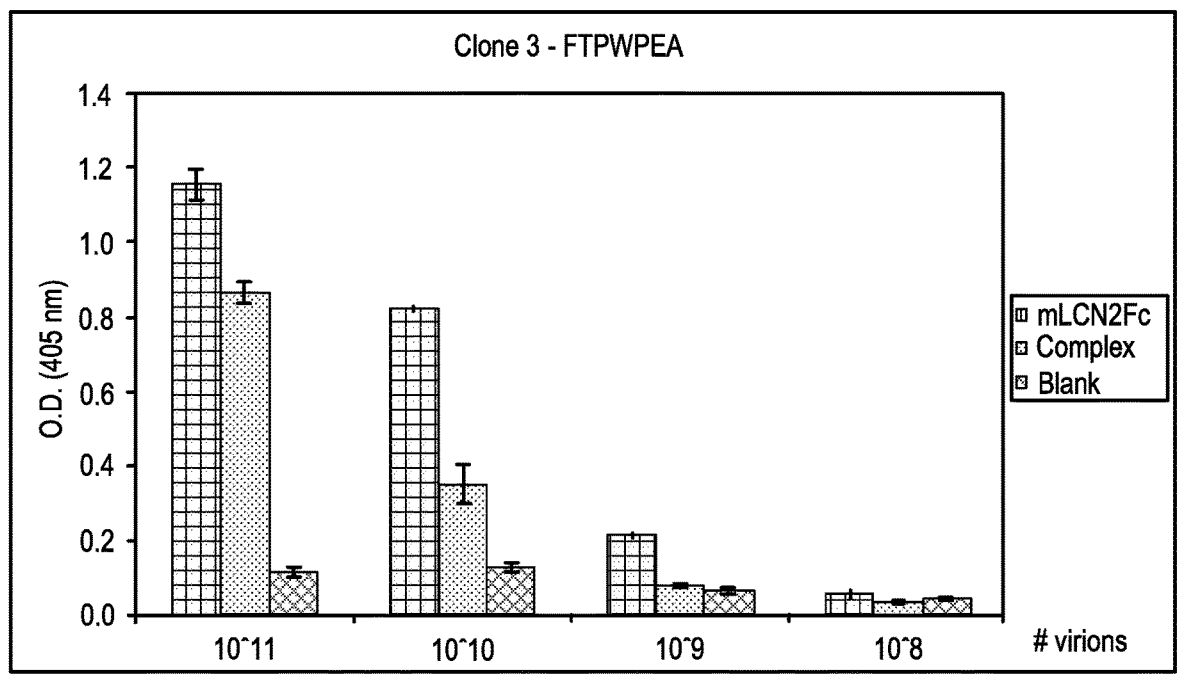
Figure 12D:
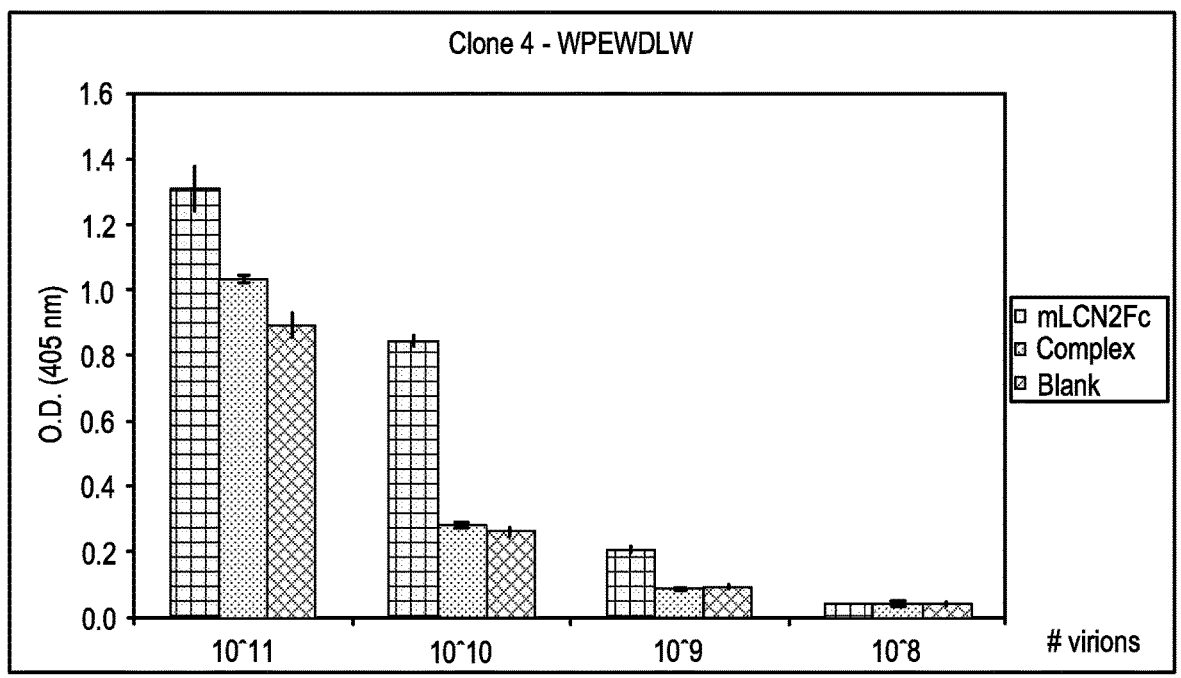

FIGS. 12A-12D: 18 min substrate incubation. Phage expressing surface-bound Peptide [sequence indicated in title bar of each graph] shows increased binding to immobilized Lcn2-Fc (left column) compared to Lcn2-Fc pre-complexed with CTLA4-Fc (middle column) or PBS control (right column) by ELISA. FIG. 12A is a graph showing Clone 1—YGLGFNF (SEQ ID NO:52); FIG. 12B is a graph showing Clone 2—RIDETLQ (SEQ ID NO:53); FIG. 12C is a graph showing Clone 3—FTPWPEA (SEQ ID NO:54); and FIG. 12D is a graph showing Clone 4—WPEWDLW (SEQ ID NO:55).

Figure 13A:
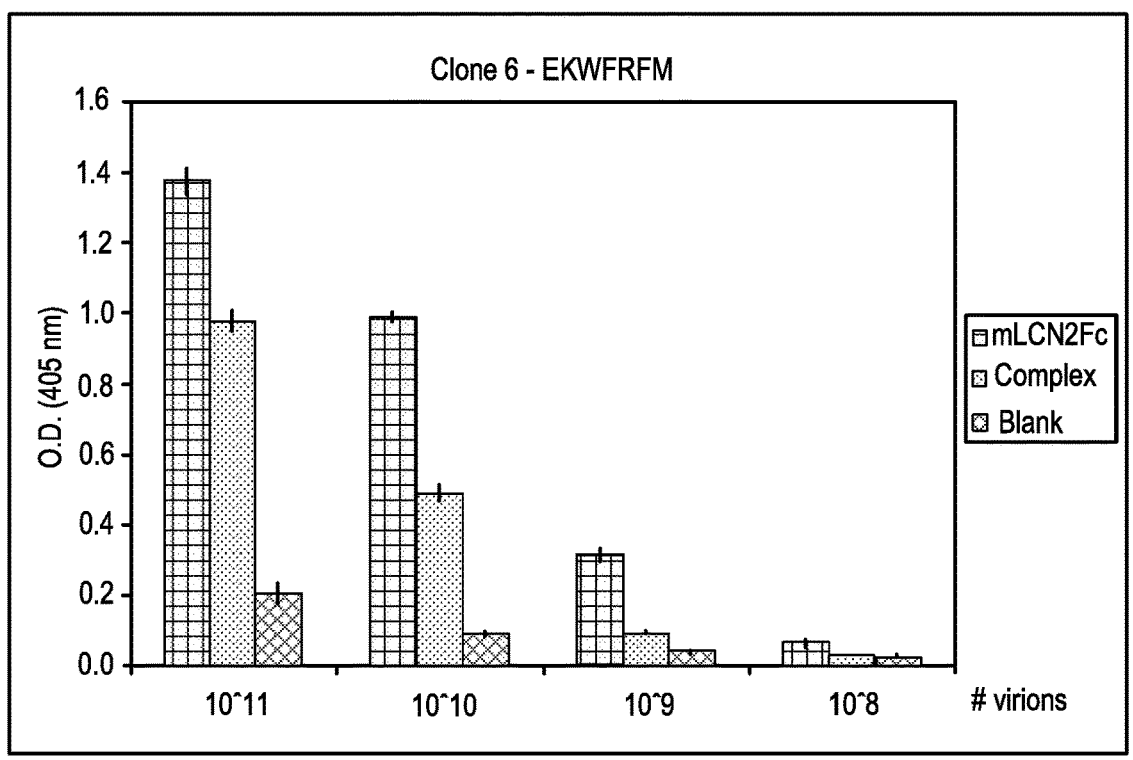
Figure 13B:
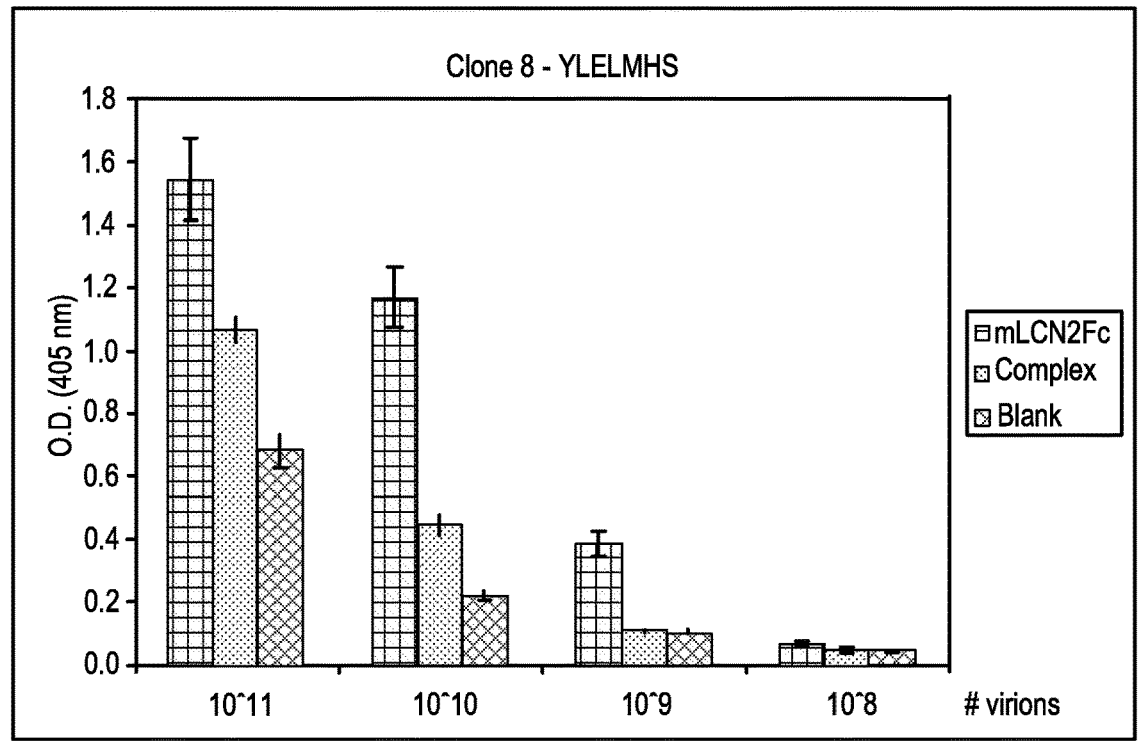
Figure 13C:
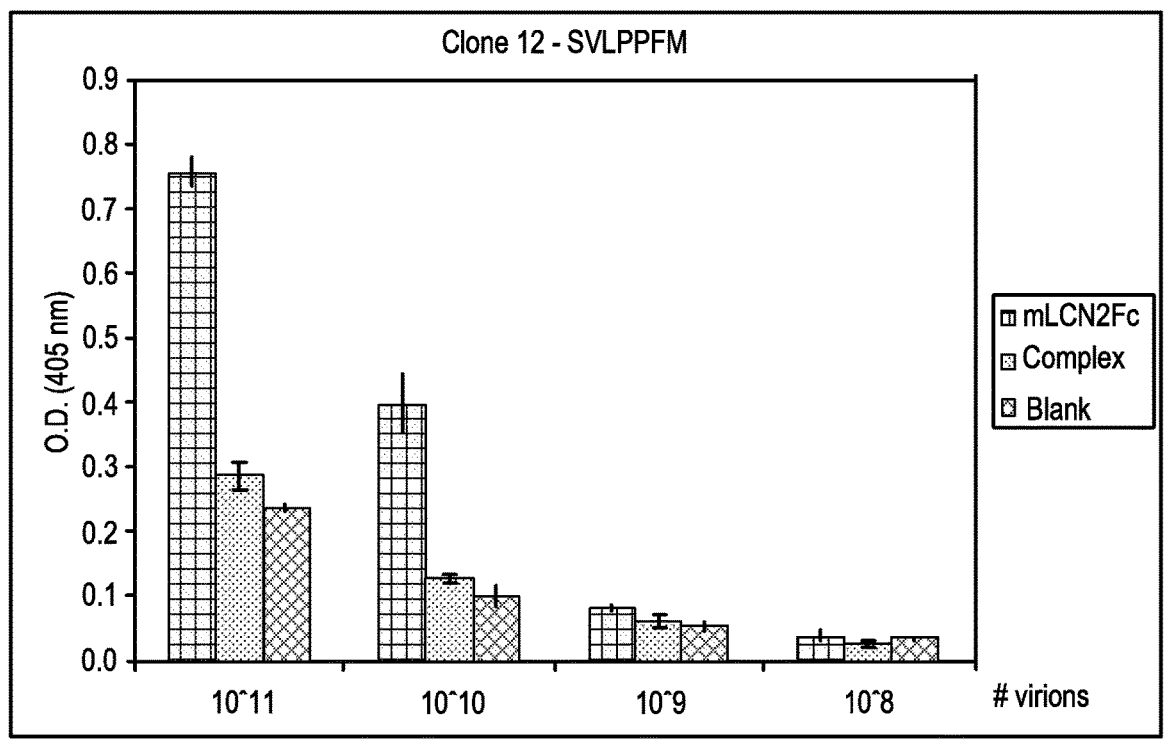
Figure 13D:
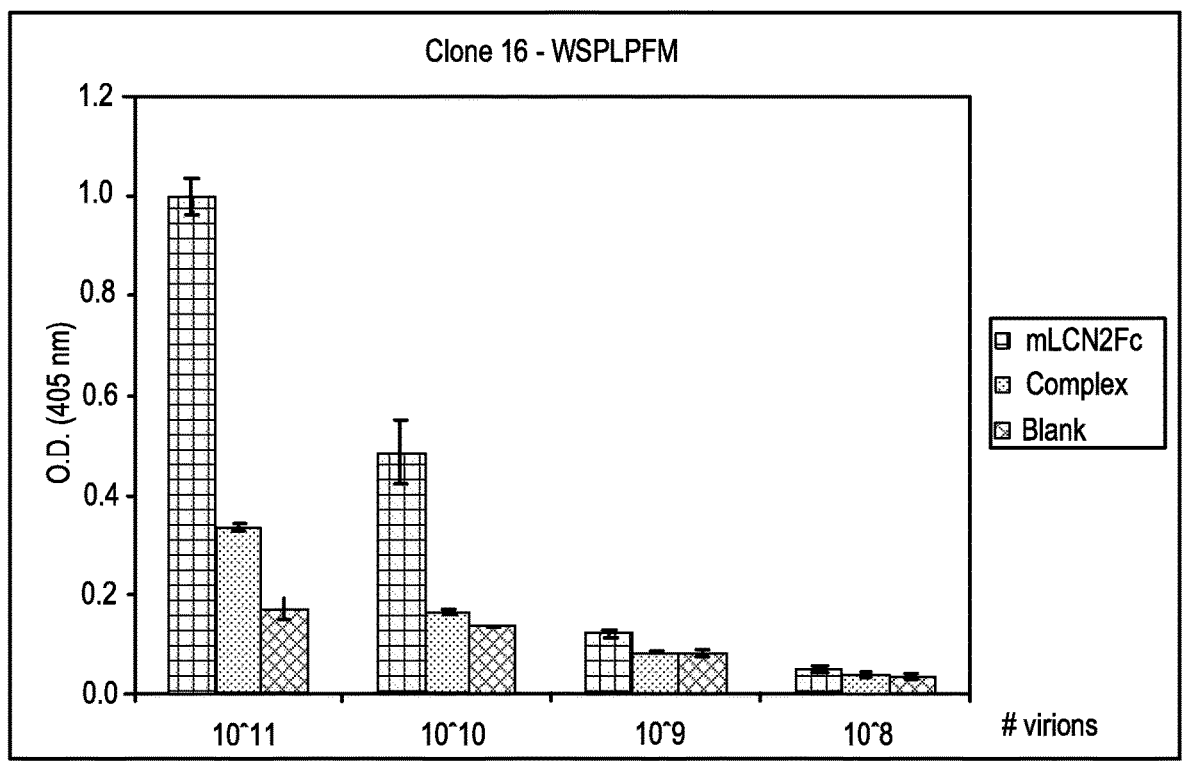

FIGS. 13A-13D: 18 min substrate incubation. Phage expressing surface-bound Peptide [sequence indicated in title bar of each graph] shows increased binding to immobilized Lcn2-Fc (left column) compared to Lcn2-Fc pre-complexed with CTLA4-Fc (middle column) or PBS control (right column) by ELISA. FIG. 13A is a graph showing clone 6—EKWFRFM (SEQ ID NO:56); FIG. 13B is a graph showing clone 8—YLELMHS (SEQ ID NO:57); FIG. 13C is a graph showing clone 12—SVLPPFM (SEQ ID NO:58); FIG. 13D is a graph showing clone 16—WSPLPFM (SEQ ID NO:59).

Figure 14A:
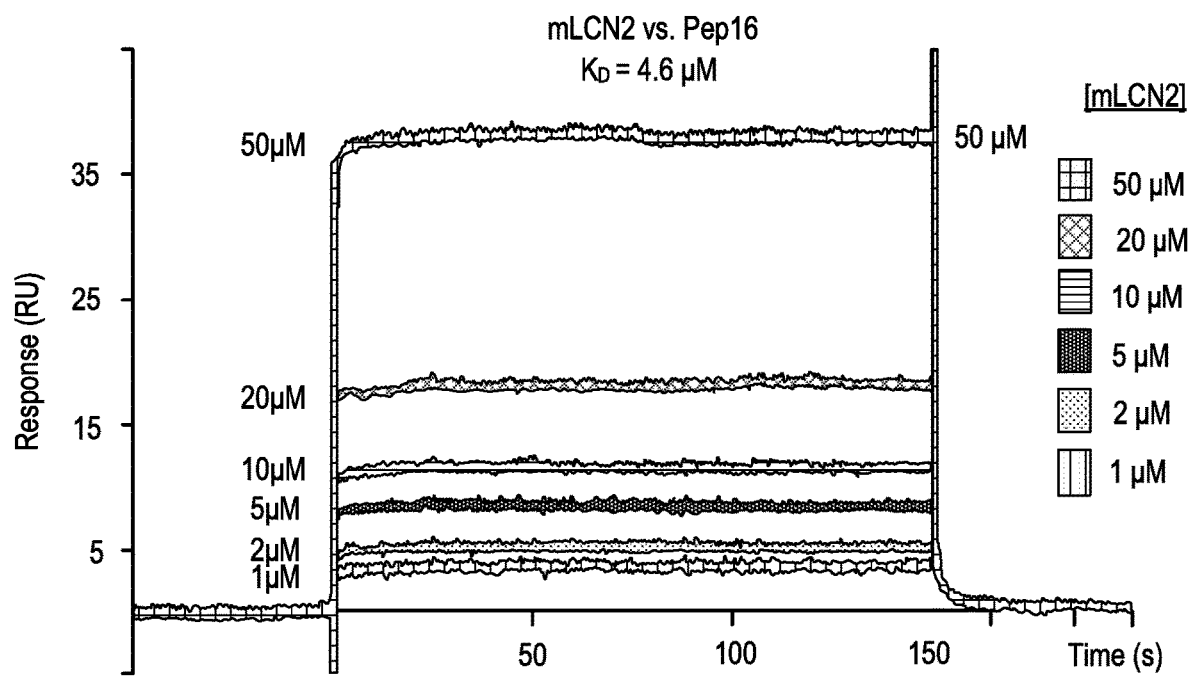
Figure 14B:
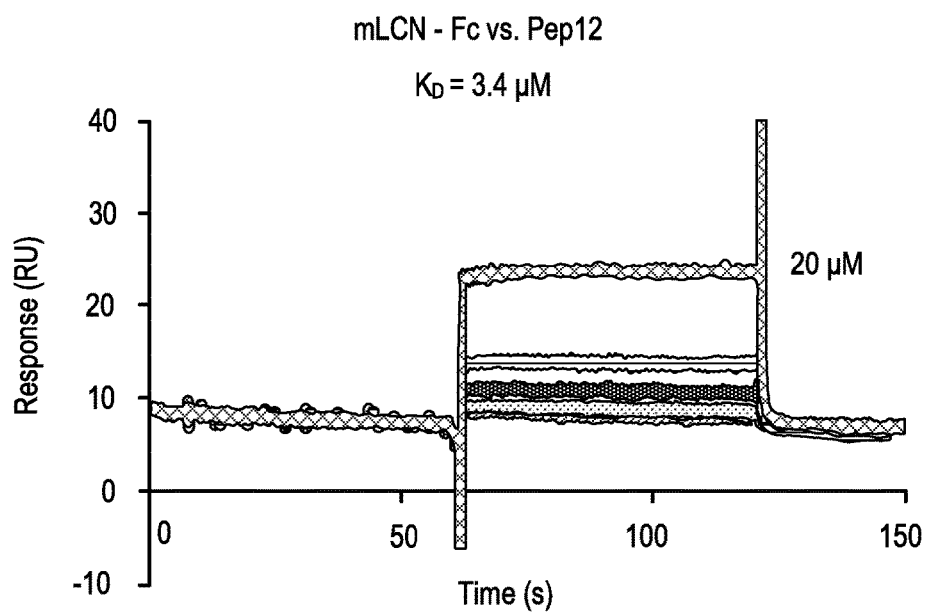
Figure 15:
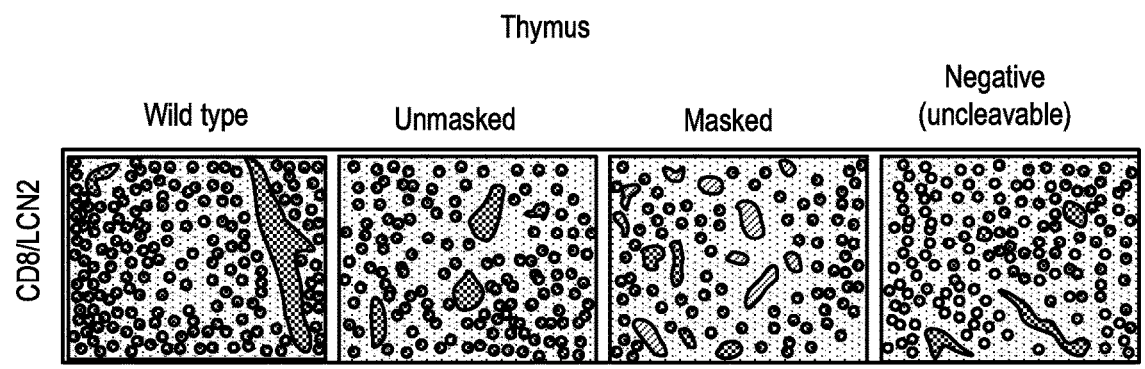

FIG. 14A: mLCN2 vs. Pep16. Surface plasmon resonance of analyte mLcn2 flowed over ligand Peptide16 immobilized to a CM5 chip. Representative results are shown from three independent experiments. $K_D$=4.6 µM FIG. 14B: mLCN2-Fc vs. Pep12. Surface plasmon resonance of analyte mLcn2-Fc flowed over ligand Peptide12 immobilized to a CM5 chip. Representative results are shown from three independent experiments. $K_D$=3.4 µM FIG. 15: Naïve mice were injected i.v. with 100 µg of indicated mtLCN2-Fc construct and tissue samples were collected 48 hr. post-dose. Cryosections were stained for CD4 or CD8 (medium gray) and human IgG (light gray) from the thymus.

Figure 16:
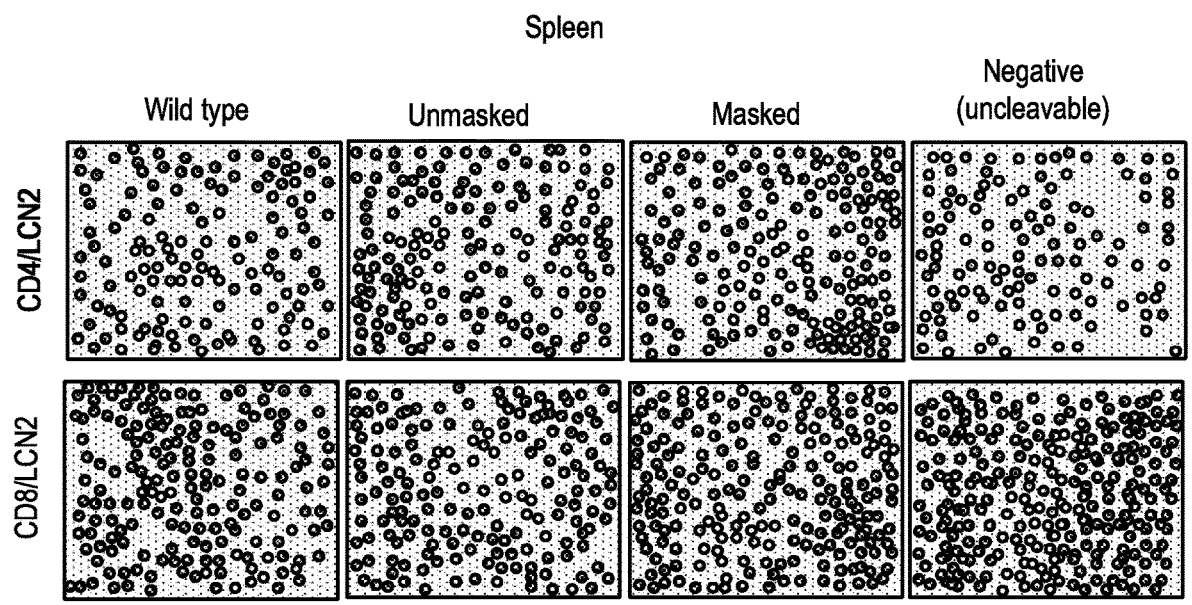

FIG. 16: Naïve mice were injected i.v. with 100 µg of indicated mtLCN2-Fc construct and tissue samples were collected 48 hr. post-dose. Cryosections were stained for CD4 or CD8 (medium gray) and human IgG (light gray) from the spleen.

Figure 17:
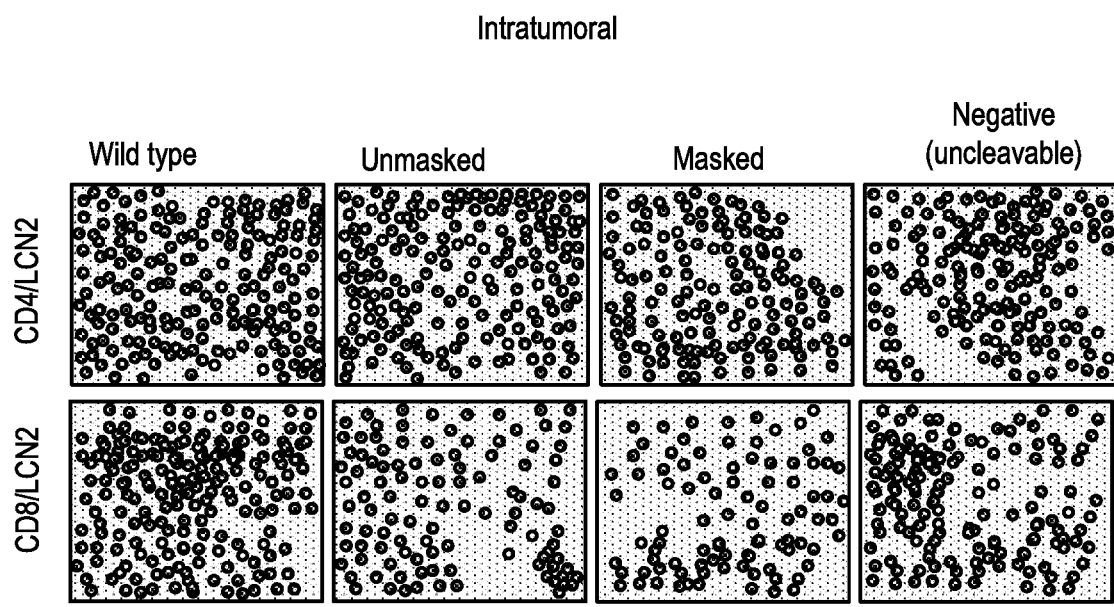

FIG. 17: Melanoma-bearing mice were injected i.v. with 100 µg of indicated mLcn2-Fc construct and tumor samples were collected 72 hr. post-dose. Cryosections were stained for CD4 or CD8 (medium gray) and human IgG (light gray). Note membrane staining of TILs by both masked and unmasked (MMP9-pretreated) mLcn2 constructs, indicating MMP9 activity in tumors. Control refers to masked mLcn2 with non-cleavable linker (Mxx9) and, as expected, shows no reactivity. 4',6-diamidino-2-phenylindole (DAPI) nuclear staining shown in dark gray.

Figure 18:
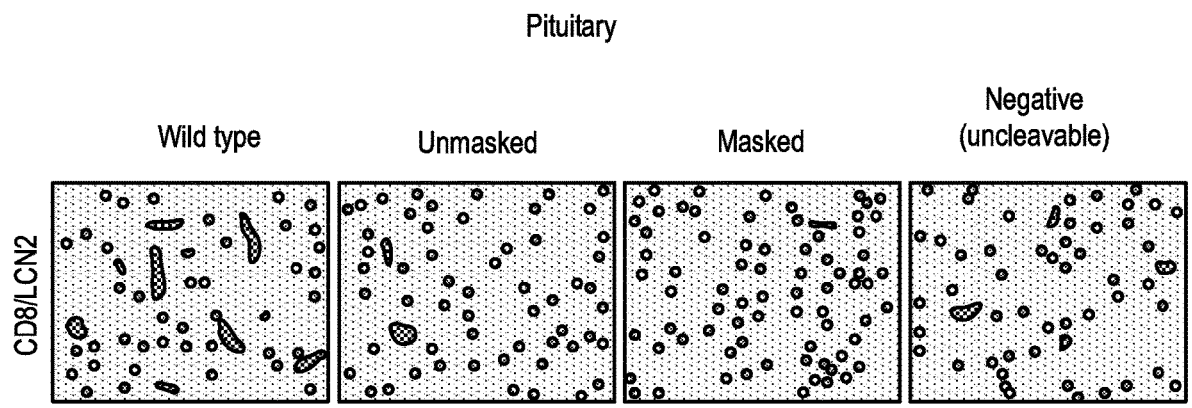

FIG. 18: Naïve mice were injected i.v. with 100 µg of indicated mLcn2-Fc construct and tissue samples were collected 48 hr. post-dose. Cryosections were stained for human IgG (light gray). Note that, in contrast to the tumor environment, the masked mLcn2-Fc did not bind to normal tissue constituents. By contrast, unmasked, MMP9 pretreated and mLcn2-Fc without N-terminal masks bound equally well to pituicytes.

Figure 19A:
Figure 19B:
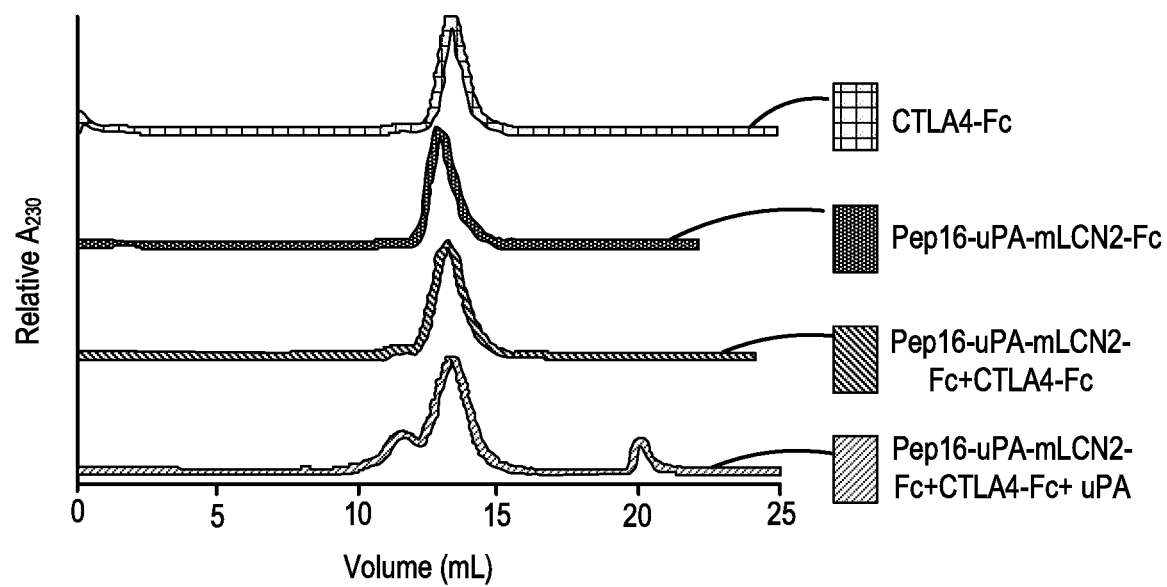

FIG. 19A-19B: Binding of Masked and Unmasked uPA-mLCN2-Fc constructs to CTLA4. FIG. 19A is a schematic showing that masked mLCN2-Fc was created such that the protease substrate was mutated to LSGRSDNH (SEQ ID NO:60), a known substrate for urokinase-type plasminogen activator (uPA). FIG. 19B is a graph showing absorbance at 230 nm. Masked uPA-mLCN2-Fc was incubated with or without recombinant uPA enzyme for 12 hr at 37° C. Reactions were mixed with CTLA4-Fc and assayed by analytical SEC.

Figure 20:
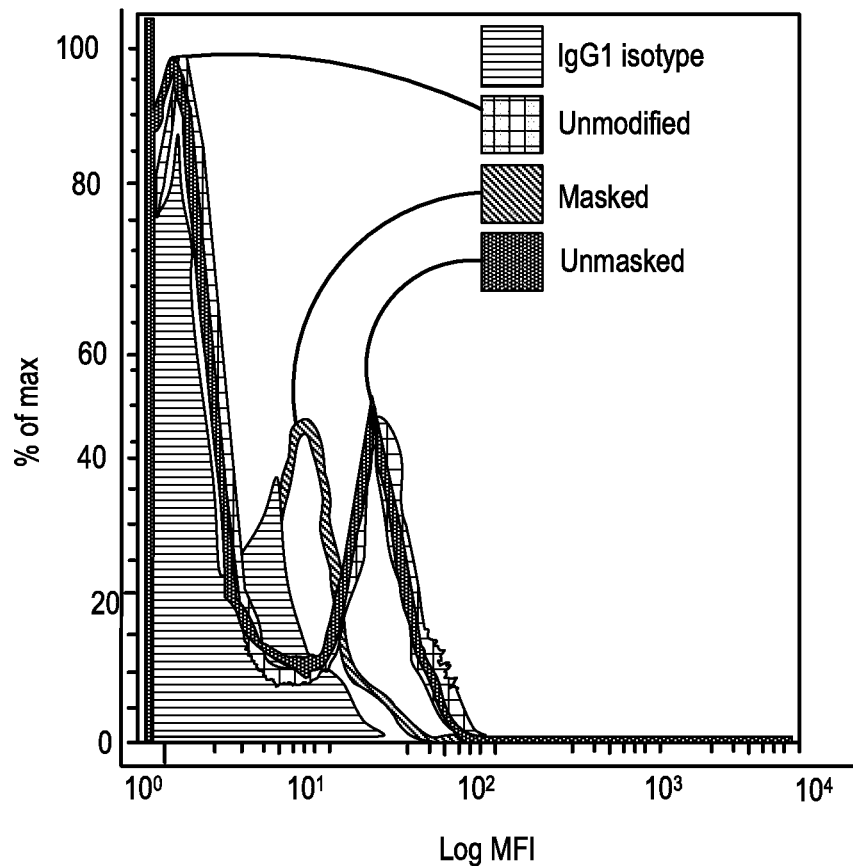

FIG. 20: Flow cytometry of CTLA4-bp-Fc constructs to human CD4+ lymphocytes. Human peripheral blood mononuclear cells (PBMC) were stained with AF647-labeled CTLA4-bp-Fc constructs or AF647-Cetuximab as an IgG1 control. Cells were analyzed by flow cytometry and gated on CD4+ cells, where AF647 mean fluorescence was recorded. Samples were performed in triplicate and representative traces are reported.

DETAILED DESCRIPTION OF THE INVENTION

Definitions

The abbreviations used herein have their conventional meaning within the chemical and biological arts. The chemical structures and formulae set forth herein are constructed according to the standard rules of chemical valency known in the chemical arts.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1-35.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the relative to the activity or function of the protein in the absence of the activator (e.g. composition described herein). Thus, in embodiments, activation may include, at least in part, partially or totally increasing stimulation, increasing or enabling activation, or activating, sensitizing, or up-regulating signal transduction or enzymatic activity or the amount of a protein decreased in a disease.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

protein).

A "ligand" refers to an agent, e.g., a polypeptide or other molecule, capable of binding to a receptor.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

The term "LCN2" or "CTLA-4 binding lipocalin 2" or "lipocalin 2" as provided herein includes any of the recombinant or naturally-occurring forms of the lipocalin 2 (LCN2) protein or variants or homologs thereof that maintain LCN2 protein activity (e.g. within at least 50%, 80%, 90%, 95%, 96%, 97%, 98%, 99% or 100% activity compared to LCN2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LCN2 polypeptide. In embodiments, the LCN2 protein is the protein as identified by the NCBI sequence reference GI:38455402, homolog or functional fragment thereof.

The term "MMP 2" or "MMP 2 protease" as provided herein includes any of the recombinant or naturally-occurring forms of the matrix metalloproteinase 2 (MMP 2) or variants or homologs thereof that maintain MMP 2 activity (e.g. within at least 50%, 80%, 90%, 95%, 96%, 97%, 98%, 99% or 100% activity compared to MMP 2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP 2 polypeptide. In embodiments, MMP 2 is the protein as identified by the NCBI sequence reference GI:189217853, homolog or functional fragment thereof.

The term "MMP9" or "MMP9 protease" as provided herein includes any of the recombinant or naturally-occurring forms of the matrix metalloproteinase 9 (MMP9) or variants or homologs thereof that maintain MMP9 activity (e.g. within at least 50%, 80%, 90%, 95%, 96%, 97%, 98%, 99% or 100% activity compared to MMP 9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP9 polypeptide. In embodiments, MMP9 is the protein as identified by the NCBI sequence reference GI:74272287, homolog or functional fragment thereof.

The term "MMP 13" or "MMP 13 protease" as provided herein includes any of the recombinant or naturally-occurring forms of the matrix metalloproteinase 13 (MMP 13) or variants or homologs thereof that maintain MMP 13 activity (e.g. within at least 50%, 80%, 90%, 95%, 96%, 97%, 98%, 99% or 100% activity compared to MMP 13). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP 13 polypeptide. In embodiments, MMP 13 is the protein as identified by the NCBI sequence reference GI:4505209, homolog or functional fragment thereof.

The term "ADAM 9" or "ADAM 9 protease" as provided herein includes any of the recombinant or naturally-occurring forms of the disintegrin and metalloprotease domain-containing (ADAM) protein 9 or variants or homologs thereof that maintain ADAM 9 activity (e.g. within at least 50%, 80%, 90%, 95%, 96%, 97%, 98%, 99% or 100% activity compared to ADAM 9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 9 polypeptide. In embodiments, ADAM 9 is the protein as identified by the NCBI sequence reference GI:4501915, homolog or functional fragment thereof.

The term "ADAM 10" or "ADAM 10 protease" as provided herein includes any of the recombinant or naturally-occurring forms of the disintegrin and metalloprotease domain-containing (ADAM) protein 10 or variants or homologs thereof that maintain ADAM 10 activity (e.g. within at least 50%, 80%, 90%, 95%, 96%, 97%, 98%, 99% or 100% activity compared to ADAM 10). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 10 polypeptide. In embodiments, ADAM 10 is the protein as identified by the NCBI sequence reference GI:4557251, homolog or functional fragment thereof.

The term "ADAM 17" or "ADAM 17 protease" as provided herein includes any of the recombinant or naturally-occurring forms of the disintegrin and metalloprotease domain-containing (ADAM) protein 17 or variants or homologs thereof that maintain ADAM 17 activity (e.g. within at least 50%, 80%, 90%, 95%, 96%, 97%, 98%, 99% or 100% activity compared to ADAM 17). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 17 polypeptide. In embodiments, ADAM 17 is the protein as identified by the NCBI sequence reference GI:73747889, homolog or functional fragment thereof.

The term "PSA" or "PSA protease" as provided herein includes any of the recombinant or naturally-occurring forms of the prostate-specific antigen (PSA), also known as gamma seminoprotein or kallikrein-3, or variants or homologs thereof that maintain PSA activity (e.g. within at least 50%, 80%, 90%, 95%, 96%, 97%, 98%, 99% or 100% activity compared to PSA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PSA polypeptide. In embodiments, PSA is the protein as identified by the NCBI sequence reference GI:71834853, homolog or functional fragment thereof.

The term "PSMA" or "PSMA protease" as provided herein includes any of the recombinant or naturally-occurring forms of the prostate-specific membrane antigen (PSMA), also known as glutamate carboxypeptidase II (GCPII), N-acetyl-L-aspartyl-L-glutamate peptidase I (NAALADase I) or NAAG peptidase, or variants or homologs thereof that maintain PSMA activity (e.g. within at least 50%, 80%, 90%, 95%, 96%, 97%, 98%, 99% or 100% activity compared to PSMA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PSMA polypeptide. In embodiments, PSMA is the protein as identified by the NCBI sequence reference GI:62548858, homolog or functional fragment thereof.

The term "Cathepsin B" or "Cathepsin B protease" as provided herein includes any of the recombinant or naturally-occurring forms of the Cathepsin B protein or variants or homologs thereof that maintain Cathepsin B activity (e.g. within at least 50%, 80%, 90%, 95%, 96%, 97%, 98%, 99% or 100% activity compared to Cathepsin B). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cathepsin B polypeptide. In embodiments, Cathepsin B is the protein as identified by the NCBI sequence reference GI:4503139, homolog or functional fragment thereof.

The term "fibroblast associated protein" as provided herein includes any of the recombinant or naturally-occurring forms of the fibroblast associated protein or variants or homologs thereof that maintain fibroblast associated protein activity (e.g. within at least 50%, 80%, 90%, 95%, 96%, 97%, 98%, 99% or 100% activity compared to fibroblast associated protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring fibroblast associated protein polypeptide. In embodiments, fibroblast associated protein is the protein as identified by the NCBI sequence reference GI:1888316, homolog or functional fragment thereof.

The term "uPA" or "uPA protease" as provided herein includes any of the recombinant or naturally-occurring forms of the urokinase-type plasminogen activator (uPA) protease, or variants or homologs thereof that maintain uPA protease activity (e.g. within at least 50%, 80%, 90%, 95%, 96%, 97%, 98%, 99% or 100% activity compared to uPA protease). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring uPA polypeptide. In embodiments, uPA protease is the protein as identified by the UniProt sequence reference P00749, homolog or functional fragment thereof.

The term "MT-SP1" or "MT-SP1 protease" as provided herein includes any of the recombinant or naturally-occurring forms of the membrane type serine protease 1 (MT-SP1) or variants or homologs thereof that maintain MT-SP1 activity (e.g. within at least 50%, 80%, 90%, 95%, 96%, 97%, 98%, 99% or 100% activity compared to MT-SP1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MT-SP1 polypeptide. In embodiments, MT-SP1 is the protein as identified by the NCBI sequence reference GI:11415040, homolog or functional fragment thereof.

The term "legumain" or "legumain protease" as provided herein includes any of the recombinant or naturally-occurring forms of the legumain protein or variants or homologs thereof that maintain legumain activity (e.g. within at least 50%, 80%, 90%, 95%, 96%, 97%, 98%, 99% or 100% activity compared to legumain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring legumain polypeptide. In embodiments, legumain is the protein as identified by the NCBI sequence reference GI:2842759, homolog or functional fragment thereof.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a cleavable peptide linker as described herein and a protease. In embodiments contacting includes, for example, allowing a recombinant CTLA-4 binding protein described herein to interact with a CTLA-4 protein.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, Herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

Recombinant Proteins

Provided herein are recombinant CTLA-4 binding proteins and recombinant CTLA-4 binding protein dimers useful, inter alia, for the treatment of cancer. A recombinant CTLA-4 binding protein or recombinant CTLA-4 binding protein dimer as provided herein including embodiments thereof, includes a domain (CTLA-4 binding domain) capable of interacting with (e.g., binding to) a CTLA-4 protein expressed on the surface of a cell (e.g., a cancer cell). The CTLA-4 binding domain is connected to a peptide (CTLA-4 binding domain masking peptide) through a linker (cleavable peptide linker) such that the CTLA-4 binding domain masking peptide prevents the CTLA-4 binding domain from binding to a CTLA-4 protein. Upon hydrolysis (proteolytic cleavage) of the cleavable peptide linker, the CTLA-4 binding domain masking peptide is released thereby allowing the CTLA-4 binding domain to interact with a CTLA-4 protein. Thus, in a first aspect, there is provided a recombinant CTLA-4 binding protein including (i) a CTLA-4 binding domain; (ii) a CTLA-4 binding domain masking peptide; and (iii) a cleavable peptide linker connecting the CTLA-4 binding domain masking peptide to the CTLA-4 binding domain.

CTLA-4 Binding Domains

The term "CTLA-4 binding protein" as provided herein refers to a recombinantly expressed polypeptide capable of binding to, or otherwise exhibiting an affinity for, a CTLA-4 protein found in or on a cell. The CTLA-4 binding protein provided herein including embodiments thereof includes a CTLA-4 binding domain, a CTLA-4 binding domain masking peptide and a cleavable peptide linker, which connects the CTLA-4 binding domain masking peptide to the CTLA-4 binding domain. The term "CTLA-4 binding domain" refers to a recombinantly expressed polypeptide domain capable of binding to, or otherwise exhibiting an affinity for, a CTLA-4 protein found in or on a cell. Methods for determining the extent of binding of a CTLA-4 binding domain to CTLA-4 are well known in the art. The CTLA-4 binding domain provided herein may be a LCN2 protein capable of binding to CTLA-4. Thus, in embodiments, the CTLA-4 binding domain is a CTLA-4 binding lipocalin 2 (LCN2). In embodiments, the CTLA-4 binding domain includes a CTLA-4 binding lipocalin 2 (LCN2). In embodiments, the CTLA-4 binding domain includes the sequence of SEQ ID NO:34. In embodiments, the CTLA-4 binding domain has the sequence of SEQ ID NO:34. In embodiments, the CTLA-4 binding LCN2 has the sequence of any one of the LCN2 proteins disclosed in patent application Applicants 2014/0051645 A1 and Applicants 2014/0080177, which are hereby incorporated by reference in their entirety and for all purposes.

CTLA-4 Binding Domain Masking Peptides

A CTLA-4 binding domain masking peptide as provided herein refers to a peptide capable of binding to, or otherwise exhibiting an affinity for, a CTLA-4 binding domain. When non-covalently bound to the CTLA-4 binding domain, the CTLA-4 binding domain masking peptide inhibits (e.g. decreases) or otherwise prevents (masks) the activity or binding of the CTLA-4 binding domain to its cognate receptor or protein (i.e., CTLA-4). The CTLA-4 binding domain masking peptide exhibits sufficient affinity for the CTLA-4 binding domain to prevent the activity or binding of the CTLA-4 binding domain to a CTLA-4 protein. Methods for determining the extent of binding of a CTLA-4 binding domain to a CTLA-4 protein are well known in the art.

In embodiments, the CTLA-4 binding domain masking peptide has a length of at least 4 amino acids. In embodiments, the CTLA-4 binding domain masking peptide is a circular peptide. In embodiments, the circularized peptide is a 12-mer. Where the CTLA-4 binding domain masking peptide is a circularized peptide, a circularized peptide is formed by a di-sulfide bond connecting two cysteine amino acid residues. In some embodiments, the cysteine amino acid residues are terminal cysteines (i.e., are located at the N-terminus and/or the C-terminus of the CTLA-4 binding domain masking peptide). In embodiments, the di-sulfide bond connects an N-terminal cysteine with a C-terminal cysteine.

In embodiments, the CTLA-4 binding domain masking peptide includes a sequence having about 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has about 90% homology to SEQ ID NO:1. In embodiments, the sequence has about 90% homology to SEQ ID NO:2. In embodiments, the sequence has about 90% homology to SEQ ID NO:3. In embodiments, the sequence has about 90% homology to SEQ ID NO:4. In embodiments, the sequence has about 90% homology to SEQ ID NO:5. In embodiments, the sequence has about 90% homology to SEQ ID NO:6. In embodiments, the sequence has about 90% homology to SEQ ID NO:7. In embodiments, the sequence has about 90% homology to SEQ ID NO:8. In embodiments, the sequence has about 90% homology to SEQ ID NO:9. In embodiments, the sequence has about 90% homology to SEQ ID NO:10. In embodiments, the sequence has about 90% homology to SEQ ID NO:11. In embodiments, the sequence has about 90% homology to SEQ ID NO:12. In embodiments, the sequence has about 90% homology to SEQ ID NO:13. In embodiments, the sequence has about 90% homology to SEQ ID NO:14.

In embodiments, the sequence has at least 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has at least 90% homology to SEQ ID NO:1. In embodiments, the sequence has at least 90% homology to SEQ ID NO:2. In embodiments, the sequence has at least 90% homology to SEQ ID NO:3. In embodiments, the sequence has at least 90% homology to SEQ ID NO:4. In embodiments, the sequence has at least 90% homology to SEQ ID NO:5. In embodiments, the sequence has at least 90% homology to SEQ ID NO:6. In embodiments, the sequence has at least 90% homology to SEQ ID NO:7. In embodiments, the sequence has at least 90% homology to SEQ ID NO:8. In embodiments, the sequence has at least 90% homology to SEQ ID NO:9. In embodiments, the sequence has at least 90% homology to SEQ ID NO:10. In embodiments, the sequence has at least 90% homology to SEQ ID NO:11. In embodiments, the sequence has at least 90% homology to SEQ ID NO:12. In embodiments, the sequence has at least 90% homology to SEQ ID NO:13. In embodiments, the sequence has at least 90% homology to SEQ ID NO:14.

In embodiments, the sequence has at least 80% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has at least 80% homology to SEQ ID NO:1. In embodiments, the sequence has at least 80% homology to SEQ ID NO:2. In embodiments, the sequence has at least 80% homology to SEQ ID NO:3. In embodiments, the sequence has at least 80% homology to SEQ ID NO:4. In embodiments, the sequence has at least 80% homology to SEQ ID NO:5. In embodiments, the sequence has at least 80% homology to SEQ ID NO:6. In embodiments, the sequence has at least 80% homology to SEQ ID NO:7. In embodiments, the sequence has at least 80% homology to SEQ ID NO:8. In embodiments, the sequence has at least 80% homology to SEQ ID NO:9. In embodiments, the sequence has at least 80% homology to SEQ ID NO:10. In embodiments, the sequence has at least 80% homology to SEQ ID NO:11. In embodiments, the sequence has at least 80% homology to SEQ ID NO:12. In embodiments, the sequence has at least 80% homology to SEQ ID NO:13. In embodiments, the sequence has at least 80% homology to SEQ ID NO:14.

In embodiments, the sequence has at least 70% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has at least 70% homology to SEQ ID NO:1. In embodiments, the sequence has at least 70% homology to SEQ ID NO:2. In embodiments, the sequence has at least 70% homology to SEQ ID NO:3. In embodiments, the sequence has at least 70% homology to SEQ ID NO:4. In embodiments, the sequence has at least 70% homology to SEQ ID NO:5. In embodiments, the sequence has at least 70% homology to SEQ ID NO:6. In embodiments, the sequence has at least 70% homology to SEQ ID NO:7. In embodiments, the sequence has at least 70% homology to SEQ ID NO:8. In embodiments, the sequence has at least 70% homology to SEQ ID NO:9. In embodiments, the sequence has at least 70% homology to SEQ ID NO:10. In embodiments, the sequence has at least 70% homology to SEQ ID NO:11. In embodiments, the sequence has at least 70% homology to SEQ ID NO:12. In embodiments, the sequence has at least 70% homology to SEQ ID NO:13. In embodiments, the sequence has at least 70% homology to SEQ ID NO:14.

In embodiments, the sequence has at least 60% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has at least 60% homology to SEQ ID NO:1. In embodiments, the sequence has at least 60% homology to SEQ ID NO:2. In embodiments, the sequence has at least 60% homology to SEQ ID NO:3. In embodiments, the sequence has at least 60% homology to SEQ ID NO:4. In embodiments, the sequence has at least 60% homology to SEQ ID NO:5. In embodiments, the sequence has at least 60% homology to SEQ ID NO:6. In embodiments, the sequence has at least 60% homology to SEQ ID NO:7. In embodiments, the sequence has at least 60% homology to SEQ ID NO:8. In embodiments, the sequence has at least 60% homology to SEQ ID NO:9. In embodiments, the sequence has at least 60% homology to SEQ ID NO:10. In embodiments, the sequence has at least 60% homology to SEQ ID NO:11. In embodiments, the sequence has at least 60% homology to SEQ ID NO:12. In embodiments, the sequence has at least 60% homology to SEQ ID NO:13. In embodiments, the sequence has at least 60% homology to SEQ ID NO:14.

In embodiments, the sequence is SEQ ID NO:1, In embodiments, the sequence is SEQ ID NO:2, In embodiments, the sequence is SEQ ID NO:3, In embodiments, the sequence is SEQ ID NO:4, In embodiments, the sequence is SEQ ID NO:5, In embodiments, the sequence is SEQ ID NO:6, In embodiments, the sequence is SEQ ID NO:7, In embodiments, the sequence is SEQ ID NO:8, In embodiments, the sequence is SEQ ID NO:9, In embodiments, the sequence is SEQ ID NO:10, In embodiments, the sequence is SEQ ID NO:11, In embodiments, the sequence is SEQ ID NO:12, In embodiments, the sequence is SEQ ID NO:13, In embodiments, the sequence is SEQ ID NO:14.

In embodiments, the sequence has about 70%, 75%, 80%, 85%, 90%, 91%, 92%, 93%, 94%, 95%, 96%, 97%, 98%, 99% or 100% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

Glycoprotein Secretion Signals

Further to the recombinant CTLA-4 binding protein disclosed above, in embodiments the CTLA-4 binding domain masking peptide includes a glycoprotein secretion signal. The term "glycoprotein" as provided herein is well known in the art and refers to proteins that contain oligosaccharide chains (glycans) covalently attached thereto (e.g. to polypeptide side-chains). The carbohydrate may be attached to the protein in a cotranslational or posttranslational modification, a process known as glycosylation. Glycoproteins are often important integral membrane proteins and secreted proteins. Nonlimiting examples of glycoproteins include antibodies, major histocompatibility complex (MHC) molecules, mucins, integrins, structural glycoproteins, viral coat proteins (e.g., gp41, gp120), and hormones (e.g., follicle-stimulating hormone, thyroid-stimulating hormone, erythropoietin. A "glycoprotein secretion signal" as provided herein refers to an amino acid sequence included in a glycoprotein that increases secretion, which is typically cleaved from the nascent glycoprotein once it has been translocated into the membrane of the endoplasmic reticulum by a signal peptidase. In embodiments, the glycoprotein secretion signal is a glycoprotein (gp) 67 secretion signal, pELB signal, human granulocyte-macrophage colonystimulating factor receptor (GM-CSFR), or an alpha-chain signal sequence (CAR). In embodiments, the glycoprotein secretion signal is a glycoprotein (gp) 67 secretion signal. In embodiments, the glycoprotein (gp) 67 secretion signal includes the sequence of SEQ ID NO:35. In embodiments, the glycoprotein (gp) 67 secretion signal has the sequence of SEQ ID NO:35. In embodiments, the glycoprotein secretion signal is a pELB signal. A pE1B signal sequence is involved in the periplasmic expression of proteins in *E. coli*. The pE1B signal sequence is involved in the expression, proper folding, disulfide formation, and solubility of proteins. In embodiments, the pELB signal includes the sequence MKYLLPTAAAGLLLLAAQPAMA (SEQ ID NO:44). In embodiments, the pELB signal is the sequence MKYLLPTAAAGLLLLAAQPAMA (SEQ ID NO:44). In embodiments, the glycoprotein secretion signal is a human granulocyte-macrophage colony-stimulating factor receptor (GM-CSFR). In embodiments, the GM-CSFR includes the sequence MLLLVTSLLLCELPHP AFLLI (SEQ ID NO:45). In embodiments, the GM-CSFR is the sequence MLLL VTSLLLCELPHP AFLLI (SEQ ID NO:45). In embodiments, the glycoprotein secretion signal is an alpha-chain signal sequence (CAR). In embodiments, the CAR sequence includes the sequence MPPPRLLFFL (SEQ ID NO:61). In embodiments, the CAR sequence is the sequence MPPPRLLFFL (SEQ ID NO:61).

Cleavable Peptide Linkers

A "cleavable peptide linker" as used herein refers to a polyvalent linker covalently bonded to a CTLA-4 binding domain and covalently bonded to a CTLA-4 binding domain masking peptide which is enzymatically cleavable (e.g. at a cleavage site). In embodiments the cleavable peptide linker is recombinantly expressed. In embodiments, the cleavable peptide linker is a linker formed by reacting a functional (reactive) group attached to the linker with a CTLA-4 binding domain masking peptide using, for example, conjugate chemistry. In embodiments, the cleavable peptide linker is a linker formed by reacting a functional (reactive) group attached to the linker with a CTLA-4 binding domain using, for example, conjugate chemistry. In embodiments, the cleavable peptide linker connects the CTLA-4 binding domain masking peptide to the N-terminus of the CTLA-4 binding domain. In embodiments, the cleavable peptide linker connects the CTLA-4 binding domain masking peptide to the C-terminus of the CTLA-4 binding domain. In embodiments, the cleavable peptide linker is a flexible linker including one or more glycine residues. In embodiments, at least half of the residues included in the cleavable peptide linker are glycine residues. In embodiments, the cleavable peptide linker includes a glycine-glycine-serine sequence.

The terms "conjugate" and "conjugate chemistry" refer to reactions with known reactive groups which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(i) metal silicon oxide bonding; and (l) metal bonding to reactive phosphorus groups (e.g. phosphines) to form, for example, phosphate diester bonds.

The reactive functional groups can be chosen such that they do not participate in, or interfere with, the chemical stability of the compositions described herein. Alternatively, a reactive functional group can be protected from participating in the crosslinking reaction by the presence of a protecting group.

Described herein are 'antibody prodrugs' that use tumor-associated properties to activate a modified mAb at a disease site. Discovered herein, a non-covalent recombinant masking protein (e.g. mAb mask), when integrated with clinically validated mAbs or mAb-like biologics (i.e. recombinant ligand proteins described herein), reduces the validated mAb's affinity or occludes its antigen binding site in normal tissue but becomes activated at the tumor by tumor-specific proteases.

The cleavable peptide linker provided herein may include a protease cleavage site. A "cleavage site" as used herein, refers to a recognizable site for cleavage of a portion of a linker (e.g. cleavable peptide linker as described hereinabove) found in a recombinant CTLA-4 binding protein or recombinant CTLA-4 binding protein dimer described herein. Thus, a cleavage site may be found in the sequence of a cleavable peptide linker as described herein, including embodiments thereof. In embodiments, the cleavage site is an amino acid sequence that is recognized and cleaved by a cleaving agent (e.g. a peptidyl sequence). Exemplary cleaving agents include proteins, enzymes, DNAzymes, RNAzymes, metals, acids, and bases. Exemplary cleavage sites are defined herein (e.g., Table 1 and FIG. 6).

In embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP 9 cleavage site, a MMP 13 cleavage site or a MMP 2 cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site. Protease cleavage sites may be designated by a specific amino acid sequence. Exemplary protease cleavage substrate sequences are shown in Table 1, below.

In embodiments, cleavable peptide linkers are 5-mers (i.e. peptides 5 amino acids in length), 6-mers (i.e. peptides 6 amino acids in length), 7-mers (i.e. peptides 7 amino acids in length), 8-mers (i.e. peptides 8 amino acids in length), 9-mers (i.e. peptides 9 amino acids in length), 10-mers (i.e. peptides 10 amino acids in length), 11-mers (i.e. peptides11 amino acids in length), 12-mers (i.e. peptides 12 amino acids in length), or 13-mers (i.e. peptides 13 amino acids in length).

Dimerizing Domains

Further to any embodiment disclosed above, in embodiments the CTLA-4 binding domain is covalently attached to a dimerizing domain. A dimerizing domain is a protein domain capable of dimerizing (i.e. binding to a second dimerizing protein). The dimerization is typically through non-covalent binding. In embodiments, the CTLA-4 binding domain is covalently attached to the C-terminus of the dimerizing domain. In embodiments, the CTLA-4 binding domain is covalently attached to the N-terminus of the dimerizing domain.

In embodiments, more than one CTLA-4 binding proteins are covalently attached to a dimerizing domain. In embodiments, a first CTLA-4 binding protein is attached to the C-terminus of the dimerizing domain and a second CTLA-4 binding protein is attached to the N-terminus of the dimerizing domain.

The dimerizing domain may be an Fc protein domain. The Fc protein domain may be an IgG or IgM Fc protein. In embodiments, the Fc protein is an IgG Fc protein. The IgG Fc protein may be an IgG$_1$ Fc protein. In embodiments, the IgG$_1$ Fc protein has a molecular weight of about 5 kDa, 10 kDa, 15 kDa, 20 kDa, 25 kDa, 30 kDa, 35 kDa, 40 kDa, 45 kDa, 50 kDa, 55 kDa, 60 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, or 170 kDa. The IgG$_1$ Fc protein may have a molecular weight of about 30 kDa to about 70 kDa. The IgG$_1$ Fc protein may have a molecular weight of about 40 kDa to about 60 kDa. In embodiments, the Fc protein is an IgM Fc protein. The dimerizing domain may be a multivalent protein domain (e.g. preferably dimeric, but also trimeric and tetrameric protein domains). The dimerizing domain may be a nanoparticle. In embodiments, the dimerizing domain includes any of the proteins disclosed in Applicants U.S. Pat. No. 6,277,375, which is herewith incorporated in its entirety and for all purposes. In embodiments, the dimerizing domain includes any of the proteins disclosed in Nimmerjahn F et al. (Cancer Immunity (2012) Vol:12 p. 13) and Vidarsson G et al. (Forntiers in Immunology (2014) Vol:5/520), which are herewith incorporated in their entirety and for all purposes.

Further to any embodiment disclosed above, in embodiments CTLA-4 binding protein is covalently attached to a targeting domain. In embodiments, the targeting domain is covalently attached to the CTLA-4 binding domain. In embodiments, the targeting domain is covalently attached to the dimerizing domain. A "targeting domain" as provided herein is a monovalent composition capable of binding to, or otherwise exhibiting an affinity for, a particular type of tissue or component thereof. The addition of a targeting domain to a recombinant CTLA-4 binding protein as provided herein, can direct the recombinant CTLA-4 binding protein to particular sites within the body. Targeting domains may include, for example, proteins, antibodies, antibody fragments, peptides, carbohydrates, lipids, oligonucleotides, DNA, RNA, or small molecules having a molecular weight less than 2000 Daltons. In embodiments, a targeting domain is a single-chain variable fragment (scFv) domain as described herein. For example, a targeting domain may be a glycoprotein or receptor capable of selectively recognizing and binding to a corresponding ligand on a cell (e.g, tumor cell). The targeting domain may be a pair of identical proteins (e.g. 1-1 (dimer) or 2-2(tetramer)) and, in embodiments, antibody Fc domains or regions (e.g. full length or fragments of IgG Fc or IgM Fc). The targeting domain may be a cellular protein binding domain (e.g. a full length or functional fragment of a cellular protein recognized or otherwise bound by a particular cellular protein domain as described herein, including embodiments thereof). In embodiments, the targeting domain is an antibody. In embodiments, the targeting domain is a single-chain variable fragment (scFv). In embodiments, the targeting domain is a monoclonal antibody (mAb). The mAb may be a therapeutic monoclonal antibody. The mAb may be an mAb that recognizes a cellular protein domain as described herein, including embodiments thereof. In embodiments, the mAb is ipilimumab, engineered recombinant lipocalin2, cetuximab, trastuzumab, efalizumab, Etanercept, Adalimumab, Bevacizumab, Gemtuzumab, Infliximab, Natalizumab, Ofatumumab, Panitumumab, Rituximab, Tocilizumab, Abciximab, Ustekinumab, Pertuzumab, or Alemtuzumab. In embodiments, the targeting domain is a recombinant single domain protein (e.g., affibody molecule).

In embodiments, the targeting domain is an albumin-binding peptide. In embodiments, the targeting domain increases the half life of the CTLA-4 binding protein provided herein including embodiments thereof. Where the targeting domain increases the half life of the CTLA-4 binding protein, the half life of the CTLA-4 binding protein is longer in the presence of a targeting domain compared to absence of a targeting domain. In embodiments, the targeting domain includes any of the proteins disclosed in Applicants U.S. Pat. No. 6,277,375, which is herewith incorporated in its entirety and for all purposes.

In embodiments the recombinant CTLA-4 binding protein is recombinantly expressed. A CTLA-4 binding protein may have the formula:

CBDMP-CPL-CBD     (I).

Figure 2A:
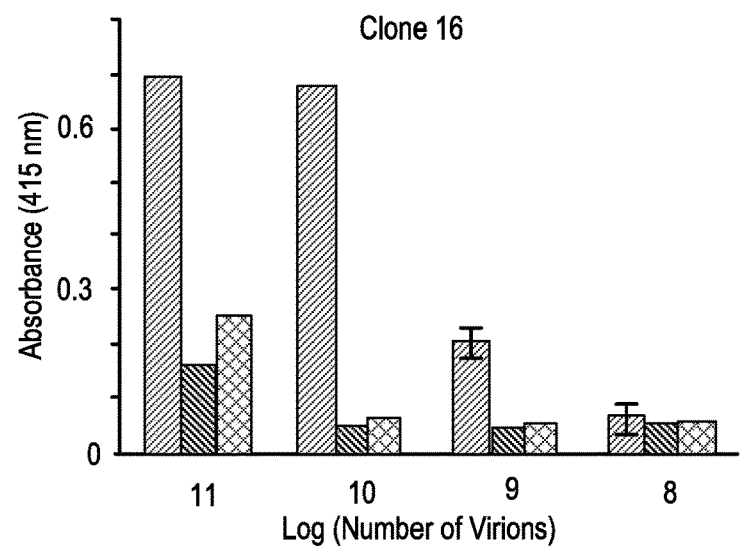
FIGS. 2A and 2B: Identification and characterization of a peptide (CTLA-4 binding domain masking peptide) blocking binding of mLcn2 (CTLA-4 binding domain) to CTLA-4.
Figure 2B:
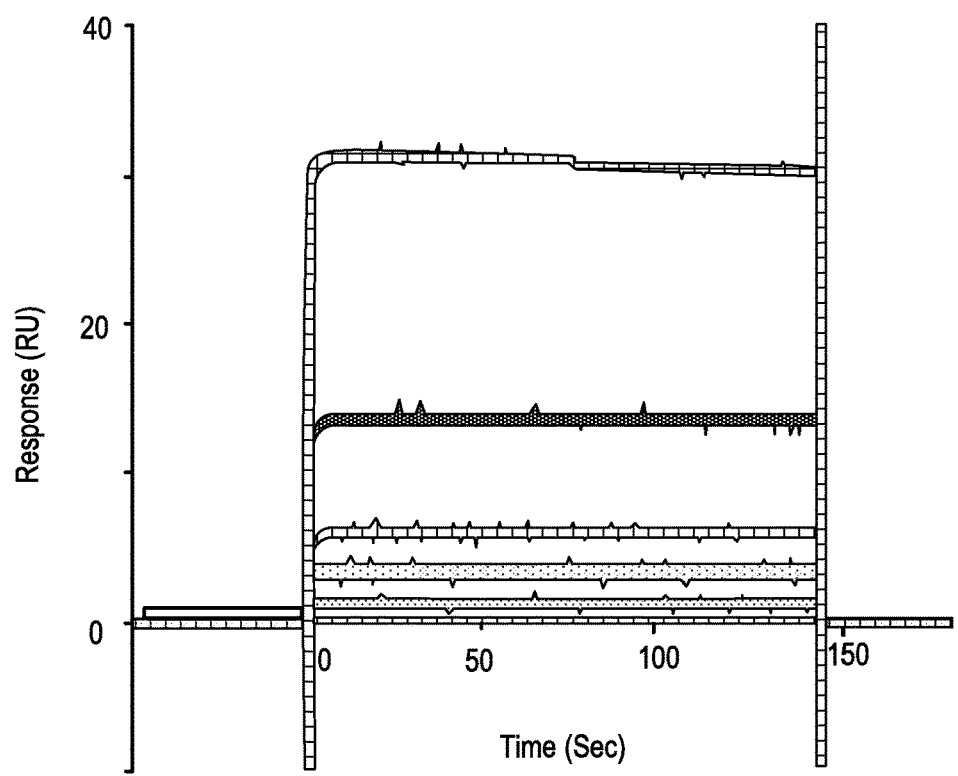

In Formula (I), CBD is a CTLA-4 binding domain as provided herein (e.g., CTLA-4 binding LCN2), CPL is a cleavable peptide linker as provided herein (e.g., an MMP 9 or μPA cleavage site), and CBDMP is a CTLA-4 binding domain masking peptide as provided herein (e.g., a peptide of SEQ ID NO:9 or 12). In embodiments, the C-terminus of CBDMP is connected to the N-terminus of CPL and the C-terminus of CPL is connected to the N-terminus of CBD. In other embodiments, the C-terminus of CBD is connected to the N-terminus of CPL and the C-terminus of CPL is connected to the N-terminus of CBDMP. FIGS. 2 and 7 set forth exemplary recombinant CTLA-4 binding proteins having exemplary CTLA-4 binding domains, cleavable peptide linkers and CTLA-4 binding domain masking peptides. In embodiments, the recombinant CTLA-4 binding protein of formula (I) is covalently attached to a targeting domain.

Where the recombinant CTLA-4 binding protein is covalently attached to a dimerizing domain, the CTLA-4 binding protein may have the formula:

Figure 1:
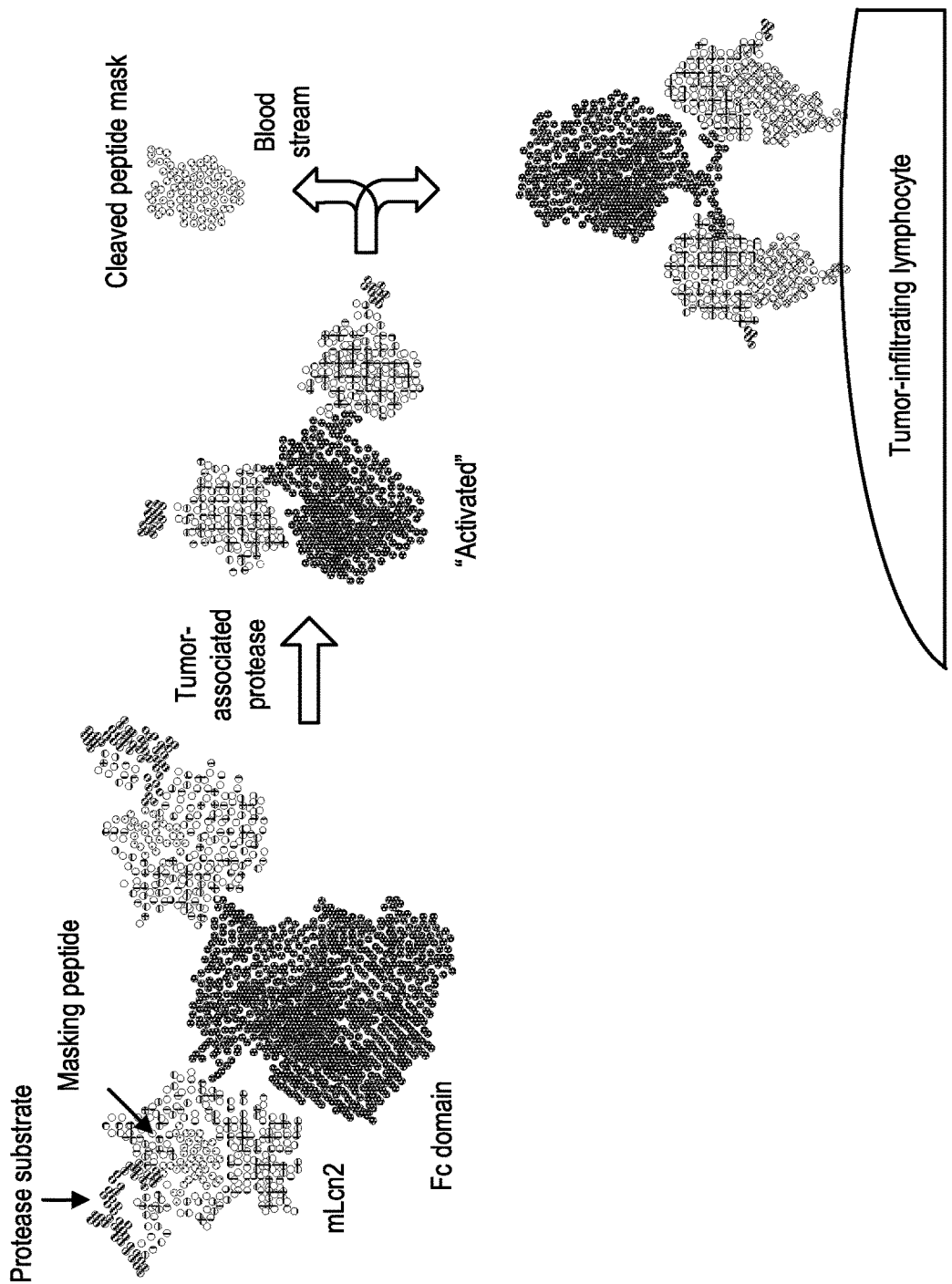
FIG. 1: Design and mode of action of a reversibly masked CTLA-4 antagonist mLcn2 (also referred to herein as CTLA-4 binding protein). In normal tissues the CTLA-4 antagonist remains masked and does not bind to CTLA-4 expressing target cells. In the tumor environment, tumor-associated MMP9 cleaves the linker (cleavable peptide linker) between masking peptide (CTLA-4 binding domain masking peptide) and mLcn2 (CTLA-4 binding domain) followed by dissociation of the mask (CTLA-4 binding domain masking peptide) and CTLA-4 blockade at the tumor site.

CBDMP-CPL-CBD-D cleavable peptide linker as provided herein (e.g., an MMP9 or μPA cleavage site), and CBDMP is a CTLA-4 binding domain masking peptide as provided herein (e.g., a peptide of SEQ ID NO:9 or 12). In embodiments, the C-terminus of CBDMP is connected to the N-terminus of CPL, the C-terminus of CPL is connected to the N-terminus of CBD and the C-terminus of CBD is connected to the N-terminus of DD. In other embodiments, the C-terminus of CBD is connected to the N-terminus of CPL, the C-terminus of CPL is connected to the N-terminus of CBDMP and the C-terminus of CBDMP is connected to the N-terminus of DD. FIGS. 1, 3 and 7 set forth exemplary recombinant CTLA-4 binding proteins having exemplary dimerizing domains, CTLA-4 binding domains, cleavable peptide linkers and CTLA-4 binding domain masking peptides. In embodiments, the recombinant CTLA-4 binding protein of formula (II) is covalently attached to a targeting domain. In further, embodiments the dimerizing domain connects the CTLA-4 binding domain with the targeting domain.

In embodiments, the CBD is not an ScFv.

In embodiments, more than one recombinant CTLA-4 binding protein is covalently attached to a dimerizing domain. Where more than one recombinant CTLA-4 binding protein is covalently attached to a dimerizing domain, the CTLA-4 binding protein may have the formula:

CBDMP-CPL-CBD-DD-CBD-CPL-CBDMP (III).

In Formula (III), DD is a dimerizing domain as provided herein (e.g., IgG$_1$ Fc), CBD is a CTLA-4 binding domain as provided herein (e.g., CTLA-4 binding LCN2), CPL is a cleavable peptide linker as provided herein (e.g., an MMP9 or μPA cleavage site), and CBDMP is a CTLA-4 binding domain masking peptide as provided herein (e.g., a peptide of SEQ ID NO:9 or 12). FIGS. 1 and 7 set forth exemplary recombinant CTLA-4 binding proteins having exemplary dimerizing domains, CTLA-4 binding domains, cleavable peptide linkers and CTLA-4 binding domain masking peptides. In embodiments, the recombinant CTLA-4 binding protein of formula (III) is covalently attached to a targeting domain. In further, embodiments the dimerizing domain connects the CTLA-4 binding domain with the targeting domain.

The recombinant CTLA-4 binding proteins provided herein may form part of a bispecific antibody. A bispecific antibody refers to an antibody that is capable of binding to two different types of antigen (e.g. is composed of fragments of two different monoclonal antibodies). Bispecific antibodies may simultaneously bind to a cytotoxic cell (using a receptor like CD3) and a target cell (e.g., tumour cell). Non-limiting examples of bispecific antibodies are disclosed in WO 93/08829, Traunecker et al., EMBO J. 10:3655-3659 (1991); and Suresh et al., Methods in Enzymology 121:210 (1986)).

CTLA-4 Binding Protein Dimer

In another aspect, there is provided a recombinant CTLA-4 binding protein dimer including two identical binding protein domains, each of the binding protein domains including (i) a CTLA-4 binding domain; (ii) a CTLA-4 binding domain masking peptide; (iii) a cleavable peptide linker connecting the CTLA-4 binding domain masking peptide to the CTLA-4 binding domain; and (iv) a dimerizing domain covalently attached to the CTLA-4 binding domain, wherein the binding protein domains are bound together. In embodiments, each of the recombinant CTLA-4 binding proteins is covalently attached to a targeting domain. In further, embodiments the dimerizing domain connects the CTLA-4 binding domain with the targeting domain. In embodiments, the dimerizing domains of the binding protein domains are chemically different. In embodiments, the dimerizing domains of the binding protein domains are identical.

The CTLA-4 binding domain, CTLA-4 binding domain masking peptide, cleavable peptide linker and the dimerizing domain included in the CTLA-4 binding protein dimer, may be any of the CTLA-4 binding domains (e.g., CTLA-4 binding LCN2), CTLA-4 binding domain masking peptides (e.g., a peptide of SEQ ID NO:9 or 12), cleavable peptide linkers (e.g., an MMP9 or μPA cleavage site), and dimerizing domains (e.g., IgG$_1$ Fc) described in the section above including embodiments thereof. Thus, in embodiments, the CTLA-4 binding domain is a CTLA-4 binding lipocalin 2 (LCN2).

In embodiments, the CTLA-4 binding domain masking peptide includes a sequence having about 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the CTLA-4 binding domain masking peptide includes a sequence having about 90% homology to SEQ ID NO:1. In embodiments, the CTLA-4 binding domain masking peptide includes a sequence having about 90% homology to SEQ ID NO:2. In embodiments, the CTLA-4 binding domain masking peptide includes a sequence having about 90% homology to SEQ ID NO:3. In embodiments, the CTLA-4 binding domain masking peptide includes a sequence having about 90% homology to SEQ ID NO:4. In embodiments, the CTLA-4 binding domain masking peptide includes a sequence having about 90% homology to SEQ ID NO:5. In embodiments, the CTLA-4 binding domain masking peptide includes a sequence having about 90% homology to SEQ ID NO:6. In embodiments, the CTLA-4 binding domain masking peptide includes a sequence having about 90% homology to SEQ ID NO:7. In embodiments, the CTLA-4 binding domain masking peptide includes a sequence having about 90% homology to SEQ ID NO:8. In embodiments, the CTLA-4 binding domain masking peptide includes a sequence having about 90% homology to SEQ ID NO:9. In embodiments, the CTLA-4 binding domain masking peptide includes a sequence having about 90% homology to SEQ ID NO:10. In embodiments, the CTLA-4 binding domain masking peptide includes a sequence having about 90% homology to SEQ ID NO:11. In embodiments, the CTLA-4 binding domain masking peptide includes a sequence having about 90% homology to SEQ ID NO:12. In embodiments, the CTLA-4 binding domain masking peptide includes a sequence having about 90% homology to SEQ ID NO:13. In embodiments, the CTLA-4 binding domain masking peptide includes a sequence having about 90% homology to SEQ ID NO:14.

In embodiments, the recombinant CTLA-4 binding protein dimer has at least 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the recombinant CTLA-4 binding protein dimer has at least 90% homology to SEQ ID NO:1. In embodiments, the recombinant CTLA-4 binding protein dimer has at least 90% homology to SEQ ID NO:2. In embodiments, the recombinant CTLA-4 binding protein dimer has at least 90% homology to SEQ ID NO:3. In embodiments, the recombinant CTLA-4 binding protein dimer has at least 90% homology to SEQ ID NO:4. In embodiments, the recombinant CTLA-4 binding protein dimer has at least 90% homology to SEQ ID NO:5. In embodiments, the recombinant CTLA-4 binding protein dimer has at least 90% homology to SEQ ID NO:6. In embodiments, the recombinant CTLA-4 binding protein dimer has at least 90% homology to SEQ ID NO:7. In embodiments, the recombinant CTLA-4 binding protein dimer has at least 90% homology to SEQ ID NO:8. In embodiments, the recombinant CTLA-4 binding protein dimer has at least 90% homology to SEQ ID NO:9. In embodiments, the recombinant CTLA-4 binding protein dimer has at least 90% homology to SEQ ID NO:10. In embodiments, the recombinant CTLA-4 binding protein dimer has at least 90% homology to SEQ ID NO:11. In embodiments, the recombinant CTLA-4 binding protein dimer has at least 90% homology to SEQ ID NO:12. In embodiments, the recombinant CTLA-4 binding protein dimer has at least 90% homology to SEQ ID NO:13. In embodiments, the recombinant CTLA-4 binding protein dimer has at least 90% homology to SEQ ID NO:14.

Further to the recombinant CTLA-4 binding protein dimer, in embodiments the CTLA-4 binding domain masking peptide includes a glycoprotein secretion signal. In embodiments, the glycoprotein secretion signal is a glycoprotein (gp) 67 secretion signal.

Yet further to the recombinant CTLA-4 binding protein dimer, in embodiments the cleavable peptide linker connects the CTLA-4 binding domain masking peptide to the N-terminus of the CTLA-4 binding domain. In embodiments, the cleavable peptide linker connects the CTLA-4 binding domain masking peptide to the C-terminus of the CTLA-4 binding domain. In embodiments, the cleavable peptide linker includes a protease cleavage site. In embodiments, the protease cleavage site is a tumor-associated protease cleavage site. In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP9 cleavage site, a MMP13 cleavage site, a MMP2 cleavage site, or a µPA cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site.

Yet further to the recombinant CTLA-4 binding protein dimer, in embodiments the CTLA-4 binding domain is covalently attached to a dimerizing domain. In embodiments, the dimerizing domain is a Fc protein domain. In embodiments, the Fc protein domain is an IgG$_1$ Fc protein.

Recombinant Nucleic Acids

In another aspect, there is provided a recombinant nucleic acid encoding the recombinant CTLA-4 binding protein as disclosed herein. In embodiments, the recombinant nucleic acid forms part of a viral vector. Examples of viral vectors include, but are not limited to retroviral, adenoviral, lentiviral and adeno-associated viral vectors. In some embodiments, the nucleic acid molecules are introduced into a cell using a retroviral vector following standard procedures well known in the art.

Recombinant Peptides

The recombinant peptides provided herein are, inter alia, capable of binding to, or otherwise exhibiting an affinity for, a CTLA-4 binding domain as provided herein including embodiments thereof. When non-covalently bound to a CTLA-4 binding domain provided herein, the recombinant peptide inhibits or otherwise prevents the activity or binding of the recombinant CTLA-4 binding domain to its cognate receptor or protein.

In another aspect, there is provided a peptide including a sequence having about 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the peptide includes a sequence having about 90% homology to SEQ ID NO:1. In embodiments, the peptide includes a sequence having about 90% homology to SEQ ID NO:2. In embodiments, the peptide includes a sequence having about 90% homology to SEQ ID NO:3. In embodiments, the peptide includes a sequence having about 90% homology to SEQ ID NO:4. In embodiments, the peptide includes a sequence having about 90% homology to SEQ ID NO:5. In embodiments, the peptide includes a sequence having about 90% homology to SEQ ID NO:6. In embodiments, the peptide includes a sequence having about 90% homology to SEQ ID NO:7. In embodiments, the peptide includes a sequence having about 90% homology to SEQ ID NO:8. In embodiments, the peptide includes a sequence having about 90% homology to SEQ ID NO:9. In embodiments, the peptide includes a sequence having about 90% homology to SEQ ID NO:10. In embodiments, the peptide includes a sequence having about 90% homology to SEQ ID NO:11. In embodiments, the peptide includes a sequence having about 90% homology to SEQ ID NO:12. In embodiments, the peptide includes a sequence having about 90% homology to SEQ ID NO:13. In embodiments, the peptide includes a sequence having about 90% homology to SEQ ID NO:14.

In embodiments, the sequence has at least 90% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14. In embodiments, the sequence has at least 90% homology to SEQ ID NO:1. In embodiments, the sequence has at least 90% homology to SEQ ID NO:2. In embodiments, the sequence has at least 90% homology to SEQ ID NO:3. In embodiments, the sequence has at least 90% homology to SEQ ID NO:4. In embodiments, the sequence has at least 90% homology to SEQ ID NO:5. In embodiments, the sequence has at least 90% homology to SEQ ID NO:6. In embodiments, the sequence has at least 90% homology to SEQ ID NO:7. In embodiments, the sequence has at least 90% homology to SEQ ID NO:8. In embodiments, the sequence has at least 90% homology to SEQ ID NO:9. In embodiments, the sequence has at least 90% homology to SEQ ID NO:10. In embodiments, the sequence has at least 90% homology to SEQ ID NO:11. In embodiments, the sequence has at least 90% homology to SEQ ID NO:12. In embodiments, the sequence has at least 90% homology to SEQ ID NO:13. In embodiments, the sequence has at least 90% homology to SEQ ID NO:14.

In embodiments, the sequence is SEQ ID NO:1, In embodiments, the sequence is SEQ ID NO:2, In embodiments, the sequence is SEQ ID NO:3, In embodiments, the sequence is SEQ ID NO:4, In embodiments, the sequence is SEQ ID NO:5, In embodiments, the sequence is SEQ ID NO:6, In embodiments, the sequence is SEQ ID NO:7, In embodiments, the sequence is SEQ ID NO:8, In embodiments, the sequence is SEQ ID NO:9, In embodiments, the sequence is SEQ ID NO:10, In embodiments, the sequence is SEQ ID NO:11, In embodiments, the sequence is SEQ ID NO:12, In embodiments, the sequence is SEQ ID NO:13, In embodiments, the sequence is SEQ ID NO:14.

In embodiments, the sequence has about 70%, 75%, 80%, 85%, 90%, 91%, 92%, 93%, 94%, 95%, 96%, 97%, 98%, 99% or 100% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

In embodiments, the peptide further includes a glycoprotein secretion signal. In embodiments, the glycoprotein secretion signal is a glycoprotein (gp) 67 secretion signal.

Pharmaceutical Compositions

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the recombinant CTLA-4 binding protein provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred In another aspect, there is provided a pharmaceutical composition including a pharmaceutically acceptable excipient and a recombinant CTLA-4 binding protein as disclosed herein or a recombinant CTLA-4 binding protein dimer as disclosed herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Treatment

In another aspect, there is provided a method of treating a CTLA-4-mediated disease in a subject in need thereof. The method includes administering to a subject a therapeutically effective amount of a recombinant CTLA-4 binding protein as disclosed herein, or a therapeutically effective amount of a recombinant CTLA-4 binding protein dimer as disclosed herein.

In embodiments, the CTLA-4-mediated disease is cancer. In embodiments, the CTLA-mediated disease is a cancer as set forth herein. In embodiments, the cancer is leukemia, lymphoma, head and neck cancer, colorectal cancer, prostate cancer, pancreatic cancer, melanoma, breast cancer, neuroblastoma, lung cancer, ovarian cancer, osteosarcoma, bladder cancer, cervical cancer, liver cancer, kidney cancer, skin cancer or testicular cancer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Where combination treatments are contemplated, it is not intended that the agents (i.e. ribonucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The compositions (e.g., recombinant CTLA-4 binding proteins) described herein can be used in combination with one another, with other active agents known to be useful in treating a cancer such as anti-cancer agents.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechlorethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin;

aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetyl acetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Iso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In embodiments, the active and/or adjunctive agents may be linked or conjugated to one another.

EXAMPLES

The results and reagents generated in this application are expected to significantly and in short order impact immunotherapeutic approaches to advanced stage cancer. This is particularly relevant to patient populations currently not considered for high-risk immunotherapies due to adverse effects. Specifically, Applicants envision that safer CTLA-4 blockers may be used in patients with locally advanced disease at risk for metastatic spread.

In embodiments, the modified lipocalin2 (mLcn2) used as a CTLA-4 antagonist (CTLA-4 binding protein) herein (FIG. 1) binds to murine, primate and human CTLA-4. This circumstance provides versatility in testing of alternative designs across different animal models including higher mammals. Applicants used human IgG sequences to dimerize mLcn2 simplifying detection of this reagent in situ for crucial biodistribution studies as presented here. Applicants have exploited this circumstance to demonstrate efficient masking of mLcn2-Fc. Beyond CTLA-4 antagonists (CTLA-4 binding proteins) the masking technology can be used to engage multiple other targets of therapeutic interest currently intractable due to forbidding off-target effects.

Background:

Engaging immune checkpoint modulators at tumor sites but not in normal tissues represents an alternative and safer approach to elicit effective anti-tumor immune responses. Specifically, in murine models local administration of a combination of CTLA-4- and OX40-targeted antibodies together with a TLR9 agonist (unmethylated CpG nucleotides) not only eliminated tumors at the injection sites but also disseminated disease at a distance. Systemic administration of in vivo activated CTLA-4 antagonists as presented here potentially improves this concept further as masked CTLA-4 antagonists are expected to be activated at any and all tumor sites including occult metastases.

Characterization and Refinement of a 'Masked' Recombinant CTLA-4 Antagonists Preferentially Active at Tumor Sites.

Rationale and Significance:

One goal is to exploit high levels of extracellular proteases in the tumor microenvironment (Jamaspishvili, T., et al., 2010. Urine markers in monitoring for prostate cancer. *Prostate cancer and prostatic diseases* 13:12-19; Hadler-Olsen, E., et al, 2013. Matrix metalloproteinases in cancer: their value as diagnostic and prognostic markers and therapeutic targets. *Tumour Biol* 34:2041-2051) to specifically and effectively activate a CTLA-4-targeted prodrug, leading to selective activation of T cells in the tumor environment. To this end, Applicants have taken two unique approaches to mask a recombinant CTLA-4 blocker (mLcn2): 1) a non-covalent mask (as described in Applicants' previous application) and 2) a covalent mask tethered N-terminal to mLcn2.

Data:

The sequence of mLcn2 was obtained from the PDB, synthesized and produced in bacteria. Peptides that specifically bind to mLcn2 were identified using a cyclic 7-mer library. Positive leads were identified and sequencing of these hits indicated an overall pattern in the sequences. To further characterize the lead peptides and to ensure the peptides bound to the same site as CTLA, a competition ELISA was performed using all leads (FIG. 2A). Based on this analysis, two cyclic peptides were chosen, chemically synthesized, and characterized by SPR (FIG. 2B) and crystallography. Well diffracting crystals were obtained for both complexes (1.95 and 2.15 Å) and refined ($R/R_{free}$ of 18.0/22.5% and 16.5/18.5% and no Ramachandran outliers). Superposition of the structures indicated that the peptides indeed bind to the same position as CTLA-4, but each in slightly different manner. Design of the linker was aided by examination of the crystal structure of lipocalin.

Based on these data, Applicants chose peptide 16, fused it to the N-terminus of mLcn2 and fused this to the N-terminus of an IgG1 Fc domain through a flexible linker (FIG. 1 and FIG. 3A). Adding the Fc to the C-terminus created a bivalent, high-affinity CTLA-4 antagonist that offers several advantages in certain contexts. For example, many biologics achieve high affinity and specificity through multivalency. Additionally, the non-covalent mask that could be released by reducing the valency of the mask. And, the Fc increases the mass above the renal threshold. As an added benefit, the Fc facilitates purification efforts. The construct was produced at high yield (>50 mg/L) and readily purified from the media. As a control, two additional constructs were generated—one without a mask fused to the N-terminus (positive control—naked mLcn2) and one in which the MMP9 cleavage site was mutated (negative control). In the following Applicants will interchangeably use mLcn2 and mLcn2-Fc.

The masked mLcn2 was characterized in vitro by size exclusion chromatography and SPR analysis (FIG. 3 C/D). Admixtures of the masked mLcn2 and a recombinant bivalent CTLA-4 (also fused to the human IgG1 Fc) were incubated and applied to an analytical column. In the absence of MMP9, the combination eluted at the same position as the individual components. However, incubation with MMP9 led to an earlier elution, indicating the formation of a heterodimeric complex. No shift was observed with MMP9-mutated masked mLcn2 control and CTLA-4-Fc (FIG. 3B). Similar results were obtained using SPR (FIG. 3C). In these studies, monomeric CTLA-4 was chemically tethered to the chip and the masked mLcn2, MMP-cleaved masked mLcn2 and the n-mLcn2 (no N-terminal fusion) was passed over the chip. These data indicate peptide 16 fused to the mLcn2 effectively occludes CTLA-4, despite a significant difference in affinity (e.g. fusing the peptide to mLcn2 effectively creates an "infinite" concentration of the peptide at the binding site).

In vivo testing of the masked and MMP9-treated, unmasked mLcn2 revealed preferential localization of all mLcn2 variants except the masked uncleavable construct in tumor masses as determined by IHC (FIG. 4). In these experiments constructs were injected i.v. into C57/B16 mice bearing B16 melanomas. Three days after injection, tumor and tissue samples were collected and doublestained using antibodies recognizing either CD4 or CD8 and mLcn2 (e.g. human IgG-Fc). Membranes of both intratumoral CD4+ and CD8+ T cells were decorated with mLcn2 which was not detected on other cell types. Importantly, weak or no reactivity was observed in tumor tissues using the noncleavable masked mLcn2. In addition, consistent with the previous report using CTLA-4 antibodies (Iwama, S., et al., 2014. Pituitary expression of CTLA-4 mediates hypophysitis secondary to administration of CTLA-4 blocking antibody. *Sci Transl Med* 6:230ra245), Applicants observed mLcn2 reactivity with non-immune cells in the pituitary glands (FIG. 5). Finally, masked and unmasked mLcn2 constructs bound to CD4/CD8 negative cells in the spleen (not shown) potentially due to FcR binding (see discussion on further design improvements below).

One version of the masked CTLA-4 prodrug contained a 'minimal' linker between the masking peptide and the mLcn2. Using the crystal structure, the Schroedinger package was used to model the linker 'conformation'. While the linker may be flexible and accessible (e.g., can be specifically cleaved with recombinant MMP9), this modeling exercise indicates that there may be steric hindrance, which could reduce access to the protease and efficient cleavage of the mask in tissues. Alternative linkers shown in FIG. 6 are anticipated to make the protease site more solvent accessible. Size exclusion chromatography and SPR can be used to evaluate masking efficiencies (see FIG. 3). The efficiency of cleavage by MMP9 for each construct can be quantified by mass spectrometry. Each masked construct is exposed with MMP9 and mass spectrometry is used to identify the cleavage products. Ensuring the predicted cleaved peptide mask is generated, a synthetic peptide product, incorporating $^{15}N$ into the peptide, will be produced. Next, different concentrations of unlabeled construct will be treated individually with MMP9 and the reaction quenched with trifluoroacetic acid at specific time points. The quenched samples will be spiked with a known concentration of the 15N labeled peptide and matrix-assisted laser desorption/ionization-time-of-flight (MALDI-TOF) mass spectrometry to determine the amount of cleaved product liberated (Gao, W., et al., 2006. Exosite interactions contribute to tension-induced cleavage of von Willebrand factor by the antithrombotic ADAMTS13 metalloprotease. *Proc Natl Acad Sci USA* 103:19099-19104; Guitot, K., et al., 2014. Label-free measurement of histone lysine methyltransferases activity by matrix-assisted laser desorption/ionization time-of-flight mass spectrometry. *Anal Biochem* 456:25-31). The rates will be determined by performing measurements different time intervals. Determining these rates for each construct will provide crucial information vis-à-vis steric constraints of the biologic and masking agent. Moreover, combining these data with in vivo biodistribution data (see FIGS. 4 and 5 and section C.5.4) will afford valuable and general insights into generating prodrugs.

TABLE 1

| Tumor associated protease | Substrate Sequence | Ref. |
|---|---|---|
| PSA | HSSKLQ (SEQ ID NO: 28) | Singh, P., et al., 2009. Molecular insights into substrate specificity of prostate specific antigen through structural modeling. Proteins 77: 984-99) |
| PSMA | DEEEE (SEQ ID NO: 29) | Denmeade, S. R., et al. 2012. Engineering a prostate-specific membrane antigen-activated tumor endothelial cell prodrug for cancer therapy. Science translational medicine 4: 140ra 18) |
| Legumain | AAN (SEQ ID NO: 30) | Liu, Z., et al. 2014. Legumain protease-activated TAT-liposome cargo for targeting tumours and their microenvironment. Nat Commun 5: 4280 |
| μPA | SGRSA (SEQ ID NO: 31) | (Ke, S. H., et al., 1997. Optimal subsite occupancy and design of a selective inhibitor of urokinase. J Blot Chem 272: 20456-20462 |
| Cathepsin B | GFLG (SEQ ID NO: 32) | Biniossek, M. L., et al., 2011. Proteomic identification of protease cleavage sites characterizes prime and non-prime specificity of cysteine cathepsins B, L, and S. J Proteome Res 10: 5363-5373 |
| Fibroblast associated protein | ASGPAGPA (SEQ ID NO: 33) | Brennen, W. N., et al., S.R. 2012. Targeting carcinoma-associated fibroblasts within the tumor stroma with a fibroblast activation protein-activated prodrug. J Natl Cancer Inst 104: 1320-1334; Brennen, W. N., et al., 2012. Rationale behind targeting fibroblast activation protein-expressing carcinoma-associated fibroblasts as a novel chemotherapeutic strategy. Mol Cancer Ther 11: 257-266) |

While MMP9 was initially selected based on its prevalence in multiple tumor forms and, specifically, the tumor models under investigation here, there are multiple proteases overexpressed in the tumor stroma and one or more may better differentiate between tumor and off-target activation of the prodrug. This includes the sequence for prostate specific antigen (PSA), prostate specific membrane antigen (PSMA), legumain, μPA, cathepsin B, and fibroblast activation protein (Table 1). Each protease is commercially available. Information gained above can be used to position the substrate within the linker. As the substrates are of different lengths, Applicants will either repeat the substrate (e.g., AANAANAAN [SEQ ID NO:62] for legumain) and or add glycines to maintain a linker length comparable for each construct. Moreover, two protease sites in the linker may be more effective than a single protease site. For instance, a PSA-PSMA linker, HSSKLQDEEEE (SEQ ID NO:63), could be used for prostate cancer. As above, each can be characterized by size exclusion chromatography and SPR to ensure each is appropriately masked. Moreover, cleavage activity of each for each protease can be quantified by using mass spectrometry, also as described above. Moreover, the activity each masked construct against each protease will provide information about the cross reactivity.

In an attempt to improve the affinity of the mask a higher affinity peptide may be used. Alternatively, the interaction may be 'maturated' in a targeted fashion. This may be achieved by adding two residues to the N-terminus of the masking peptide encoding each amino acid and selecting for higher affinity. Likewise, all twenty residues at the C-terminus of the peptide can be encoded and selected for a higher affinity peptide.

Informal Sequence Listing

TABLE 2

Identification of CTLA-4 binding domain masking peptide. See FIG. 2.

| Peptide No. | Sequence | SEQ ID NO: |
|---|---|---|
| 6 | CEKWFRFMC | 5 |
| 9 | CVTGFEFLC | 7 |
| 12 | CSVLPPFMC | 9 |
| 19 | CSVLLPFMC | 13 |
| 16 | CWSPLPFMC | 12 |
| 11 | CPRPLYWLC | 8 |
| 3 | CFTPWPEAC | 3 |
| 20 | CFHAPWAPC | 14 |
| 13 | CNNYKGGRC | 10 |
| 4 | CWPEWDLWC | 4 |
| 15 | CLPEISFLC | 11 |
| 2 | CRIDERLQC | 2 |
| 8 | CYLELMHSC | 6 |
| 1 | CYGLGFNFC | 1 |

Pep##-protease_site-mLCN2-Fc (SEQ ID NO: 15)

atgctactagtaaatcagtcacaccaaggcttcaataaggaacacacaagcaagatggta agcgctattgttttatatgtgcttttggcggcggcggcgcattctgcctttgcggcggga tcctgttacggattaggtttcaacttctgtggcggtagtgtcccgctgtcgctgtatagt ggatcccaggactctaccagcgacctgatccccgcaccaccgctgtctaaggtgccactg cagcaaaacttccaggacaatcaatttcacggtaaatggtacgtggtcggcctggctgga aaccgtatcctgcgcgacgatcagcatcctatgaatatgtacgcgactatttatgaactg aaggaagacaaaagctacaacgttacctccgtgatctcttcacacaagaaatgcgaatat acgattgccaccttcgtgccgggaagccagcctggcgagtttaccctgggcaatatcaag tcttacggagacaaaacctcatatctggtgcgcgttgtgtccactgattacaaccaatat gcagtcgttttctttaagctggcggaagataatgcagagttctttgccatcaccatttat ggccgtactaaggagctggccagcgaactgaaagagaacttcattcgctttagtaaatcg ctgggcctgccagagaatcacattgttttccctgtccccattgaccagtgtattgacggc tctagatcaggtggcacctcaggtggcggtagtgtcccggggtcggggtctagtggttcg accagcggctccggtaaaagctccgagggcagcggccaagcttcgacccatacctgccca ccatgtccagctcctgaactgctgggtggtccaagcgtgttcctgtttccgcctaagcct aaagacaccctgatgatcagccgtaccccagaggtcacctgcgtggtcgttgacgtttcc cacgaagatccagaggtcaagttcaactggtacgtggatggcgttgaagtgcataatgct aagaccaaaccccgtgaagagcagtacaactctacctatcgcgtggtctcagtcctgacc gttctgcaccaggactggctgaacggcaaagagtataagtgcaaagtctctaataaggcg ctgcccgcaccaatcgaaaaaaccatttcaaaggcgaagggtcagccccgtgagccacag gtttacaccctgcccccaagtcgcgacgaactgaccaagaaccaggtgtcgctgacctgt ctggtcaaaggcttctatccgtctgatattgcagtggaatgggagtcaaatggtcagcct gagaacaattacaagaccaccccgcctgttctggactccgatggctctttctttctgtat agcaagctgaccgtggataaatcccgctggcagcagggtaacgtgttcagctgctcagtg atgcatgaagccctgcacaatcattacacccagaagagtctgtcgctgagcccgggtaaa taa Pep##-protease_site-mLCN2-Fc (SEQ ID NO: 16)

MLLVNQSHQGFNKEHTSKMV
SAIVLYVLLAAAAHSAFAAG
SCYGLGFNFCGGSVPLSLYS
GSQDSTSDLIPAPPLSKVPL
QQNFQDNQFHGKWYVVGLAG
NRILRDDQHPMNMYATIYEL
KEDKSYNVTSVISSHKKCEY
TIATFVPGSQPGEFTLGNIK
SYGDKTSYLVRVVSTDYNQY
AVVFFKLAEDNAEFFAITIY
GRTKELASELKENFIRFSKS
LGLPENHIVFPVPIDQCIDG
SRSGGTSGGGSVPGSGSSGS
TSGSGKSSEGSGQASTHTCP
PCPAPELLGGPSVFLFPPKP
KDTLMISRTPEVTCVVVDVS
HEDPEVKFNWYVDGVEVHNA
KTKPREEQYNSTYRVVSVLT
VLHQDWLNGKEYKCKVSNKA
LPAPIEKTISKAKGQPREPQ
VYTLPPSRDELTKNQVSLTC
LVKGFYPSDIAVEWESNGQP
ENNYKTTPPVLDSDGSFFLY
SKLTVDKSRWQQGNVFSCSV
MHEALHNHYTQKSLSLSPGK

Pep01-MMP9-mLCN2-IgG1

(SEQ ID NO: 17)

AGSCYGLGFN FCGGSVPLSL YSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep02-MMP9-mLCN2-IgG1

(SEQ ID NO: 18)

AGSCRIDETL QCGGSVPLSL YSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

```
CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep04-MMP9-mLCN2-IgG1                                           (SEQ ID NO: 19)
AGSCWPEWDL WCGGSVPLSL YSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep12-MMP9-mLCN2-IgG1                                           (SEQ ID NO: 20)
AGSCSVLPPF MCGGSVPLSL YSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-MMP9-mLCN2-IgG1                                           (SEQ ID NO: 21)
AGSCWSPLPF MCGGSVPLSL YSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-Mxx9-mLCN2-IgG1 (inactive MMP9 cleavage site)
                                                                (SEQ ID NO: 22)
AGSCWSPLPF MCGGSVPGSG SSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK
```

-continued

Pep16-uPA-mLCN2-IgG1 (cleavage site for uPA, MT-SP1, and legumain)
(SEQ ID NO: 23)
AGSCWSPLPF MCGSLSGRS DNHGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-PSA-mLCN2-IgG1 (cleavage site for PSA)
(SEQ ID NO: 24)
AGSCWSPLPF MCGGSHSSKL QLGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-ADAM17-mLCN2-IgG1 (cleavage site for ADAM9, ADAM10, ADAM17)
(SEQ ID NO: 25)
AGSCWSPLPF MCGSPLAQAV RSGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-MMP13-mLCN2-IgG1 (cleavage site for MMP13)
(SEQ ID NO: 26)
AGSCWSPLPF MCGGSGPLGM RGGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK

Pep16-MMP2-mLCN2-IgG1 (cleavage site for M1P2)
(SEQ ID NO: 27)
AGSCWSPLPF MCGGSNLAYY TAGSQDSTSD LIPAPPLSKV PLQQNFQDNQ FHGKWYVVGL

AGNRILRDDQ HPMNMYATIY ELKEDKSYNV TSVISSHKKC EYTIATFVPG SQPGEFTLGN

IKSYGDKTSY LVRVVSTDYN QYAVVFFKLA EDNAEFFAIT IYGRTKELAS ELKENFIRFS

```
KSLGLPENHI VFPVPIDQCI DGSRSGGTSG GGSVPGSGSS GSTSGSGKSS EGSGQASTHT

CPPCPAPELL GGPSVFLFPP KPKDTLMISR TPEVTCVVVD VSHEDPEVKF NWYVDGVEVH

NAKTKPREEQ YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP PVLDSDGSFF

LYSKLTVDKS RWQQGNVFSC SVMHEALHNH YTQKSLSLSP GK
```

(SEQ ID NO: 28)
HSSKLQ.

(SEQ ID NO: 29)
DEEEE.

(SEQ ID NO: 30)
AAN.

(SEQ ID NO: 31)
SGRSA.

(SEQ ID NO: 32)
GFLG.

(SEQ ID NO: 33)
ASGPAGPA mLCN2

(SEQ ID NO: 34)
```
Q D S T S D L I P A P P L S K V P L

Q Q N F Q D N F H G K W Y V V G L A G

N R I L R D D Q H P M N M Y A T I Y E L

K E D K S Y N V T S V I S S H K K C E Y

T I A T F V P G S Q P G E F T L G N I K

S Y G D K T S Y L V R V V S T D Y N Q Y

A V V F F K L A E D N A E F F A I T I Y

G R T K E L A S E L K E N F I R F S K S

L G L P E N H I V F P V P I D Q C I D G
``` gp67 secretion signal (SEQ ID NO: 35)
```
M L L V N Q S H Q G F N K E H T S K M V

S A I V L Y V L L A A A A H S A F
```

A1R-Pep16-MMP9-mLCN2-Fc (SEQ ID NO: 36)
```
atgctactagtaaatcagtcacaccaaggcttcaataaggaacacacaagcaagatggtaagcgctattgtttta tatgtgcttttggcggcggcggcgcattctgcctttgcgCGgggATCCTGttGGagTCcaTTACCcTTcATGTgt ggcggtagtgtcccgctgtcgctgtatagtggatcccaggactctaccagcgacctgatccccgcaccaccgctg tctaaggtgccactgcagcaaaacttccaggacaatcaatttcacggtaaatggtacgtggtcggcctggctgga aaccgtatcctgcgcgacgatcagcatcctatgaatatgtacgcgactatttatgaactgaaggaagacaaaagc tacaacgttacctccgtgatctcttcacacaagaaatgcgaatatacgattgccaccttcgtgccgggaagccag cctggcgagtttaccctgggcaatatcaagtcttacggagacaaaacctcatatctggtgcgcgttgtgtccact gattacaaccaatatgcagtcgttttctttaagctggcggaagataatgcagagttcttttgccatcaccatttat ggccgtactaaggagctggccagcgaactgaaagagaacttcattcgctttagtaaatcgctgggcctgccagag aatcacattgttttccctgtccccattgaccagtgtattgacggctctagatcaggtggcacctcaggtggcggt agtgtcccggggtcggggtctagtggttcgaccagcggctccggtaaaagctccgagggcagcggccaagcttcg acccatacctgcccaccatgtccagctcctgaactgctgggtggtccaagcgtgttcctgtttccgcctaagcct aaagacacccctgatgatcagccgtaccccagaggtcacctgcgtggtcgttgacgtttcccacgaagatccagag
```

```
gtcaagttcaactggtacgtggatggcgttgaagtgcataatgctaagaccaaaccccgtgaagagcagtacaac tctacctatcgcgtggtctcagtcctgaccgttctgcaccaggactggctgaacggcaaagagtataagtgcaaa gtctctaataaggcgctgcccgcaccaatcgaaaaaaccatttcaaaggcgaagggtcagccccgtgagccacag gtttacaccctgcccccaagtcgcgacgaactgaccaagaaccaggtgtcgctgacctgtctggtcaaaggcttc tatccgtctgatattgcagtggaatgggagtcaaatggtcagcctgagaacaattacaagaccaccccgcctgtt ctggactccgatggctctttctttctgtatagcaagctgaccgtggataaatcccgctggcagcagggtaacgtg ttcagctgctcagtgatgcatgaagccctgcacaatcattacacccagaagagtctgtcgctgagcccgggtaaa taa.
```

A1R-Pep16-MMP9-mLCN2-Fc (SEQ ID NO: 37)

MLLVNQSHQGFNKEHTSKMVSAIVLYVLLAAAAHSAFARGSCWSPLPFMCGGSVPLSLYSGSQDSTSDLIPAPPL

SKVPLQQNFQDNQFHGKWYVVGLAGNRILRDDQHPMNMYATIYELKEDKSYNVTSVISSHKKCEYTIATFVPGSQ

PGEFTLGNIKSYGDKTSYLVRVVSTDYNQYAVVFFKLAEDNAEFFAITIYGRTKELASELKENFIRFSKSLGLPE

NHIVFPVPIDQCIDGSRSGGTSGGGSVPGSGSSGSTSGSGKSSEGSGQASTHTCPPCPAPELLGGPSVFLFPPKP

KDTLMISRTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Pep16-uPA-mLCN2-Fc (SEQ ID NO: 38)

```
atgctactagtaaatcagtcacaccaaggcttcaataaggaacacacaagcaagatggtaagcgctattgtttta tatgtgcttttggcggcggcggcgcattctgcctttgcggcgggATCCTGttGGagTCCaTTACCcTTcATGTgt ggcggtagtCtcTcTGGTAGgTCTGataAtCACtcccaggactctaccagcgacctgatccccgcaccaccgctg tctaaggtgccactgcagcaaaacttccaggacaatcaatttcacggtaaatggtacgtggtcggcctggctgga aaccgtatcctgcgcgacgatcagcatcctatgaatatgtacgcgactatttatgaactgaaggaagacaaaagc tacaacgttacctccgtgatctcttcacacaagaaatgcgaatatacgattgccaccttcgtgccgggaagccag cctggcgagtttaccctgggcaatatcaagtcttacggagacaaaacctcatatctggtgcgcgttgtgtccact gattacaaccaatatgcagtcgttttcttcaagctggcggaagataatgcagagttctttgccatcaccatttat ggccgtactaaggagctggccagcgaactgaaagagaacttcattcgctttagtaaatcgctgggcctgccagag aatcacattgttttccctgtccccattgaccagtgtattgacggctctagatcaggtggcacctcaggtggcggt agtgtccccggggtcggggtctagtggttcgaccagcggctccggtaaaagctccgagggcagcggccaagcttcg acccatacctgcccaccatgtccagctcctgaactgctggtggtccaagcgtgttcctgtttccgcctaagcct aaagacaccctgatgatcagccgtaccccagaggtcacctgcgtggtcgttgacgtttcccacgaagatccagag gtcaagttcaactggtacgtggatggcgttgaagtgcataatgctaagaccaaaccccgtgaagagcagtacaac tctacctatcgcgtggtctcagtcctgaccgttctgcaccaggactggctgaacggcaaagagtataagtgcaaa gtctctaataaggcgctgcccgcaccaatcgaaaaaaccatttcaaaggcgaagggtcagccccgtgagccacag gtttacaccctgcccccaagtcgcgacgaactgaccaagaaccaggtgtcgctgacctgtctggtcaaaggcttc tatccgtctgatattgcagtggaatgggagtcaaatggtcagcctgagaacaattacaagaccaccccgcctgtt ctggactccgatggctctttctttctgtatagcaagctgaccgtggataaatcccgctggcagcagggtaacgtg ttcagctgctcagtgatgcatgaagccctgcacaatcattacacccagaagagtctgtcgctgagcccgggtaaa taa.
```

-continued

Pep16-uPA-mLCN2-Fc (SEQ ID NO: 39)

MLLVNQSHQGFNKEHTSKMVSAIVLYVLLAAAAHSAFAAGSCWSPLPFMCGGSLSGRSDNHSQDSTSDLIPAPPL

SKVPLQQNFQDNQFHGKWYVVGLAGNRILRDDQHPMNMYATIYELKEDKSYNVTSVISSHKKCEYTIATFVPGSQ

PGEFTLGNIKSYGDKTSYLVRVVSTDYNQYAVVFFKLAEDNAEFFAITIYGRTKELASELKENFIRFSKSLGLPE

NHIVFPVPIDQCIDGSRSGGTSGGGSVPGSGSSGSTSGSGKSSEGSGQASTHTCPPCPAPELLGGPSVFLFPPKP

KDTLMISRTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Pep16-PSA-mLCN2-Fc (SEQ ID NO: 40)

atgctactagtaaatcagtcacaccaaggcttcaataaggaacacacaagcaagatggtaagcgctattgtttta tatgtgcttttggcggcggcggcgcattctgcctttgcggcgggATCCTGttGGagTCCaTTACCcTTcATGTgt ggcggtagtTCcAAgTACCAgctgtatagtggatcccaggactctaccagcgacctgatcccgcaccaccgctg tctaaggtgccactgcagcaaaacttccaggacaatcaatttcacggtaaatggtacgtggtcggcctggctgga aaccgtatcctgcgcgacgatcagcatcctatgaatatgtacgcgactatttatgaactgaaggaagacaaaagc tacaacgttacctccgtgatctcttcacacaagaaatgcaatatacgattgccaccttcgtgccgggaagccag cctggcgagtttaccctgggcaatatcaagtcttacggagacaaaacctcatatctggtgcgcgttgtgtccact gattacaaccaatatgcagtcgttttcttttaagctggcggaagataatgcagagttcttgccatcaccatttat ggccgtactaaggagctggccagcgaactgaaagagaacttcattcgctttagtaaatcgctgggcctgccagag aatcacattgttttccctgtccccattgaccagtgtattgacggctctagatcaggtggcacctcaggtggcggt agtgtcccggggtcggggtctagtggttcgaccagcggctccggtaaaagctccgagggcagcggccaagcttcg acccatacctgcccaccatgtccagctcctgaactgctgggtggtccaagcgtgttcctgtttccgcctaagcct aaagacaccctgatgatcagccgtaccccagaggtcacctgcgtggtcgttgacgtttccacgaagatccagag gtcaagttcaactggtacgtggatggcgttgaagtgcataatgctaagaccaaacccgtgaagagcagtacaac tctacctatcgcgtggtctcagtcctgaccgttctgcaccaggactggctgaacggcaaagagtataagtgcaaa gtctctaataaggcgctgcccgcaccaatcgaaaaaaccatttcaaaggcgaagggtcagccccgtgagccacag gtttacaccctgccccaagtcgcgacgaactgaccaagaaccaggtgtcgctgacctgtctggtcaaaggcttc tatccgtctgatattgcagtggaatgggagtcaaatggtcagcctgagaacaattacaagaccacccgcctgtt ctggactccgatggctcttctcttctgtatagcaagctgaccgtggataaatcccgctggcagcagggtaacgtg ttcagctgctcagtgatgcatgaagccctgcacaatcattacacccagaagagtctgtcgctgagcccgggtaaa taa.

Pep16-PSA-mLCN2-Fc (SEQ ID NO: 41)

MLLVNQSHQGFNKEHTSKMVSAIVLYVLLAAAAHSAFAAGSCWSPLPFMCGGSSKYQLYSGSQDSTSDLIPAPPL

SKVPLQQNFQDNQFHGKWYVVGLAGNRILRDDQHPMNMYATIYELKEDKSYNVTSVISSHKKCEYTIATFVPGSQ

PGEFTLGNIKSYGDKTSYLVRVVSTDYNQYAVVFFKLAEDNAEFFAITIYGRTKELASELKENFIRFSKSLGLPE

NHIVFPVPIDQCIDGSRSGGTSGGGSVPGSGSGSTSGSGKSSEGSGQASTHTCPPCPAPELLGGPSVFLFPPKP

KDTLMISRTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVESCSVMHEALHNHYTQKSLSLSPGK

Pep16-MMP9-NGAL-Fc (SEQ ID NO: 42)
atgctactagtaaatcagtcacaccaaggcttcaataaggaacacacaagcaagatggtaagcgctattgtttta
tatgtgcttttggcggcggcggcgcattctgcctttgcggcgggATCCTGttGGagTCCaTTACCcTTcATGTgt
ggcggtagtgtcccgctgtcgctgtatagtggatcccaggactctaccagcgacctgatcccgcaccaccgctg
tctaaggtgccactgcagcaaaacttccaggacaatcaatttcacggtaaatggtacgtggtcggcctggctgga
aaccgtatcctgcgcgacgatcagGatcctCAgaatatgtacgcgactatttatgaactgaaggaagacaaaagc
tacaacgttacctccgtgatctcttcacacaagaaatgcgaatatacgattgccaccttcgtgcgggaagccag
cctggcgagtttaccctgggcaatatcaagtcttacggagacaaaacctcatatctggtgcgcgttgtgtccact
gattacaaccaatatgcagtcgttttcttttaagAAggcgTCaCaGaatgcagagttctttgccatcaccatttat
ggccgtactaaggagctggccagcgaactgaaagagaacttcattcgctttagtaaatcgctgggcctgccagag
aatcacattgttttccctgtcccccattgaccagtgtattgacggctctagatcaggtggcacctcaggtggcggt
agtgtcccggggtcggggtctagtggttcgaccagcggctccggtaaaagctccgagggcagcggccaagcttcg
acccatacctgcccaccatgtccagctcctgaactgctgggtggtccaagcgtgttcctgtttccgcctaagcct
aaagacacccctgatgatcagccgtaccccagaggtcacctgcgtggtcgttgacgtttcccacgaagatccagag
gtcaagttcaactggtacgtggatggcgttgaagtgcataatgctaagaccaaacccgtgaagagcagtacaac
tctacctatcgcgtggtctcagtcctgaccgttctgcaccaggactggctgaacggcaaagagtataagtgcaaa
gtctctaataaggcgctgcccgcaccaatcgaaaaaaccatttcaaaggcgaagggtcagccccgtgagccacag
gtttacacccctgcccccaagtcgcgacgaactgaccaagaaccaggtgtcgctgacctgtctggtcaaaggcttc
tatccgtctgatattgcagtggaatgggagtcaaatggtcagcctgagaacaattacaagaccacccccgcctgtt
ctggactccgatggctcttttctttctgtatagcaagctgaccgtggataaatcccgctggcagcagggtaacgtg
ttcagctgctcagtgatgcatgaagccctgcacaatcattacacccagaagagtctgtcgctgagcccgggtaaa
taa.

Pep16-MMP9-NGAL-Fc (SEQ ID NO: 43)
MLLVNQSHQGFNKEHTSKMVSAIVLYVLLAAAAHSAFAAGSCWSPLPFMCGGSVPLSLYSGSQDSTSDLIPAPPL
SKVPLQQNFQDNQFHGKWYVVGLAGNRILRDDQDPQNMYATIYELKEDKSYNVISVISSHKKCEYTIATFVPGSQ
PGEFTLGNIKSYGDKISYLVRVVSTDYNQYAVVFFKKASQNAEFFAITIYGRIKELASELKENFIRFSKSLGLPE
NHIVFPVPIDQCIDGSRSGGISGGGSVPGSGSSGSTSGSGKSSEGSGQASTHICPPCPAPELLGGPSVFLFPPKP
KDILMISRIPEVICVVVDVSHEDPEVKFNWYVDGVEVHNAKTKPREEQYNSTYRVVSVLIVLHQDWLNGKEYKCK
VSNKALPAPIEKTISKAKGQPREPQVYTLPPSRDELTKNQVSLICLVKGFYPSDIAVEWESNGQPENNYKTIPPV
LDSDGSFFLYSKLTVDKSRWQQGNVFSCSVMHEALHNHYTQKSLSLSPGK (SEQ ID NO: 44)
MKYLLPTAAAGLLLLAAQPAMA.

(SEQ ID NO: 45)
MLLLVTSLLLCELPHPAFLLI.

(SEQ ID NO: 46)
GGSVPLSLYSGG.

(SEQ ID NO: 47)
GGSVPGSGSSGG.

(SEQ ID NO: 48)
GGSGGSVPLSLY.

(SEQ ID NO: 49)
GGSGGSVPLSLYSGG.

(SEQ ID NO: 50)
SGGGSGGGSVPLSLYSGG.

-continued

```
                                                        (SEQ ID NO: 51)
SGGGSGGGSVPLSLYSGGSGG.

(SEQ ID NO: 52)
YGLGFNF.

(SEQ ID NO: 53)
RIDETLQ.

(SEQ ID NO: 54)
FTPWPEA.

(SEQ ID NO: 55)
WPEWDLW.

(SEQ ID NO: 56)
EKWFRFM.

(SEQ ID NO: 57)
YLELMHS.

(SEQ ID NO: 58)
SVLPPFM.

(SEQ ID NO: 59)
WSPLPFM.
```

The invention claimed is:

1. A recombinant CTLA-4 binding protein comprising:
   (i) a CTLA-4 binding domain;
   (ii) a CTLA-4 binding domain masking peptide; and
   (iii) a cleavable peptide linker connecting said CTLA-4 binding domain masking peptide to said CTLA-4 binding domain,
       wherein said CTLA-4 binding domain comprises a CTLA-4 binding lipocalin 2 (LCN2) comprising the amino acid sequence of SEQ ID NO: 34, wherein said CTLA-4 binding domain masking peptide comprises an amino acid sequence selected from the group consisting of SEQ ID NOs: 1-14 and 52-59 and wherein said cleavable peptide linker comprises a tumor-associated protease cleavage site.

2. The recombinant CTLA-4 binding protein of claim 1, wherein said CTLA-4 binding domain masking peptide comprises the amino acid sequence of SEQ ID NO:12.

3. The recombinant CTLA-4 binding protein of claim 1, wherein said CTLA-4 binding domain masking peptide comprises the amino acid sequence of SEQ ID NO:9.

4. The recombinant CTLA-4 binding protein of claim 1, further comprising a glycoprotein secretion signal selected from the group consisting of (i) a glycoprotein (gp) 67 secretion signal comprising the amino acid sequence of SEQ ID NO: 35, (ii) a pELB signal comprising the amino acid sequence of SEQ ID NO: 44, (iii) a human granulocyte-macrophage colonystimulating factor receptor (GM-CSFR) comprising the amino acid sequence of SEQ ID NO: 45, and (iv) an alpha-chain signal sequence (CAR) comprising the amino acid sequence of SEQ ID NO: 61.

5. The recombinant CTLA-4 binding protein of claim 1, wherein said cleavable peptide linker connects said CTLA-4 binding domain masking peptide to the N-terminus of said CTLA-4 binding domain.

6. The recombinant CTLA-4 binding protein of claim 1, wherein said cleavable peptide linker connects said CTLA-4 binding domain masking peptide to the C-terminus of said CTLA-4 binding domain.

7. The recombinant CTLA-4 binding protein of claim 1, wherein said cleavable peptide linker comprises a protease cleavage site.

8. The recombinant CTLA-4 binding protein of claim 7, wherein said protease cleavage site is a tumor-associated protease cleavage site.

9. The recombinant CTLA-4 binding protein of claim 7, wherein said protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site.

10. The recombinant CTLA-4 binding protein of claim 9, wherein said matrix metalloprotease (MMP) cleavage site is a MMP9 cleavage site, a MMP 13 cleavage site or a MMP 2 cleavage site.

11. The recombinant CTLA-4 binding protein of claim 9, wherein said disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site.

12. The recombinant CTLA-4 binding protein of claim 1, wherein said CTLA-4 binding domain is further covalently attached to a dimerizing domain that is an Fc protein domain.

13. The recombinant CTLA-4 binding protein of claim 12, wherein said Fc protein domain is an IgG1 Fc protein or an IgM Fc protein.

14. A recombinant nucleic acid encoding the recombinant CTLA-4 binding protein of claim 1.

15. A method of treating a CTLA-4-mediated cancer in a human subject in need thereof, said method comprising administering to the subject a therapeutically effective amount of a recombinant CTLA-4 binding protein of claim 1.

* * * * *

UNITED STATES PATENT AND TRADEMARK OFFICE
CERTIFICATE OF CORRECTION

| | | |
|---|---|---|
| PATENT NO. | : 10,689,423 B2 | Page 1 of 1 |
| APPLICATION NO. | : 15/543209 | |
| DATED | : June 23, 2020 | |
| INVENTOR(S) | : John Williams et al. | |

It is certified that error appears in the above-identified patent and that said Letters Patent is hereby corrected as shown below:

On the Title Page

Item (72) Inventors, insert after the names of John Williams and Ulrich Rodeck, the names of co-inventors as follows:
-- Miso Park, Duarte, CA (US);
Kurt Jenkins, Duarte, CA (US) --

Signed and Sealed this
Thirtieth Day of September, 2025

John A. Squires
*Director of the United States Patent and Trademark Office*